United States Patent [19]

Fässler et al.

[11] Patent Number: 6,110,946

[45] Date of Patent: Aug. 29, 2000

[54] ANTIVIRALLY ACTIVE HETEROCYCLIC AZAHEXANE DERIVATIVES

[75] Inventors: Alexander Fässler, Macclesfield, United Kingdom; Guido Bold, Gipf-Oberfrick; Hans-Georg Capraro, Rheinfelden, both of Switzerland; Marc Lang, Mulhouse, France; Satish Chandra Khanna, Bottmingen, Switzerland

[73] Assignee: Novartis Finance Corporation, Summit, N.J.

[21] Appl. No.: 09/108,481

[22] Filed: Jul. 1, 1998

Related U.S. Application Data

[62] Division of application No. 08/831,630, Apr. 9, 1997, Pat. No. 5,849,911.

[30] Foreign Application Priority Data

Apr. 22, 1996 [CH] Switzerland ............... 1018/96
Jan. 31, 1997 [CH] Switzerland ............... 223/97

[51] Int. Cl.$^7$ ............ A01K 31/44; C07D 401/00; C07D 277/04; C07C 261/00; C07C 241/00
[52] U.S. Cl. ............ 514/333; 514/222; 564/313; 564/321; 564/34; 564/37; 560/159; 548/182; 548/183; 548/184; 548/185; 548/186; 548/189; 548/190; 548/191; 546/256; 546/275
[58] Field of Search .............. 564/313, 321, 564/34, 37; 560/159; 514/333, 222; 548/182–191; 546/256, 275

[56] References Cited

U.S. PATENT DOCUMENTS

| | | | |
|---|---|---|---|
| 3,260,740 | 7/1966 | Frederick et al. | 524/156 |
| 4,556,654 | 12/1985 | Showalter et al. | 514/222 |
| 5,461,067 | 10/1995 | Norbeck et al. | 514/333 |
| 5,621,109 | 4/1997 | Norbeck et al. | 548/182 |

FOREIGN PATENT DOCUMENTS

| | | |
|---|---|---|
| 0486948 | 5/1992 | European Pat. Off. |
| 0521827 | 1/1993 | European Pat. Off. |
| 0604368 | 6/1994 | European Pat. Off. |
| 9318006 | 9/1993 | WIPO . |
| 9414436 | 7/1994 | WIPO . |
| 9419332 | 9/1994 | WIPO . |
| 9422840 | 10/1994 | WIPO . |
| 9502582 | 1/1995 | WIPO . |
| 9507269 | 3/1995 | WIPO . |

OTHER PUBLICATIONS

Fässler et al., Bioorganic & Medicinal Chemistry Letters, vol. 3, No. 12, pp. 2837–2842.
Fässler, et al., J. Med. Chem. vol. 39, 1996,pp. 3203–3216.
Sham, et al., J. Chem. Soc. Chem. Commun., 1993, P–1052.

Primary Examiner—Alan L. Rotman
Assistant Examiner—Rita J. Desai
Attorney, Agent, or Firm—Hesna J. Pfeiffer

[57] ABSTRACT

There are described compounds of formula I*,

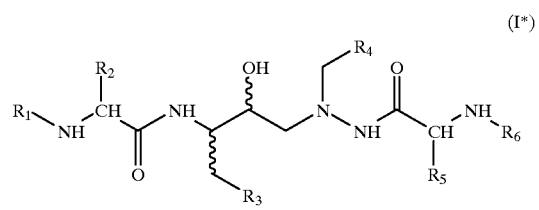

wherein
$R_1$ is lower alkoxycarbonyl,
$R_2$ is secondary or tertiary lower alkyl or lower alkylthio-lower alkyl,
$R_3$ is phenyl that is unsubstituted or substituted by one or more lower alkoxy radicals, or $C_4$–$C_8$cycloalkyl,
$R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—SO$_2$—) and is unsubstituted or substituted by lower alkyl or by phenyl-lower alkyl,
$R_5$, independently of $R_2$, has one of the meanings mentioned for $R_2$, and
$R_6$, independently of $R_1$, is lower alkoxycarbonyl,
or salts thereof, provided that at least one salt-forming group is present.

The compounds are inhibitors of retroviral aspartate protease and can be used, for example, in the treatment of AIDS. They exhibit outstanding pharmacodynamic properties.

12 Claims, No Drawings

ANTIVIRALLY ACTIVE HETEROCYCLIC AZAHEXANE DERIVATIVES

CROSS-REFERENCE

This application is a Divisional of application Ser. No. 08/831,630, filed Apr. 9, 1997 U.S. Pat. No. 5,849,911.

The invention relates to heterocyclic azahexane derivatives that can be employed as substrate isosteres of retroviral aspartate proteases, to salts thereof, to processes for the preparation of those compounds and their salts, to pharmaceutical compositions comprising those compounds or their salts, and to the use of those compounds or their salts (alone or in combination with other antiretrovirally active compounds) in the therapeutic or diagnostic treatment of the human or animal body or in the preparation of pharmaceutical compositions.

BACKGROUND TO THE INVENTION

According to WHO estimates there are clearly more than 20 million people infected by the "Human Immuno Deficiency Virus", HIV-1 or HIV-2. With very few exceptions, in infected subjects the disease results, by way of preliminary stages, such as ARDS, in a manifest disease of the immune system which is known as "Acquired Immunodeficiency Syndrome" or AIDS. In the overwhelming number of cases the disease sooner or later leads to the death of the infected patients.

Hitherto, the treatment of retroviral diseases, such as AIDS, has involved principally the use of inhibitors of reverse transcriptase, an enzyme effective in the conversion of retroviral RNA into DNA, such as 3'-azido-3-'-deoxythymidine (AZT) or dideoxyinosine (DDI), and also trisodium phosphonoformate, ammonium-21-tungstenato-9-antimonate, 1-β-D-ribofuranoxyl-1,2,4-triazole-3-carboxamide and dideoxycytidine and also adriamycin. Attempts have also been made to introduce into the body, for example in the form of a recombinant molecule or molecule fragment, the T4-cell receptor which is present on certain cells of the defence system of the human body and is responsible for the anchoring and introduction of infectious virus particles into those cells and thus for their infection, the objective being that binding sites for the virus will be blocked so that the virions will no longer be able to bind to the cells. Compounds that prevent the virus penetrating the cell membrane in some other way, such as polymannoacetate, are also used.

The first inhibitor of so-called retroviral aspartate protease to be approved for combatting the infection was saquinavir, [N-tert-butyl-decahydro-2-[2(R)-hydroxy-4-phenyl-3(S)-[[N-2-quinolyl-carbonyl-L-asparaginyl]amino]butyl]-(4aS, 8aS)-isoquinoline-3(S)-carboxamide (Ro 31-8959)]. since then others have followed (indinavir (Merck) and ritonavir (Abbott)).

Also under development are a number of further inhibitor of retroviral aspartate protease, an enzyme the function of which can be characterised as follows:

In the AIDS viruses, HIV-1 and HIV-2, and other retroviruses, for example corresponding viruses in cats (FIV) and apes (SIV), the proteolytic maturation of, for example, the core proteins of the virus is brought about by an aspartate protease, such as HIV-protease. Without that proteolytic maturation, infectious virus particles cannot be formed. Owing to the central role of the said aspartate proteases, such as HIV-1- or HIV-2-protease, in the maturation of viruses and on the basis of experimental results, for example on infected cell cultures, it has become plausible that effective suppression of the maturation step brought about by that protease will suppress the assembly of mature virions in vivo. Inhibitors of that protease can therefore be used therapeutically.

The aim of the present invention is to provide a novel type of compound that is equipped, especially, with a high degree of inhibitory activity virus replication in cells, high anti-viral activity against numerous virus strains, including those which are resistant to known compounds, such as saquinavir, ritonavir and indinavir, and especially advantageous pharmacological properties, for example good pharmacokinetics, such as high bioavailability and high blood levels, and/or high selectivity.

Full description of the invention

The azahexane derivatives according to the invention are compounds of formula I*,

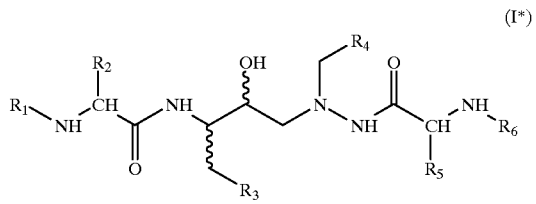

especially of formula I,

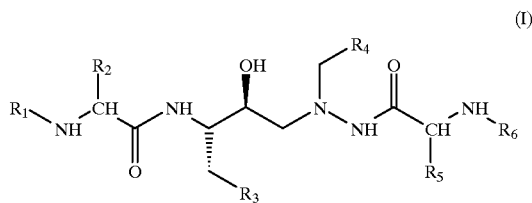

wherein
$R_1$ is lower alkoxycarbonyl,
$R_2$ is secondary or tertiary lower alkyl or lower alkylthio-lower alkyl,
$R_3$ is phenyl that is unsubstituted or substituted by one or more lower alkoxy radicals, or $C_4$–$C_8$cycloalkyl,
$R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—SO$_2$—) and is unsubstituted or substituted by lower alkyl or by phenyl-lower alkyl,
$R_5$, independently of $R_2$, has one of the meanings mentioned for $R_2$, and
$R_6$, independently of $R_1$, is lower alkoxycarbonyl,
or a salt thereof, provided that at least one salt-forming group is present.

Those compounds exhibit unexpectedly good and surprisingly positive pharmacological properties, as indicated in detail below, and are relatively simple to synthesise.

Unless indicated to the contrary, the general terms used hereinabove and hereinbelow preferably have the following meanings within the scope of this disclosure:

The term "lower" indicates a radical having up to and including a maximum of 7 carbon atoms, preferably up to and including a maximum of 4 carbon atoms, the radicals in question being unbranched or branched one or more times.

Lower alkyl and $C_1$–$C_4$alkyl are especially tert-butyl, sec-butyl, isobutyl, n-butyl, isopropyl, n-propyl, ethyl and methyl.

Any reference to compounds, salts and the like in the plural also includes a compound, a salt and the like.

Any asymmetric carbon atoms present, for example the carbon atoms bonded to the radicals $R_2$ and $R_5$, may be in the (R)-, (S)- or (R,S)-configuration, preferably in the (R)- or (S)-configuration, the (S)-configuration being especially preferred in the case of the carbon atoms carrying the radical $R_2$ and/or $R_5$ in compounds of formula I. Accordingly, the compounds in question may be in the form of isomeric mixtures or in the form of pure isomers, preferably in the form of enantiomerically pure diastereoisomers.

Lower alkoxycarbonyl is preferably $C_1$-$C_4$alkoxycarbonyl wherein the alkyl radical may be branched or unbranched, and is especially ethoxycarbonyl or methoxycarbonyl.

Secondary or tertiary lower alkyl is especially sec-butyl, tert-butyl or isopropyl.

Lower alkylthio-lower alkyl is especially methylthiomethyl.

Phenyl that is unsubstituted or substituted by one or more lower alkoxy radicals is especially phenyl that is unsubstituted or substituted by from one to three lower alkoxy radicals, especially methoxy. In the case when there are three methoxy substituents, these are especially in the 2,3,4-positions of the phenyl ring and in the case when there is one methoxy substituent, that substituent is especially in the 2-, 3- or, more especially, in the 4-position. Unsubstituted phenyl is preferred.

$C_4$-$C_8$cycloalkyl is especially cyclopentyl or, more especially, cyclohexyl.

As $R_3$ phenyl is preferred to cyclohexyl.

In phenyl or cyclohexyl substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—$SO_2$—) and is unsubstituted or substituted by lower alkyl or by phenyl-lower alkyl, the corresponding heterocyclyl has especially the following meanings:

Unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—$SO_2$—) and is unsubstituted or substituted by lower alkyl, especially by methyl, or by phenyl-lower alkyl wherein the lower alkyl radical is unbranched or branched, especially by 1-methyl-1-phenylethyl, is especially one of the following radicals bonded by way of a ring carbon atom: thienyl (=thiophenyl); oxazolyl; thiazolyl; imidazolyl; 1,4-thiazinyl; triazolyl that is unsubstituted or, especially, substituted by 1-methyl-1-phenyl-ethyl or preferably by tert-butyl or especially by methyl, such as 1-, 2- or 4-(methyl or tert-butyl)-triazol-3-yl; tetrazolyl that is unsubstituted, or especially, substituted by 1-methyl-1-phenyl-ethyl or preferably by lower alkyl, such as by tert-butyl or especially by methyl, such as 2H-tetrazol-5-yl substituted by 1-methyl-1-phenyl-ethyl or preferably by lower alkyl, such as by tert-butyl or especially by methyl, or 1H-tetrazol-5-yl substituted by tert-butyl or especially by methyl; pyridinyl; pyrazinyl; and pyrimidinyl; more especially 2- or 3-thienyl (=thiophen-2-yl or thiophen-3-yl); thiazol-5-yl; thiazol-2-yl; 2H-tetrazol-5-yl that is unsubstituted or, especially, substituted in the 2-position by 1-methyl-1-phenyl-ethyl or preferably by tert-butyl or especially by methyl; 1H-tetrazol-5-yl substituted in the 1-position by methyl; pyridin-2-yl; pyridin-3-yl; pyridin-4-yl; or pyrazin-2-yl.

$R_4$ is preferably phenyl substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—$SO_2$—) and is unsubstituted or substituted by lower alkyl or by phenyl-lower alkyl, wherein heterocyclyl preferably has the meanings defined above as being preferred.

The compounds of formula I preferably have the formula Ia,

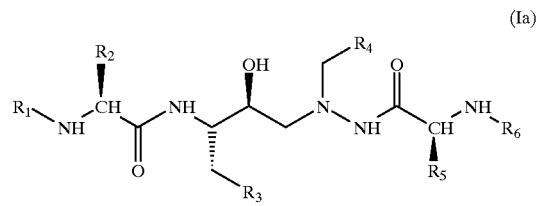

(Ia)

wherein the radicals are as defined.

Salts are especially the pharmaceutically acceptable salts of compounds of formula I.

Such salts are formed, for example, by compounds of formula I having a basic $R_4$—$CH_2$— carrying nitrogen atom as acid addition salts, preferably with inorganic acids, for example hydrohalic acid, such as hydrochloric acid, sulfuric acid or phosphoric acid, or with strong organic sulfonic, sulfo or phosphoric acids or N-substituted sulfamic acids (preferably: pKa<1). Other salts may be present when basic heterocyclyl radicals, such as pyridyl, are present in $R_4$. Those salts includes especially acid addition salts with organic or inorganic acids, especially the pharmaceutically acceptable salts. Suitable inorganic acids are, for example, hydrohalic acids, such as hydrochloric acid, sulfuric acid and phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydrocxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetycysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicyclic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicyclic acid, phthalic acid, phenylacetic acid, mandelic acid, cinnamic acid, glucuronic acid, galacturonic acid, methanesulfonic or ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

When negatively charged radicals are present, such as tetrazolyl in $R_4$, salts may also be formed with bases, e.g. metal or ammonium salts, such as alkali metal or alkaline earth metal salts, e.g. sodium, potassium, magnesium or calcium salts or ammonium salts with ammonia or suitable organic amines, such as tertiary monoamines, e.g. triethylamine or tri-(2-hydroxyethyl)-amine, or heterocyclic basis e.g. N-ethyl-piperidine or N,N'-dimethylpiperazine.

For the purposes of isolation or puridication it is also possible to use pharmaceutically unsuitable salts, for example picrates or perchlorates. Only the pharmaceutically acceptable salts or the free compounds (optionally in the form of pharmaceutically compositions) are used therapeutically and they are therefore preferred.

In view of the close relationship between the novel compounds in free form and in the form of their salts, including those salts that can be used as intermediates, for example in the purification of the novel compounds or for identifying them, hereinbefore and hereinafter any reference to the free compounds should be understood as including the corresponding salts as appropriate and expedient.

The compounds of formula I have valuable pharmacological properties. They have anti-retroval activity, especially against the viruses HIV-1 and HIV-2 which are regarded as causes of AIDS, and may surprisingly exhibit synergistic effects in combination with other compounds that are active against retroviral aspartate proteases. The compounds of formula I are inhibitors of retroviral aspartate proteases, especially inhibitors of the aspartate protease of HIV-1 or also HIV-2 and are therefore suitable for the treatment of retroviral diseases, such as AIDS or its preliminary stages (e.g. ARDS). Compounds of formula I also exhibit activity against corresponding animal retroviruses, such as SIV (in apes) or FIV (in cats).

Compounds of formula I exhibit, surprisingly, especially advantageous and important pharmacological properties, for example a very high antiviral activity in cell tests against various virus strains, including those which are resistant to other protease inhibitors, for example in MT2-cells, good pharmacokinetics, such as high bioavailability, high selectivity and, especially, high blood levels (even in the case of oral administration).

The inhibitory action of the compounds of formula I on the proteolytic activity of HIV-1-protease can be shown, for example, according to known procedures (see A. D. Richards et al., J. Biol. Chem. 265 (14), 7733–7736 (1990)). In that method the inhibition of the action of HIV-1-protease (preparation: see S. Billich et al., J. Biol. Chem. 263 (34), 17905–17908 (1990)) is measured in the presence of the icosapeptide RRSNQVSQNYPIVQNIQGRR (a synthetic substrate of HIV-1-protease, prepared by peptide synthesis in accordance with known procedures (see J. Schneider et al., Cell 54, 363–368 (1988)), which contains as substrate analogue one of the cleavage sites of the gag-precursor protein (natural substrate of HIV-1-protease). That substrate and its cleavage products are analysed by high performance liquid chromatography (HPLC).

The test compound is dissolved in dimethyl sulfoxide. The enzymatic test is carried out by adding suitable dilutions of the inhibitor in 20 mM β-morpholinoethanesulfonic acid (MES) buffer pH 6.0 to the test mixture. That mixture consists of the above-mentioned icosapeptide (122 $\mu$M) in 20 mM MES-buffer pH 6.0. 100 $\mu$l are used per test batch. The reaction is started by the addition of 10 ml of HIV-1-protease solution and is stopped after one hour's incubation at 37° C. by the addition of 10 $\mu$l of 0.3M $HClO_4$. After centrifugation of the sample at 10 000×g for 5 minutes, 20 $\mu$l of the resulting supernatant are applied to a 125×4.6 mm Nucleosil® C18-5m-HPLC column (reversed-phase material supplied by Macherey & Nagel, Düren, FRG, based on silica gel that has been charged with $C_{18}$alkyl chains). The uncleaved icosapeptide and its cleavage products are eluted from the column by means of the following gradient: 100% eluant 1→50% eluant 1+50% eluant 2 (eluant 1: 10% acetonitrile, 90% $H_2O$, 0.1% trifluoroacetic acid (TFA); eluant 2: 75% acetonitrile, 25% $H_2O$, 0.08% TFA) for 15 minutes, throughflow rate 1 ml/min. The quantification of the eluted peptide fragments is carried out by measuring the peak height of the cleavage product at 215 nm.

Compounds of formula I exhibit inhibitory actions in the nanomolar range; they preferably exhibit $IC_{50}$ values ($IC_{50}$= that concentration which brings about a 50% reduction in the activity of HIV-1-protease in comparison with a control without inhibitor) of approximately $2\times10^{-7}$ to $5\times10^{-9}$ M, preferably $5\times10^{-8}$ to $5\times10^{-9}$ M.

An alternative method (see Matayoshi et al., Science 247, 954–958 (1990), here modified) of determining the inhibitory action against HIV-1-protease may be described briefly as follows: the protease (purification: see Leuthardt et al., FEBS Lett. 326, 275–80 (1993)) is incubated at room temperature in 100 $\mu$l of assay buffer (20 mM MES pH 6.0; 200 mM NaCl; 1 mM dithiothreitol; 0.01% polyethylene glycol (average molecular weight 6000 to 8000 da) with 10 $\mu$M fluorogenic substrate SC4400 (4-(4-dimethylaminophenylazo)benzoyl-γ-aminobutyryl-Ser-Gln-Asn-Tyr-Pro-Ile-Val-Gln-EDANS (EDANS=5-(2-aminoethylamino)-1-naphthalensulfonic acid); Neosystem Laboratoire, France). The reaction is discontinued by the addition of 900 $\mu$l of 0.03M $HClO_4$. The HIV-1-protease activity is determined by measuring the increase in fluorescence at λex=336, λem=485 nm. The $IC_{50}$ values of compounds of formula I are determined as the concentration of the compound that is necessary to inhibit the protease activity in the assay by 50%. The numerical values are obtained from computer-generated graphs from data relating to at least 5 concentrations of the compound of formula I in question with threefold determination per concentration.

In a further test it can be shown that compounds of formula I protect cells normally infected by HIV from such an infection or at least slow down such an infection. For this test, MT-2-cells infected with HIV-1/MN are used. MT-2-cells have been transformed with HTLV-1 (a virus causing leukaemia) and a continuous producer thereof; they are therefore especially sensitive to the ctyopathogenic effect of HIV. MT-2-cells can be obtained via the AIDS Research and Reference Reagent Program, Division of AIDS, NIAID, NIH from Dr. Douglas Richman (see J. Biol. Chem. 263, 5870–5875 (1988) and also Science 229, 563–566 1985)). The MT-2-cells are cultured in RPMI 1640-medium (Gibco, Scotland; RPMI comprises an amino acid mixture without glutamine) supplemented with 10% heat-inactivated foetal calf serum, glutaemine and standard antibiotics. In all cases the cells, and also the virus stock solution used for the infection (HIV-1/MN), are free of mycoplasms. The virus stock solution is prepared as a cell culture supernatant of the permanently infected cell line H9/HIV-1/MN, which can likewise be obtained via the AIDS Research and Reference Program, Division of AIDS, NIAID, NIH from Dr. Robert Gallo (see also Science 224, 500–503 (1984) and Science 226, 1165–1170 (1984)). The titre of the HIV-1/MN virus stock solution (determined by titration onto MT-2-cells) is $4.2\times10^5$ TCID50/ml (TCID50=Tissue Culture Infective Dose=dose that infects 50% of the MT-2-cells). In order to measure the infection-inhibiting action of the compounds of formula I, 50 $\mu$l of the test compound in question in culture medium and 2800 TCID50 of HIV-1/MN in 100 $\mu$l of culture medium are added to $2\times10^4$ exponentially growing MT-2-cells which have been applied in 50 $\mu$l of culture medium to 96-well microtitre plates (having a round base). After 4 days' incubation (at 37° C. 5% $CO_2$) a 10 $\mu$l sample of the supernatant is taken from each well, transferred to a further 96-well microtitre plate and (if necessary) stored at −20° C.

In order to measure the activity of the virus-associated reverse transcriptase, 30 μl of reverse transcriptase (TR) cocktail are added to each sample. The reverse transcriptase cocktail consists of 50 mM Tris (α,α,α-tris(hydroxymethyl) methylamine, Ultra pur, Merck, Germany) pH 7.8; 75 mM KCl, 2 mM dithiothreitol, 5 mM MgCl$_2$; 0.1% Nonidet P-40 (detergent; Sigma, Switzerland), 0.8 mM EDTA, 10 μg/ml Poly-A (Pharmacia, Uppsala, Sweden) and 0.16 μg/ml oligo (T) (=pdT(12–18), Pharmacia, Uppsala, Sweden) as "template primer"—if desired, the mixture is filtered through a 0.45 mm Acrodisc filter (Gelman Sciences Inc., Ann Arbor, USA). It is stored at −20° C. Prior to the test, 0.1% (v/v) [alpha-$^{32}$P]dTTP is added to aliquots of the solution in order to establish a radioactivity of 10 μCi/ml.

After mixing, the plate is incubated for 2 hours at 37° C. 5 μl of the reaction mixture are transferred to DE81 paper (Whatman, one filter per well). The dried filters are washed three times for 5 minutes with 300 mM NaCl/25 mM trisodium citrate and then once with ethanol and again dried in the air. The radioactivity on the filters is measured in a Matrix Packard 96-well counter (Packard, Zürich, Switzerland). The ED$_{90}$ values are calculated and are defined as the concentration of the test compound that reduces the RT activity by 90% in comparison with a control without test compound.

The preferred compounds of formula I here exhibit an ED$_{90}$, that is to say a 90% inhibition of virus replication, at concentrations of from $10^{-7}$ to $10^{-9}$M, especially from $5 \times 10^{-9}$ to $10^{-9}$ M.

Accordingly, the compounds of formula I are suitable for the highly effective retardation of the replication of HIV-1 in cell cultures.

In order to determine their pharmacokinetics, the compounds of formula I are dissolved in dimethyl sulfoxide (DMSO) in a concentration of 240 mg/ml. The resulting solutions are diluted 1:20 (v/v) with 20% (w/v) aqueous hydroxypropyl-β-cyclodextrin solution in order to obtain a concentration of the test compound in question of 12 mg/ml. The resulting solution is treated briefly with ultrasound and administered orally to female BALB/c mice (Bomholtgarden, Copenhagen, Denmark) by artificial tube feeding at a dose of 120 mg/kg. At fixed times (for example 30, 60, 90, 120 min) after administration, mice are sacrificed and the plasma stored in heparinised test tubes. The blood is centrifuged (12000×g, 5 min) and the plasma removed. The plasma is deproteinised by the addition of an equal volume of acetonitrile. The mixture is mixed using a vortex mixer and and left to stand at room temperature for 20 to 30 minutes. The precipitate is pelleted by centrifugation (12000×g, 5 min), and the concentration of the test compound is determined by reversed phase high performance liquid chromatography (HPLC).

The HPLC analysis of the samples obtained in accordance with the method described above is carried out on a 125×4.6 mm Nucleosil® C$_{18}$-column (reversed-phase material supplied by Macherey & Nagel, Düren, Germany, based on silica gel derivatised with carbon radicals having 18 carbon atoms), using a 2 cm long preliminary column of the same column material. The test is carried out with the following linear acetonitrile/water gradient (in each case in the presence of 0.05% trifluoroacetic acid): 20% acetonitrile to 100% acetonitrile for 20 min; then 5 min 100% acetonitrile; then returning to the initial conditions for 1 min and 4 min reequilibration. The flow rate is 1 ml/min. Under those conditions the compound of formula I from Example 1, for example, has a retention time of about 15.5 minutes, and its detection limit is 0.1–0.2 μM. The test compound is detected by UV absorption measurement at 255 nm. Peaks are identified by the retention time and the UV spectrum between 205 and 400 nm. The concentrations are determined by the external standard method; the peak heights are obtained for determining the concentrations by comparison with standard curves. The standard curves are obtained by analogous HPLC analysis of mouse plasma that contains known concentrations of the test compound in question and that has been worked up in accordance with the method described above.

In that experiment compounds of formula I produce plasma concentrations far above the ED$_{90}$ determined above in the cell experiment, for example up to 8000 times greater than the ED$_{90}$ after 30 minutes and up to 10 500 times greater than the ED$_{90}$ after 90 minutes, preferably plasma concentrations of from 0.1 μM to 25 μM, especially from 1 to 25 μM, 30 minutes after oral administration, and plasma concentrations of from 0.5 to 35 μM, specially from 1 to 35 μM, 90 minutes after oral administration.

Analogously, in dogs, the blood level of the compounds of formula I, for example the title compound of Example 46, can be measured, for example, using the formulations according to either Example 63 or Example 64, there being used, for example, from 92 to 100 mg/kg of the compound which is administered by stomach tube, the blood levels then being measured, e.g. 1, 2, 3, 4, 6, 8 and 24 hours after administration. Here, also, blood levels in the micromolar range can be found.

In particular, the combination of high bioavailability (high plasma levels), which is surprising in itself, and unexpectedly excellent ED$_{90}$ in the cell experiment renders the compounds of the present invention valuable in an unforeseen way. Activity against inhibitors of retroviral aspartate proteases to which resistance has already developed is also still possible and is a further important advantage of the compounds according to the invention.

That can be demonstrated, for example, by the following or analogous tests:

Inhibitor-resistant HIV-1 protease variants are cloned as follows:

By way of PCR-supported mutagensis and cloning, HIV-1 protease mutants are generated that are based on the infectious clone pNL4-3 (freely available via the "NIH AIDS reference and reagent program", the original reference is A. Adachi et al. J. Virol (1986) 59, 284–91—but it can, of course, be any other HIV clone, or even clinical material, provided that comparability is ensured). Those otherwise isogenic point mutants contains only those changes which have been described in publications in connection with viral resistance to various protease inhibitors. The cloned fragments are, for example, only 500 base pairs in length, all of the remainder being unchanged. By using mutations in always the same clone, direct comparability is ensured, which could not be the case in a direct comparison of clinical samples or of different HIV clones. In the transient DNA transfection assay in human T4-positive cells (HeLa T4), the resulting proviruses also demonstrate the finding of reduced inhibitor activity in comparison with the wild type virus, that is to say increased resistance. That system is used as a transient DNA transfection system for tests:
1) in order to identify possible cross-resistances of protease variants to several protease inhibitors; and
2) in order to establish the potency and resistance profile of novel inhibitor candidates.

For example, in the said transfection system 1-[4-(pyridin-2-yl)phenyl]-4(S)-hydroxy-5(S)-2,5-bis-[N-(N-methoxycarbonyl-(L)-tert-leucyl)amino]-6-phenyl-2- azahexane (Example 46) has an in vitro potency that, with an IC90 of <30 nM, is in practical terms better than that of saquinavir (Hoffmann-LaRoche, see below) and the activity against a resistant varient (45I/76F strain) which has been established against 5(S)-(tert-butoxycarbonylamino)-4(S)-hydroxy-6-phenyl-2(R)-(2,3,4-trimethoxyphenylmethyl)-hexanoyl-(L)-valyl-N-(2-methoxyethyl)-amide (=Lainavir, see EP 0 708 085, published on Apr. 24, 1996; Novartis AG, originally Ciba-Geigy AG), is comparable with saquinavir and better than that of indinavir (Merck & Co., Inc. see below) or ritonavir (Abbott, see below). Compared with other strains (e.g. 46I/47V/50V (VX478)), 10 nM produced an activity that was more potent (not quantified) than that of saquinavir, ritonavir and indinavir. Instead of the strains mentioned, there may be used any human T4-positive cells, such as the HeLa T4 cells, deposited under that name by Richard Axel and Pual Maddon in "NIH AIDS reference and reagent program" and obtainable via that source.

In principle, the relevant mutations for the above test systems for resistances are known (see e.g. relating to the 48V/90M strain (saquinavir resistance): Jacobsen, H., Yasargil, K., Winslow, D. L., Craig, J. C., Krohn, A., Duncan, I. B., & Mous, J. Virology 206, 527 (1995); Merck Mutationen (several, e.g. 71V/82T/84V): Condra, J. H., Schleiff, W. A., Blahy, O. M., Gabryelski, L. J., Graham, D. J., Quintero, J. C., Rohodes, A., Robbins, H. L. Roth, E., Shivaprakash, M., & et al Nature 374, 569 (1995); Abbott 82V/84A strain: Markowitz, M., Mo, H., Kempf, D. J., Norbeck, D. W., Bhat, T. N., Erickson, J. W., & Ho, D. D. J. Virol. 69, 701 (1995).

In the determination of the anti-enzymatic activity against numerous human aspartate proteases in accordance with known methods (see, for example, Biochem, J. 265, 871–878 (1990)), compounds of formula I exhibit a high selectivity towards the retroviral aspartate protease of HIV, especially HIV-1. For example, the inhibition constant ($IC_{50}$) for compounds for formula I in the test against cathepsin D is more than 10 $\mu$M, especially more than 25 $\mu$M. The $IC_{50}$ against human cathepsin D in that test is measured at pH 3.1. The test is carried out in accordance with known procedures using the substrate KPIQF*NphRL (see Jupp, R. A., Dunn, B. M., Jacobs, J. W., Vlasuk, G., Arcuri, K. E., Veber, D. F., S. Perow, D. S., Payne, L. S., Boger, J., DeLazlo, S., Chakrabarty, P. K., TenBroeke, J., Hangauer, D. G., Ondeyka, D., Greenlee, W. J. and Kay, J.: The selectivity of statine-based inhibitors against various human aspartic proteases. Biochem. J. 265: 871–878 (1990)).

The compounds of formula I can be used alone or in combination (as a set combination of corresponding compositions or as a combination of individual compounds or individual compositions in a time-staggered sequence) with one or more other pharmaceutically active substances (or salts thereof provided that at least one salt-forming group is present) that are effective against retroviruses, especially HIV, such as HIV-1 or HIV-2; especially with inhibitors of reverse transcriptase, more especially nucleoside analogues, especially 3'-azido-3'-deoxypyrimidine (=zidovudine=®RETROVIR, Burroughs-Wellcome), 2',3'-dideoxycytidine (=zalcitabine=®HIVID, Hoffmann-LaRoche), 2',3'-dideoxyinosine (=didanosine=®VIDEX, Bristol-Myers-Squibb) or (2R,cis)-4-amino-1-(2-hydroxymethyl-1,3-oxathiolan-5-yl)-(1H)-pyrimidin-2-one (=lamivudine, Glaxo); especially d4C=2',3'-didehydro-2',3'-dideoxycytidine, d4T=2',3'-didehydro-2',3'-dideoxythymidine (=stavudine=®ZERIT) or 2',3'-dideoxyinosine (=ddlno=DZI=didanosine=®VIDEX); or non-nucleoside analogues, such as 11-cycloprpyl-5,11-dihydro-4-methyl-(6H)-dipyrido[3,2-b;2',3'-e]-[1,4]-diazepin-6-one; or with one or more (especially one or also two) other inhibitors of retroviral aspartate proteases, especially aspartate proteases of HIV, such as HIV-1 and HIV-2, especially a) one of the inhibitors mentioned in EP 0 346 847 (published on Dec. 12, 1989) and EP 0 432 695 (published on Jun. 19, 1991; corresponds to U.S. Pat. No. 5,196,438, published on Mar. 23, 1993), especially the compound designated Ro 31-8959 (=saquinavir; Hoffmann-LaRoche);

b) one of the inhibitors mentioned in EP 0 541 168 (published on May 12, 1993; corresponds to U.S. Pat. No. 5,413,999), especially the compound designated L-735,524 (=indinavir=®CRIXIVAN; Merck & Co., Inc.);

c) one of the inhibitors mentioned in EP 0 486 948 (published on May 27, 1992; corresponds to U.S. Pat. No. 5,354,866), especially the compound designated ABT-538 (=ritonavir; Abbott);

d) the compound designated KVX-478 (or VX-478 or 141W94; GlaxoWellcome, Vertex and Kissei Pharmaceuticals)

e) the compound designated AG-1343 (Agouron);

f) the compound designated KNI-272 (Nippon Mining);

g) the compound designated U-96988 (Upjohn);

h) the compound designated BILA-2011 BS (=palinavir; Boehringer-Ingelheim), and/or I) the compound 5(S)-(tert-butoxycarbonylamino)-4(S)-hydroxy-6-phenyl-2(R)-(2,3,4-trimethoxyphenylmethyl)-hexanoyl-(L)-valyl-N-(2-methoxy-ethyl)-amide (=lasinavir, see EP 0 708 085, published on Apr. 24, 1996; Novartis AG, originally Ciba-Geigy AG), or in each case a salt thereof, provided that salt-forming groups are present.

The compounds of formula I can also be used in the prevention, control and treatment of retrovirus infections, especially HIV, such as HIV-1 or HIV-2, in cell cultures, especially cell cultures of lymphocyte cell lines, from warm-blooded animals, which is advantageous especially in the case of very valuable cell cultures that produce, for example, specific antibodies, vaccines or messenger substances, such as interleukins and the like, and are therefore of great commercial value.

Finally, the compounds of formula I can be used as standard in experiments, for example as HPLC standards or as standard for the comparison of animal models in respect of different aspartate protease inhibitors, for example in respect of the blood levels achievable.

In the groups of preferred compounds of formula I mentioned below, it is possible where expedient (for example in order to replace more general definitions by more specific definitions or, especially, by definitions described as being preferred) to use definitions of substituents from the general definitions given above; in each case preference is given to the definitions described above as being preferred or given as examples.

Preference is given to a compound of formula I, especially of formula Ia, wherein $R_1$ is lower alkoxycarbonyl, especially methoxycarbonyl or ethoxycarbonyl, $R_2$ is isopropyl, sec-butyl (preferably in the (S)-configuration), or tert-butyl, $R_3$ is phenyl or also cyclohexyl, $R_4$ is phenyl substituted in the 4-position by one of the following radicals bonded by way of a ring carbon atom: thienyl (=thiophenyl); oxazolyl; thiazolyl; imidazolyl; 1,4-thiazinyl; triazolyl that is unsubstituted or, especially, substituted by 1-methyl-1-phenyl-ethyl or preferably by tert-butyl or especially by methyl, such as 1-, 2- or 4-(methyl or tert-butyl)-triazol-3-yl; tetrazolyl that is unsubstituted, or, especially, substituted by 1-methyl-1-phenylethyl or preferably by lower alkyl, such as by tert-butyl or especially by methyl, such as 2H-tetrazol-5-yl substituted by 1-methyl-1-phenyl-ethyl or preferably by lower alkyl, such as by tert-butyl or especially by methyl, or 1H-tetrazol-5-yl substituted by methyl; pyridinyl; pyrazinyl; and pyrimidinyl; especially 2- or 3-thienyl (=thiophen-2-yl or thiophen-3-yl); thiazol-5-yl; thiazol-2-yl; 2H-tetrazol-5-yl that is unsubstituted or, especially, substituted in the 2-position by 1-methyl-1-phenyl-ethyl or preferably by tert-butyl or especially by methyl; 1H-tetrazol-5-yl substituted in the 1-position by methyl; pyridin-2-yl; pyridin-3-yl; pyridin-4-yl; or pyrazin-2-yl;

$R_5$ is isopropyl, sec-butyl (preferably in the (S)-configuration), tert-butyl or methylthiomethyl, and $R_6$ is lower alkoxycarbonyl, especially methoxycarbonyl or ethoxycarbonyl, or a salt thereof (especially a pharmaceutically acceptable salt thereof), provided that at least one salt-forming group is present.

Greater preference is given to a compound of formula I, wherein $R_1$ is methoxycarbonyl or ethoxycarbonyl, $R_2$ is isopropyl, sec-butyl or tert-butyl, $R_3$ is phenyl, $R_4$ is phenyl substituted in the 4-position of the phenyl ring by 2- or 3-thienyl (=thiophen-2-yl or thiophen-3-yl); thiazol-5-yl; thiazol-2-yl; 2H-tetrazol-5-yl that is unsubstituted or, especially, substituted in the 2-position by 1-methyl-1-phenyl-ethyl or preferably by tert-butyl or especially by methyl; 1H-tetrazol-5-yl substituted in the 1-position by methyl; pyridin-2-yl; pyridin-3-yl; pyridin-4-yl; or by pyrazin-2-yl; and is especially 4-(thiazol-2-yl)-phenyl; 4-(thiazol-5-yl)-phenyl; 4-(pyridin-2-yl)-phenyl; or 4-(2-methyl-tetrazol-5-yl)-phenyl;

$R_5$ is isopropyl, sec-butyl, tert-butyl or methylthiomethyl; and $R_6$ is methoxycarbonyl or ethoxycarbonyl;

with the proviso that at least one of the two radicals $R_2$ and $R_5$ is tert-butyl, provided that $R_4$ is phenyl substituted in the 4-position f the phenyl ring by 2- or 3-thienyl (=thiophen-2-yl or thiophen-3-yl); thiazol-5-yl; thiazol-2-yl; 2H-tetrazol-5-yl that is unsubstituted or, especially, substituted in the 2-position by 1-methyl-1-phenyl-ethyl or preferably by tert-butyl or especially by methyl; 1H-tetrazol-5-yl substituted in the 1-position by methyl; pyridin-3-yl; pyridin-4-yl; or by pyrazin-2-yl;

or a (preferably pharmaceutically acceptable) salt thereof, provided that at least one salt-forming group is present.

Special preference is given to a compound of formula I, wherein $R_1$ is methoxycarbonyl or ethoxycarbonyl, $R_2$ is isopropyl, sec-butyl or tert-butyl, $R_3$ is phenyl, $R_4$ is 4-(thiazol-1-yl)-phenyl, 4-(thiazol-5-yl)-phenyl, 4-(pyridin-2-yl)-phenyl or 4-(2-methyltetrazol-5-yl)-phenyl;

$R_5$ is isopropyl, sec-butyl, tert-butyl or methylthiomethyl; and $R_6$ is methoxycarbonyl or ethoxycarbonyl;

or a (preferably pharmaceutically acceptable) salt thereof, provided that at least one salt-forming group is present.

Each of the compounds of formula I mentioned below, or a (preferably pharmaceutically acceptable) salt thereof, is highly preferred:

1-[4-(thiazol-5-yl)-phenyl]-4(S)-hydroxy-2-N-(N-methoxycarbonyl-(L)-valyl)amino-5(S)-N-(N-methoxycarbonyl-(L)-tert-leucyl)amino-6-phenyl-2-azahexane;

1-[4-(thiazol-5-yl)-phenyl]-4(S)-hydroxy-5(S)-2,5-bis-[N-(N-methoxycarbonyl-(L)-tert-leucyl)-amino]-6-phenyl-2-azahexane;

1-[4-(thiazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane;

1-[4-(thiazol-5-yl)-phenyl]-4(S)-hydroxy-2-N-(N-methoxycarbonyl-(L)-S-methylcysteinyl)amino-5(S)-N-(N-methoxycarbonyl-(L)-tert-leucyl)amino-6-phenyl-2-azahexane;

1-[4-(thiazol-5-yl)-phenyl]-4(S)-hydroxy-2-N-(N-ethoxycarbonyl-(L)-valyl)amino-5(S)-N-(N-methoxycarbonyl-(L)-tert-leucyl)amino-6-phenyl-2-azahexane;

1-[4-(thiazol-5-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane;

1-[4-(thiazol-5-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane;

1-[4-(thiazol-2-yl)-phenyl]-4(S)-hydroxy-5(S)-2,5-bis-[N-(N-methoxycarbonyl-(L)-tert-leucyl)amino]-6-phenyl-2-azahexane;

1-[4-(thiazol-2-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane;

1-[4-(thiazol-2-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane;

1-[4-(2-methyl-2H-tetrazol-5-yl)-phenyl]-4(S)-hydroxy-5(S)-2,5-bis-[N-(N-methoxycarbonyl-(L)-tert-leucyl)amino]-6-phenyl-2-azahexane;

1-[4-(pyridin-2-yl)-phenyl]-4(S)-hydroxy-5(S)-2,5-bis-[N-(N-methoxycarbonyl-(L)-valyl)amino]-6-phenyl-2-azahexane;

1-[4-(pyridin-2-yl)-phenyl]-4(S)-hydroxy-5(S)-2,5-bis-[N-(N-methoxycarbonyl-(L)-tert-leucyl)amino]-6-phenyl-2-azahexane;

1-[4-(pyridin-2-yl)-phenyl]-4(S)-hydroxy-2-N-(N-methoxycarbonyl-(L)-valyl)amino-5(S)-N-(N-methoxycarbonyl-(L)-tert-leucyl)amino-6-phenyl-2-azahexane; or 1-[4-(thiazol-5-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane.

Special preference is given to the compounds of formula I mentioned in the Examples, or to pharmaceutically acceptable salts thereof provided that at least one salt-forming group is present.

The compounds of formula I and salts of those compounds having at least one salt-forming group are prepared according to processes known per se, for example as follows:

a) a hydrazine derivative of formula (III)

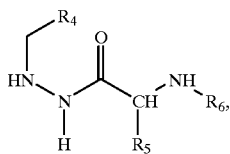

wherein the radicals $R_4$, $R_5$ and $R_6$ are as defined for compounds of formula I, is added to an epoxide of formula IV*, (IV*)

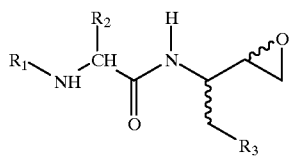

especially of formula IV, (IV)

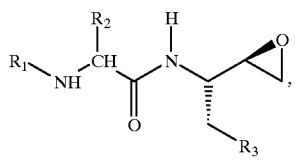

wherein the radicals $R_1$, $R_2$ and $R_3$ are as defined for compounds of formula I, free functional groups with the exception of those participating in the reaction being, if necessary, in protected form, and any protecting groups are removed, or b) an amino compound of formula V*, (V*)

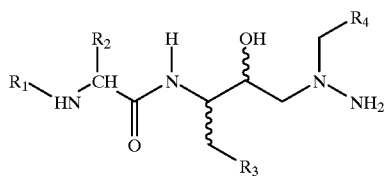

especially of formula V (V)

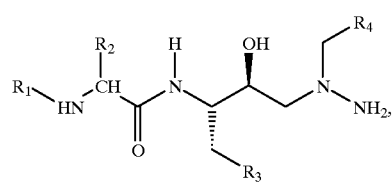

wherein the radicals $R_1$, $R_2$, $R_3$ and $R_4$ are as defined for compounds of formula I, is condensed with an acid of formula (VI)

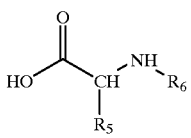

or with a reactive acid derivative thereof, wherein the radicals $R_5$ and $R_6$ are as defined for compounds of formula I, free functional groups with the exception of those participating in the reaction being, if necessary, in protected form, and any protecting groups are removed, or c) an amino compound of formula VII*, (VII*)

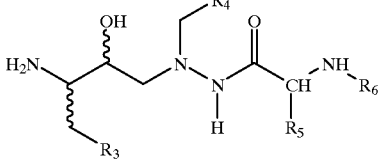

especially of formula VII (VII)

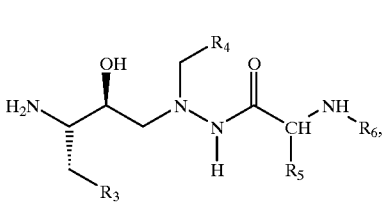

wherein the radicals $R_3$, $R_4$, $R_5$ and $R_6$ are as defined for compounds of formula I, is condensed with an acid of formula (VIII)

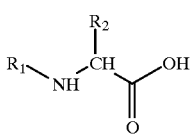

or with a reactive acid derivative thereof, wherein $R_1$ and $R_2$ are as defined for compounds of formula I, free functional groups with the exception of those participating in the reaction being, if necessary, in protected form, and any protecting groups are removed, or d) to prepare a compound of formula I wherein the pairs of substituents $R_1$ and $R_6$ and $R_2$ and $R_5$ are in each case two identical radicals, as defined for compounds of formula I, and $R_3$ and $R_4$ are as defined for compounds of formula I, a diamino compound of formula IX* especially of formula IX,

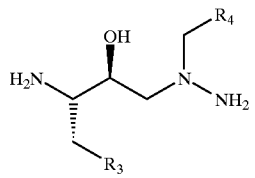

(IX)

wherein the radicals are as just defined, is condensed with an acid of formula

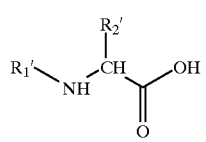

(VIIIa)

or with a reactive acid derivative thereof, wherein $R_1'$ and $R_2'$ are as defined for $R_1$ and $R_6$ and for $R_2$ and $R_5$, respectively, in formula I, the pairs $R_1$ and $R_6$ and $R_2$ and $R_5$ being in each case two identical radicals, free functional groups with the exception of those participating in the reaction being, if necessary, in protected form, and any protecting groups are removed, or e) an imino compound of formula (I')*,

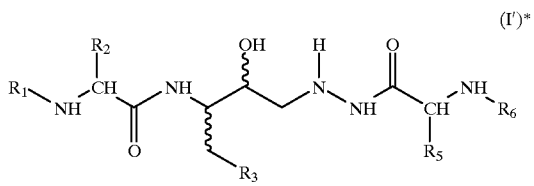

(I')* especially of formula I'

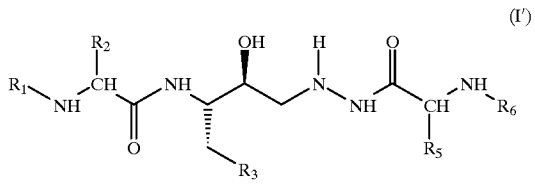

(I')

wherein the radicals $R_1$, $R_2$, $R_3$, $R_5$ and $R_6$ are as defined for compounds of formula I, is reacted with a compound of formula X,

(X)

wherein X is a leaving group and $R_4$ is as defined for compounds of formula I, free functional groups with the exception of those participating in the reaction being, if necessary, in protected form, and any protecting groups are removed, or f) an imino compound of formula (I')*,

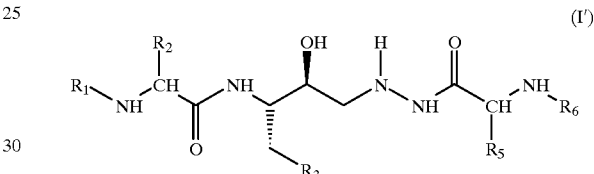

(I')* especially of formula I'

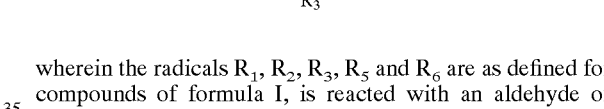

(I')

wherein the radicals $R_1$, $R_2$, $R_3$, $R_5$ and $R_6$ are as defined for compounds of formula I, is reacted with an aldehyde of formula X*,

(X*)

wherein $R_4$ is as defined for compounds of formula I, or with a reactive derivative thereof, with reductive alkylation, free functional groups with the exception of those participating in the reaction being, if necessary, in protected form, and any protecting groups are removed, and, if desired, a compound of formula I having at least one salt-forming group obtainable in accordance with any one of processes a) to f) above is converted into its salt or an obtainable salt is converted into the free compound or into a different salt and/or isomeric mixtures which may be obtainable are separated and/or a compound of formula I according to the invention is converted into a different compound of formula I according to the invention.

The above processes are described in more detail below with reference to preferred embodiments.

In the following description of the individual processes and the preparation of the starting materials, unless otherwise indicated the radicals $R_1$, $R_2$, $R_3$, $R_4$, $R_5$ and $R_6$ are as defined for compounds of formula I, preference being given in each case to the definitions given as being preferred.

Process a) (Addition of an amine to an epoxide):

In the hydrazine derivatives of formula III, the amino group participating in the reaction preferably has a free hydrogen atom; it may, however, itself have been derivatised in order to increase the reactivity of the hydrazine derivative.

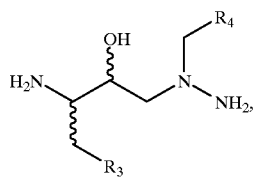

(IX*)

The epoxide of formula IV enables the terminal addition of the hydrazine derivative to proceed preferentially.

In starting materials, functional groups the reaction of which is to be avoided, especially carboxy, amino and hydroxy groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis and the like. In certain cases the protecting groups can additionally cause reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions. Radicals analogous to protecting groups may also be present in the end products, however. Compounds of formula I having protected functional groups may have greater metabolic stability or pharmacodynamic properties that are better in some other way than the corresponding compounds having free functional groups. Hereinabove and hereinbelow, protecting groups are referred to in their true sense when the radicals in question are not present in the end products.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie" ("Methods of Organic Chemistry"), Houben-Weyl, 4th edition, Volume 15/1, Georg Thieme Verlag, Stuttgart 1974, in H. D. Jakubke and H. Jescheit, "Aminosäauren, Peptide, Proteine" ("Amino acids, peptides, proteins"), Verlag Chemie, Weinhem, Deerfield Beach and Basle 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be cleaved selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or tri-substituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butylmethylsilyl)-ethoxycarbonyl, or 2-triarylsilylethoxycarbonyl, such as triphenylsilylethoxycarbonyl.

A carboxy group may also be protected in the form of an organic silyloxycarbonyl group. An organic silyloxycarbonyl group is, for example, a tri-lower alkylsilyloxycarbonyl group, for example trimethylsilyloxycarbonyl.

A protected carboxy group is preferably tert-lower alkoxycarbonyl, for example tert-butoxy-carbonyl, benzyloxycarbonyl, 4-nitrobenzyloxycarbonyl, 9-fluorenylmethoxycarbonyl or diphenylmethoxycarbonyl.

A protected amino group may be protected by an amino-protecting group, for example in the form of an acylamino, arylmethylamino, etherified mercaptoamino, 2-acyl-lower alk-1-enylamino or silylamino group, or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are, for example, lower alkanoyl, such as formyl, acetyl, propionyl or pivaloyl, halo-lower alkanoyl, for example 2 -haloacetyl, such as 2-chloro, 2-bromo, 2-iodo, 2,2,2-trifluoro- or 2,2,2-trichloro-acetyl, unsubstituted or substituted, for example halo-, lower alkoxy- or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl) methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, or triarylsilyl-lower alkoxycarbonyl, for example 2-triphenylsilylethoxycarbonyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino, or very especially 1-aryl-lower alkylmethylamino wherein the lower alkyl radical is preferably branched in the 1-position, such as in 1-methyl-1-phenyl-ethylamino. In an etherified mercaptoamino group the mercapto group is especially in the form of substituted arylthio or aryl-lower alkylthio wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of formula I. Compounds having such protecting groups can be prepared, for example using the corresponding chlorosilanes, such as dimethylchlorosilane, as silylating agents.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl, 1-methyl-1-phenyl-ethyl and lower alkoxycarbonyl-lower alk-1-en-2-yl.

A hydroxy group can be protected, for example, by an acyl group, for example lower alkanoyl that is substituted by halogen, such as chlorine, such as 2,2-dichloroacetyl, or especially by an acyl radical of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl, triisopropylsilyl or tert-butyl-di-methylsilyl, a readily removable etherifying group, for example an alkyl group, such as tert-lower alkyl, for example tert-butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, such as 2-tetrahydrofuryl or 2-tetrahydropyranyl, or a corresponding thia analogue, and also by 1-phenyl-lower alkyl, such as benzyl, diphenylmethyl or trityl, wherein the phenyl radicals can be substituted, for example, by halogen, for example chlorine, lower alkoxy, for example methoxy, and/or by nitro.

A hydroxy group and an amino group that are adjacent to one another in a molecule can be protected, for example, by bivalent protecting groups, such as a methylene group that is preferably substituted, for example by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

In the context of this disclosure, a protecting group, for example a carboxy-protecting group, is to be understood as being expressly also a polymeric carrier that is bonded in a readily removable manner to the functional group, for example the carboxy group, to be protected, for example a carrier suitable for the Merrifield synthesis. Such a suitable polymeric carrier is, for example, a polystyrene resin weakly cross-linked by copolymerisation with divinylbenzene and carrying bridge members suitable for reversible bonding.

The addition of the compounds of formula III to the epoxides of formula IV is carried out preferably under the reaction conditions customarily used for the addition of nucleophiles to epoxides.

The addition is carried out especially in aqueous solution and/or in the presence of polar solvents, such as alcohols, for example methanol, ethanol, isopropanol or ethylene glycol, ethers, such as dioxane, amides, such as dimethylformamide, or phenols, such as phenol, and also under anhydrous conditions, in non-polar solvents, such as benzene or toluene, or in benzene/water emulsions, optionally in the presence of acidic or basic catalysts, or example alkali hydroxide solutions, such as sodium hydroxide solution, or in the presence of solid phase catalysts doped with the hydrazine, such as aluminium oxide, in ethers, for example diethyl ether, generally at temperatures of from approximately 0° C. to the boiling temperature of the reaction mixture in question, preferably from 20° C. to reflux temperature, optionally under elevated pressure, for example in a bomb tube, in which case it is also possible to exceed the boiling temperature measurable at normal pressure, and/or under an inert gas, such as nitrogen or argon, it being possible for each of the two compounds of formulae III and IV to be present in excess, for example in a molar ratio of from 1:1 to 1:100, especially in a molar ratio of from 1:1 to 1:10, more especially in a ratio of from 1:1 to 1:3.

The freeing of protected groups may be effected in accordance with the methods described below under the heading "removal of protecting groups".

Process b) (Formation of an amide bond)

In starting materials of formulae V and VI, functional groups, with the exception of groups that are to participate in the reaction or that do not react under the reaction conditions, are protected independently of one another by one of the protecting groups mentioned under Process a).

The compounds of formula VI either contain a free carboxy group or are in the form of a reactive acid derivative thereof, for example in the form of a derived activated ester or reactive anhydride, or in the form of a reactive cyclic amide. The reactive acid derivatives may also be formed in situ.

Activated esters of compounds of formula VI having a terminal carboxy group are especially esters unsaturated at the carbon atom linking the radical to be esterified, for example esters of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxy-acetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide or especially N-(3-dimethylaminopropyl)-N'-ethylcarbodiimide; carbodiimide method), or N,N-substituted amidino esters (obtainable, for example, by treatment of the corresponding acid with an N,N-disubstituted cyanamide; cyanamide method), suitable aryl esters, especially phenyl esters suitably substituted by electron-attracting substituents (obtaining, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, or example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride, phosgene or oxalyl chloride; acid chloride method), azides (obtainable, for example, from a corresponding acid ester via the corresponding hydrazide and treatment thereof with nitrous acid; azide method), anhydrides with carbonic acid semi-esters, for example carbonic acid lower alkyl semiesters (especially chloroformic acid methyl esters) (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydride with dihalogenated, especially dichlorinated, phosphroc acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

As mentioned, derivatives of carboxylic acids used as acylating agents may also be formed in situ. For example, N,N'-disubstituted amidino esters may be formed in situ by reacting a mixture of the starting material of formula V and the acid used as acylating agent in the presence of a suitable N,N'-disubstituted carbodiimide, for example N,N'-cyclohexylcarbodiimide or specially N-(3-dimethylaminopropyl)-N'-ethylcarbodiimide. In addition, amino or amido esters of the acids used as acylating agents may be formed in the presence of the starting material of formula V to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, where appropriate in the presence of a suitable base, for example 4-dimethylamino-pyridine. Furthermore, activation in situ can be achieved by reaction with N,N,N',N'-tetraalkyluronium compounds, such as O-benzotriazol-1-yl-N,N,N',N'-tetramethyluronium hexafluorophosphate, O-(1,2-dihydro-2-oxo-1-pyridyl)-N,N,N',N'-tetramethyluronium tetrafluoroborate (in the presence or absence of 1,8-diazabicyclo[5.4.0]-undec-7-ene(1,5—5)) or O-(3,4-dihydro-4-oxo-1,2,3-benzotriazolin-3-yl)-N,N,N',N'-tetramethyluronium tetrafluoroborate. Finally, phosphoric acid anhydrides of the carboxylic acids for formula VI can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yl-oxy-tris(dimethylamino) phosphonium hexafluoride, preferably in the presence of a racemisation-reducing additive, such as N-hydroxybenzotriazole.

The amino group of compounds of formula V that participates in the reaction preferably carries at least one reactive hydrogen atom, especially when the carboxy, sulfonyl or phosphoryl group reacting therewith is present in reactive form; it may, however, itself have been derivatised, for example by reaction with a phosphite, such as diethylchlorophosphite, 1,2-phenylene chlorophosphite, ethyldichlorophosphite, ethylene chlorophosphite or tetraethylpyrosphosphite. A derivative of such a compound having an amino group is, for example, also a carbamic acid halide or an isocyanate, the amino group that participates in the reaction being substituted by halocarbonyl, for example chlorocarbonyl, or modified in the form of an isocyanate group, respectively.

Condensation to form an amide bond can be carried out in a manner known per se, for example as described in standard works, such as Houben-Weyl, "Methoden der organischen Chemie", 4th edition, Volume 15/II (1974), Volume IX (1955), Volume E11 (1985), Georg Theme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the appropriate amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl- or dicyclohexyl-carbodiimide or especially N-(3-dimethylaminopropyl)-N'-ethylcarbodiimide, also suitable carbonyl compounds, for example carbonylimidazole, 1,2-oxazolium compounds, for example 2-ethyl-5-phenyl-1,2-oxazolium-3'-sulfonate and 2-tert butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotrial-1-yl-N,N,N',N'-tetramethyluronium hexafluorophosphate or especially O-(1,2-dihydro-2-oxo-1-pyridyl)-N,N,N',N'-tetramethyluronium tetrafluoroborate (in the presence or absence of 1,8-diazobicyclo[5.4.0]undec-7-ene-(1,5—5)), also activated phosphoric acid derivatives, for example diphenylphosphorylazide, dethylphosphorylcycanide, phenyl-N-phenylphosphoroamidochloridate, bis(2-oxo-3-oxazolidinyl)phosphinic acid chloride or 1-benzotriazolyloxy-tris (dimethylamino) phosphonium hexafluorophosphate.

If desired, an organic base is added, preferably a tertiary amine, for example a tri-lower alkylamine, especially ethyldiisopropylamine or more especially triethylamine, and/or a heterocyclic base, for example 4- dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such ass sodium or potassium carbonate or hydrogen carbonate (if desired together with a sulfate).

Carboxylic acid chlorides, for example the chlorocarbonic acid derivatives derived from the acid of formula VI, are condensed with the corresponding amines preferably in the presence of an organic amine, for example the above-mentioned tri-lower alkylamines or heterocyclic bases, where appropriate in the presence of a hydrogen sulfate or a hydroxide, preferably an alkali metal hydroxide, such as sodium hydroxide.

The condensation is preferably carried out in an inert, aprotic, preferably anhydrous, solvent or solvent mixture, for example in a carboxylic acid amide, for example formamide or di-methylformamide, a halogenated hydrocarbon, for example methylene chloride, carbon tetrachloride or chlorobenzene, a ketone, for example acetone, a cyclic ether, for example tetrahydrofuran or dioxane, an ester, for example ethyl acetate, or a nitrile, for example acetonitrile, or in a mixture thereof, as appropriate at reduced or elevated temperature, for example in a temperature range of from approximately −40° to approximately +100° C., preferably from approximately 31 10° to approximately +70° C., and when arylsulfonyl esters are used also at approximately from +100° to +200° C., especially at temperatures of from 10° to 30° C., and if necessary under an inert gas atmosphere, for example a nitrogen or argon atmosphere.

Aqueous, for example alcoholic, solvents, for example ethanol, or aromatic solvents for example benzene or toluene, may also be used. When alkali metal hydroxides are present as bases, acetone may also be added where appropriate.

The condensation can also be carried out in accordance with the technique known as solid-phase synthesis which originates from R. Merrifield and is described, for example, in Agnew. Chem. 97, 801–812 (1985) Naturwissenschaften 71, 252–258 (1984) or in R. A. Houghten, Proc. Natl. Acad. Sci. USA 82, 5131–5135 (1985).

The freeing of protected groups may be effected in accordance with the methods described below under the heading "Removal of protecting groups".

Process c) (Formation of an amide bond).

In starting materials of formulae VII and VIII, functional groups, with the exception of groups that are to participate in the reaction or tat do not react under the reaction conditions, are protected independently of one another by one of the protecting groups mentioned under Process a).

The process is entirely analogous to that given under Process b) but compounds of formula VII are used instead of those of formula V and compounds of formula VIII are used instead of those of formula VI.

The freeing of protected groups may be effected in accordance with he the methods described below under the heading "Removal of protecting groups".

Process d) (Formulation of an amide bond)

In starting materials of formula IX and in the acid of formula VIIIa suitable for the introduction of the identical acyl radicals, or in reactive derivatives thereof, functional groups that are not to participate in the reaction or that do not react under the reaction conditions, are protected independently of one another by one of the protecting groups mentioned under Process a).

Preferred starting compounds of formula IX, which may be protected by protecting groups, are those of formula II described below in the section relating to starting compounds.

The process is entirely analogous to that given under Process b) but compounds of formula IX are used instead of those of formula V and compounds of formula VIIIa are used instead of those of formula VI.

The freeing of protected groups may be effected in accordance with the methods described below under the heading "Removal of protecting groups".

Process e) (Alkylation of a secondary nitrogen atom)

In starting materials of formula I' and formula X or in reactive derivatives thereof, functional groups that are not to participate in the reaction or that do not react under the reaction conditions, are protected independently of one another by one of the protecting groups mentioned under Process a).

A leaving group X is especially a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, hydroxy esterified by a strong organic sulfonic acid, such as a lower alkanesulfonic acid that is unsubstituted or substituted, for example, by halogen, such as fluorine, or by an aromatic sulfonic acid, for example benzenesulfonic acid that is unsubstituted or substituted by lower alkyl, such as methyl, halogen, such as bromine, and/or by nitro, for example a methane-sulfonic, p-bromotoluenesulfonic or p-toluenesulfonic acid, and hydroxy esterified by hydrazoic acid.

The substitution can take place under the conditions of a first or second order nucleophilic substitution.

For example, one of the compounds of formula X wherein X is a leaving group having high polarisability of the electron shell, for example iodine, can be used in a polar aprotic solvent, for example acetone, acetonitrile, nitromethane, dimethyl sulfoxide or dimethylformamide. The reaction can also be carried out in water, optionally in admixture with an organic solvent, for example ethanol, tetrahydrofuran or acetone, as solubiliser. The substitution reaction is carried out, as appropriate, at reduced or elevated temperature, for example in a temperature range of from approximately −40° to approximately 100° C., preferably from approximately −10° to approximately 50° C., and if necessary under an inert gas, for example under a nitrogen or argon atmosphere.

Process e) is not successful in all cases, is often possible only under special conditions and is therefore a less preferred process.

The freeing of protected groups may be effected in accordance with the methods described below under the heading "Removal of protecting groups".

Process f) (Reductive alkylation of a secondary amino group)

In starting materials of formula I' and formula X* or in reactive derivatives thereof, functional groups that are not to participate in the reaction or that do not react under the reaction conditions, are protected independently of one another by one of the protecting groups mentioned under Process a).

Reactive derivatives of the compounds of formula I are, for example, corresponding bisulfite adducts or especially semiacetals or ketals of compounds of formula X* with alcohols, for example lower alkanols; or thioacetals of compounds of formula X* with mercaptans, for example lower alkanesulfides. The free aldehydes of formula X* are preferred.

The reductive alkylation is preferably carried out with hydrogenation in the presence of a catalyst, especially a noble metal catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkanecarboxylic acids or especially a sulfonic acid, such as p-toluenesulfonic acid; in customary solvents, for example alcohols, such as methanol or ethanol, or ethers, for example cyclic ethers, such as tetrahydrofuran, in the presence or absence of water.

The freeing of protected groups may be effected in accordance with the methods described below under the heading "Removal of protecting groups".

Removal of protecting groups

The removal of protecting groups that are not constituents of the desired end product of formula I, for example carboxy-, amino- and hydroxy-protecting groups, is effected in a manner known per se, for example by means of solvolysis, especially hydrolysis, alcoholysis or acidolysis, or by means of reduction, especially hydrogenolysis or chemical reduction, and also photolysis, stepwise or simultaneously as appropriate, it being possible also to use enzymatic methods. The removal of the protecting groups is described, for example, in the standard works mentioned hereinabove in the section relating to protecting groups.

For example, protected carboxy, for example tert-lower alkoxycarbonyl, lower alkoxy-carbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can be freed from lower alkoxy-carbonyl also by bases, such as hydroxides, for example alkali metal hydroxides, such as NaOH or KOH. Unsubstituted or substituted benzyloxycarbonyl can be cleaved, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycol acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxylcarbonyl can also be converted into free carboxy. Aroylmethoxycarbonyl can be cleaved also by treatment with a nucleophilic, preferably salt-forming, reagent, such as sodium thiophenolate or sodium iodide. 2-(Tri-substituted silyl)-lower alkoxycarbonyl, such as 2- tri-lower alkylsilyl-lower alkoxycarbonyl, can also be converted free carboxy by treatment with a salt of hydrofluoric acid that yields the fluoride anion, such as an alkali metal fluoride, for example sodium or potassium fluoride, where appropriate in the presence of a macrocylic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be cleaved enzymatically, for example by means of esterases or suitable pepidases, for example using trypsin.

A protected amino group is freed in a manner known per se and, according to the nature of the protecting groups, in various ways, preferably by solvolysis or reduction. Lower alkoxy-carbonylamino, such as tert-butoxycarbonylamino, can be cleaved in the presence of acids, for example mineral acids, for example a hydrogen halide, such as hydrogen chloride or hydrogen bromide, or sulfuric or phosphoric acid, but preferably hydrogen chloride, or in the presence of strong organic acids, such as a trihaloacetic acid, for example trifluoroacetic acid, or formic acid, in the presence of absence of polar solvents, such as water, or ethers, preferably cyclic ethers, such as dioxane; or nitriles, such as acetonitrile, 2-halo-lower alkoxycarbonylamino (where appropriate after conversion of a 2-bromo-lower alkoxycarbonylamino group into a 2-iodo-lower alkoxycarbonylamino group), or, dissolved directly in a liquid organic carboxylic acid, such as formic acid, aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxy-carbonylamino also by treatment with an alkali metal dithionite, for example sodium dithionite. Unsubstituted or substituted diphenylmethoxycarbonylamino, tert-lower alkoxycarbonylamino or 2- (tri-substituted silyl)-lower alkoxycarbonylamino, such as 2-tri-lower alkylsilyl-lower alkoxycarbonylamino, can be cleaved by treatment with a suitable acid, for example formic acid or trifluoroacetic acid; unsubstituted or substituted benzyloxycarbonyl-amino can be cleaved, for example, by means of hydrogenolysis, i.e. by treatment with hydrogen in the presence of a suitable hydrogenation catalyst, such as a platinum or palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water, and an amino group protected in the form of silylamino can be freed, for example, by means of hydrolysis or alcoholsis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis; such as alcoholysis or hydrolysis, of the resulting substitution product. Amino is freed from trifluoroacetylamino, for example, by hydrogenolysis with bases, such as alkali metal hydroxides or carbonates, such as $Na_2CO_3$ or $K_2CO_3$, in polar solvents, for example alcohols, such as methanol, in the presence or absence of water, at temperatures of from 0° to 100° C., especially at reflux temperature. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. A 1-aryl-lower alkylmethyl protecting group wherein the lower alkyl radical is preferably branched i the 1-position, such as 1-methyl-1-phenyl-ethyl, can be removed especially in the presence of a strong acid, such as sulfuric acid (e.g. 80% sulfuric acid) in aqueous solution, at preferred temperatures of from −10° to 30° C., especially at approximately 0° C.

Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy group protected by a suitable acyl group, by a tri-lower alkylsilyl group or by unsubstituted or substituted 1-phenyl-lower alkyl is freed analogously to a correspondingly protected amino group. A hydroxy group protected by 2,2-dichloroacetyl is freed, for example, by basic hydrolysis, and a hydroxy group protected by tert-lower alkyl or by a 2,-oxa- or 2-thia-aliphatic or -cycloaliphatic hydrocarbon radical is freed by acidolysis, for example by treatment with a mineral acid or a strong carboxylic acid, for example trifluoroacetic acid. Adjacent hydroxy and amino groups that are protected together by a bivalent protecting group, preferably, for example, by a methylene group mono- or di-substituted by lower alkyl, such as by lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid. 2-Halo-lower alkoxycarbonyl is removed using the above-mentioned reducing agents, for example a reducing metal, such as zinc, reducing metal salts, such as chromium(II) salts, or using sulfur compounds, for example sodium dithionite or especially sodium sulfide and carbon disulfide.

When several protected functional groups are present, if desired the protecting groups can be so selected that more than one such group can be removed simultaneously, for example by removal of trifluoroacetyl as amino-protecting group by base catalysis, for example with $K_2CO_3$ in methanol/water, and later removal of tert-butoxycarbonyl as amino-protecting group, for example with HCl in dioxane or acetonitrile (in the presence or absence of water) or with formic acid, or selective removal of 1-phenyl-ethyl as amino-protecting group using sulfuric acid; or generally by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather in a desired sequence, the corresponding intermediates being obtained.

Additional Process Steps

In the additional process steps, which are optional, functional groups of the starting compounds that are not to participate in the reaction may be unprotected or may be in protected form, for example they may be protected by one or more of the protecting groups mentioned above under Process a). The protecting groups may be retained in the end products or some or all of them may be removed in accordance with one of the methods mentioned under the heading "Removal of protecting groups".

Salts of compounds of formula I having a salt-forming group can be prepared in a manner known per se. For example, acid addition salts of compounds of formula I can be obtained, for example, by treatment with an acid or a suitable anion exchange reagent.

Salts can be converted into the free compounds in customary manner, for example by treatment with a suitable basic agent.

Stereoisomeric mixtures, for example mixtures of diastereoisomers, can be separated into the corresponding isomers in a manner known per se by suitable separating procedures. For example, mixtures of diastereoisomers can be separated into the individual diastereoisomers by fractional crystallization, chromatography, solvent partitioning and the like. Such separation can be carried out either at the stage of one of the starting materials or with the compounds of formula I themselves.

In a compound of formula I wherein $R_2$ is phenyl, that phenyl radical can be hydrogenated, for example by catalytic hydrogenation, especially in the presence of heavy metal oxides, such as rhodium/platinum mixed oxides, for example with the Nishimura catalyst, preferably in a polar solvent, such as an alcohol, for example methanol or ethanol, at temperatures of from 0° to 80° C., especially from 10° to 40° C., and at a preferred hydrogen pressure of from 1 to 10 atm, preferably at about normal pressure.

In a compound of formula I wherein $R_4$ is 4-tetrazol-5-ylphenyl, a lower alkyl group, for example methyl, can be converted by reaction with a lower alkyl halide or a lower alkyl-arylsulfonate, such as a lower alkyl iodide or a lower alkyltoluenesulfonate, for example methyl iodide or tert-butyl iodide, preferably in the presence of caesium carbonate in a mixture of a cyclic ether, such as dioxane, and an N,N-di-lower alkyl-lower alkylanecarboxylic acid amide, such as dimethylformamide, at preferred temperatures of from −10° to 40° C., especially from 0° to about 30° C.

In a compound of formula I wherein $R_4$ is 4-(1- or 2-phenyl-lower alkyl, such as 1- or 2- (1-methyl-1-phenylethyl)-tetrazol-5-yl) phenyl, the phenyl-lower alkyl radical (preferably 1-methyl-1-phenylethyl) can be removed by treatment with a strong mineral acid, such as sulfuric acid, in aqueous solution, preferably at temperatures of from −20° to 30° C., for example at 0° C.

General process conditions

All the process steps given in this text can be carried out under reaction conditions known per se, but preferably under those specifically mentioned, in the absence or usually in the presence of solvents or diluents, preferably those solvents or diluents that are inert towards the reagents used and are solvents therefor, in the absence or presence of catalysts, condensation agents or neutralising agents, for example ion exchangers, such as cation exchangers, for example in the H⁺ form, depending upon the nature of the reaction and/or the reactants at reduced, normal or elevated temperature, for example in a temperature range of from approximately −100° to approximately 190° C., preferably from approximately −80° to approximately 150° C., for example from −80° to −60° C., at room temperature, at from −20° to 40° C. or at the boiling point of the solvent used, under atmospheric or in a closed vessel, optionally under pressure, and/or in an inert atmosphere, for example under an argon or nitrogen atmosphere.

In the case of all starting materials and intermediates, salts may be present when salt-forming groups are present. Salts may also be present during the reaction of such compounds, provided that the reaction will not be affected.

In all reaction steps, any isomeric mixtures that are formed can be separated into the individual isomers, for example diastereoisomers or enantiomers, or into any desired mixtures of isomers, for example racemates or diastereosomeric mixtures, for example analogously to the methods described under the heading "Additional process steps".

In certain cases, for example in the case of hydrogenation, it is possible to carry out stereo-selective reaction is so that, for example, individual isomers may be obtained more easily.

The solvents from which those suitable for a particular reaction can be selected include, for example, water, esters, such as lower alkyl-lower alkanoates, for example diethyl acetate, ethers, such as aliphatic ethers, for example diethyl ether, or cyclic ethers, for example analogously to the methods described under the heading "Additional process steps".

In certain cases, for example in the case of hydrogenation, it is possible to carry out stereo-selective reactions so that, for example, individual isomers may be obtained more easily.

The solvents from which those suitable for a particular reaction can be selected include, for example, water, esters, such as lower alkyl-lower alkanoates, for example diethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformadide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless the description of the processes indicates otherwise. Such solvent mixtures can also be used in working-up, for example by chromatography or partitioning.

The invention relates also to those forms of the process in which a compound obtainable as intermediate at any stage is used as starting material and the remaining steps are carried out or in the process is interrupted at any stage or a starting material is formed under the reaction conditions or is used in the form of a reactive derivative or salt, or a compound obtainable in accordance with the process of the invention is produced under the process conditions and further processed in situ, it being preferable to use those starting materials which result in the compounds described above as being preferred, especially those described as being especially preferred, more especially preferred and/or very especially preferred.

The preparation of compounds of formula I is preferably carried out analogously to the processes and process steps given in the Examples.

The compounds of formula I, including their salts, may also be obtained in the form of hydrates, or their crystals may include, for example, the solvent used for crystallization.

Pharmaceutical compositions

The invention relates also to pharmaceutical compositions comprising compounds of formula I*, which means especially a compound of the formula I, and most especially of formula Ia.

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carriers.

The invention relates also to a pharmaceutical composition suitable for administration to a warm-blooded animal, especially a human being, for the treatment or prevention of a disease that is responsible to inhibition of a retroviral protease, especially a retroviral aspartate protease, such as HIV-1 or HIV-II gag protease, for example a retroviral disease, such as AIDS or its preliminary stages, comprising a compound of formula I*, or a pharmaceutically acceptable salt thereof, in an amount effective in the inhibition of the retroviral protease, together with at least one pharmaceutically acceptable carrier.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The invention relates also to a method of treating diseases caused by viruses, especially by retroviruses, especially AIDS or its preliminary stages, wherein a therapeutically effective amount of a compound of formula I* or a pharmaceutically acceptable salt thereof is administered in a dose that is effective in the treatment of said disease especially to a warm-blooded animal, for example a human being, who on account of one of the mentioned diseases, especially AIDS or its preliminary stages, requires such treatment. The preferred dose to be administered to warm-blooded animals, for example human beings of approximately 70 kg body weight, is from approximately 3 mg to approximately 3 g, preferably from approximately 10 kg body weight, is from approximately 1.5 g, for example approximately from 50 mg to 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotoric aqueous solutions or suspensions, are preferably used, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, or acids, for example citric acid, and are prepared in a manner known per se, for example by means of conventional dissolving lyophilising processes. The said solutions or suspensions may comprise viscosity-increasing substances, such as sodium carboxymethylcellulose, carboxymethylcellulose, hydroxypropylmethylcellulose (e.g. cellulose HPM603), silica gel, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E. β-cartotene or 3,5-di-tert-butyl-4-hydroxytoluene. The alcohol component of those fatty acid esters has a maximum of 6 carbon atoms and is a mono-or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, soybean oil and more especially groundnut oil and sesame oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for the active ingredients to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxy-methyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phtalate or hydroxypropylmethylcellulose phthalate.

Capsules are hard gelatin capsules and also soft, sealed capsules made of gelatin and a plasticiser, such as glycerol or sorbitol. The hard gelatin capsules may comprise the active ingredient in the form of granules, for example with fillers, such as lactose, binders, such as starches, and/or glidants, such as talc or magnesium stearate, and if desired with stabilisers. In capsules the active ingredient is preferably dissolved or suspended in suitable oily excipients, such as fatty oils, paraffin oil or liquid polyethylene glycols, it likewise being possible for stabilisers and/or antibacterial agents to be added. There may be mentioned as such oils especially liquid fatty acid esters that contain as acid component a long-chained fatty acid, for example having from 8 to 22, especially from 12 to 22, carbon atoms, for example lauric acid, tridecylic acid, myristic acid, pentadecylic acid, palmitic acid, marganic acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxy-toluene. The alcohol component of those fatty acid ester has a maximum of 6 carbon atoms and is a mono- or poly-hydric, for example a mono-, di- or tri-hydric, alcohol, for example methanol, ethanol, propanol, butanol or pentanol or the isomers thereof, but especially ethylene or propylene glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (tri-glyceride of saturated fatty acids with a chain length of $C_8$ to $C_{12}$, Hüls AG, Germany), but especially vegetable oils, such as cottonseed oil, almond oil, olive oil, castor oil, groundnut oil, soybean oil and more especially sesame oil. Paraffin oil is also possible. Stabilisers, such as emulsifiers, wetting agents or surfactants, binders, such as starch pastes using, for example, corn, wheat, rice or potato starch, gelatin, tragacanth, methylcellulose, hydroxypropylmethylcellulose or hydroxypropylcellulose (preferred), sodium carboxymethylcellulose, cyclodextrin(s) and/or polyvinylpyrrolidone, and/or antibacterial agents may be added. Suitable emulsifiers are especially oleic acid, non-loric surfactants of the fatty acid polyhydroxy alcohol ester type, such as sorbitan monolaurate, monoleate, monostearate or monopalmitate, sorbitan tristearate or trioleate, polyoxyethylene adducts of fatty acid-polyhydroxy alcohol esters, such as polyoxyethylene sorbitan monolaurate, mono-oleate, monostearate, monopalmitate, tristearate or trioleate, polyethylene glycol fatty acid esters, such as polyoxyethyl stearate, polyoxyethylene glycol (300 or 400) stearate, poly-ethylene glycol 2000 stearate, especially ethylene oxide/propylene oxide block polymers of the ®Pluronic type (Wyandotte Chem. Corp.; trade mark of BASF, FRG) or ®Synperonic type (ICI). For example, if the active ingredient is not soluble in the mentioned oils it is present in the form of a suspension, for example having a particle size of approximately from 1 to 100 mm. Such suspensions may also be used as such, that is to say without capsules.

Colourings or pigments may be added to the tablets or dragée coatings or to capsule walls, for example for identification purposes or to indicate different doses of active ingredient.

Starting materials

The present invention relates also to novel starting materials and/or intermediates and to processes for their preparation. The starting materials used and the reaction conditions selected are preferably those which result in the compounds described as being preferred.

In the preparation of all starting materials, free functional groups that are not to participate in the reaction in question may be unprotected or may be in protected form, for example they may be protected by the protecting groups mentioned above under Process a). Those protecting groups can be removed at suitable times by the reactions described under the heading "Removal of protecting groups".

The starting materials of Process a) are known or, if novel, can be prepared in accordance with processes known per se; for example the compounds of formula III can be prepared from hydrazine or suitable derivatives thereof, and the compounds of formula IV can be prepared from suitable amino acids or analogues thereof, for example having one of the mentioned side chains $R_3$.

The compounds of formula III can be obtained, for example, from compounds of formula

$$H_2N-NH-R_7 \qquad (XI),$$

which are known per se or can be prepared from hydrazine by the introduction of protecting groups as described under Process a) and in which $R_7$ is hydrogen or an amino-protecting group as described above under Process b), especially tert-lower alkoxycarbonyl, such as tert-butoxycarbonyl, aryl-lower alkoxycarbonyl, such as benzyloxycarbonyl or 9-fluorenyl-methoxycarbonyl, or one of the above-mentioned acylamino-protecting groups, especially trifluoroacetyl, by alkylation with a compound of formula X as described above under Process e), or by reaction of the radical of sub-formula

$$-R_4 \qquad (A)$$

wherein $R_4$ is as defined or compounds of formula I, by reaction of a suitable carbonyl compound of formula X*, or a reactive derivative thereof, both as defined under Process f), with the free amino group of the compound of formula IX or or an acylated derivative thereof and subsequent reduction of the resulting hydrazone to form a hydrazine derivative of formula

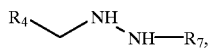

the radicals in all the mentioned compounds being as defined above and functional groups in the reagents involved that are not to participate in the reaction being protected as necessary, and removal of the protecting group $R_7$ as necessary and by condensation under the conditions mentioned above under Process b) with an acid of formula VI, or an acid derivative thereof mentioned under Process b).

The carbonyl compounds of formula X*, or reactive derivatives thereof, suitable for the introduction of the radical of sub-formula A that are used for the preparation of the compounds of formula XII, as defined above under Process f), are aldehydes or reactive derivatives thereof, the reactive carbonyl group of which, after the reaction with compounds of formula XI and the subsequent reduction, is a constituent of one of the mentioned radicals of sub-formula A.

The reaction of the carbonyl compounds with the compounds of formula XI to form the corresponding hydrazones is carried out under the conditions customarily used for the reaction of carbonyl compounds with amines, preferably in polar organic solvents, for example ethers, such as tetrahydrofuran or diethyl ether, alcohols, such as methanol or ethanol, carboxylic acid amides, such as dimethylformamide, or esters, such as ethyl acetate, or in aqueous solution, preferably in methanol, and also in the presence or absence of acid catalysts, for example carboxylic acids, such as formic acid or acetic acid, or sulfonic acids, such as p-toluenesulfonic acid, at temperatures of from 0° C. to the reflux temperature of the reaction mixture, preferably at temperatures of from 20° C. to the reflux temperature of the reaction mixture.

Compounds of formula

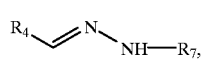

(XII*)

wherein $R_4$ and $R_7$ are as defined for compounds of formula XII are obtained.

The reduction of the resulting hydrazones of formula XII* is preferably carried out by hydrogenation in the presence of a suitable catalyst or with complex hydrides in the presence of acids. As catalysts suitable for hydrogenation there are used metals, such as nickel, iron, cobalt or ruthenium, or noble metals or oxides thereof, such as palladium or rhodium or oxides thereof, optionally, for example, applied to a suitable carrier, such as barium sulfate, aluminum oxide or carbon (active carbon) or in the form of skeleton catalysts, such as Raney nickel. Solvents customarily used for the catalytic hydrogenation are, for example, water, alcohols, such as methanol or ethanol, esters, such as ethyl acetate, ethers, such as dioxane, chlorinated hydrocarbons, such as dichloromethane, carboxylic acid amides, such as dimethylformamide, or carboxylic acids, such as glacial acetic acid, or mixtures of those solvents. The hydrogenation is carried out preferably at temperatures of from 10° to 250° C., especially from room temperature to 100° C., and preferably at hydrogen pressures of from 1 to 200 bar, especially from 1 to 10 bar, in the customary apparatus. For the reduction with complex hydrides, especially borohydrides, such as alkali metal cyanoborohydride, for example sodium cyanoborohydride, it is preferable to add weak acids, such as sulfonic acids, for example p-toluenesulfonic acid, or carboxylic acids, such as acetic acid, preferably in alcohols, such as methanol or ethanol, or mixtures thereof with water (see, for example, Tetrahedron 49, 8605–8628 (1993)).

It is also possible for compounds of formula XI to be alkylated by reduction directly with compounds of formula X*, or reactive derivatives thereof, as defined under Process f), under conditions analogous to those mentioned in Process f).

Also especially preferred for the preparation of compounds of formula XI are reaction conditions analogous to those described in J. Chem. Soc. Perkin I, 1712 (1975).

Compounds of formula III can also be obtained, for example, by reacting a compound of formula XII*, as defined above, wherein $R_7$ is hydrogen (obtainable, for example, by the removal of protecting groups when $R_7$ is a protecting group), directly, with condensation under the conditions mentioned above under Process b) with acids of formula VI, or the acid derivatives thereof mentioned under Process b), to form compounds of formula

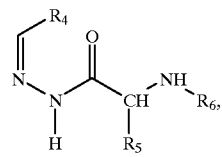

(III*)

wherein the radicals are as defined for compounds of formula I, which are then converted into compounds of formula III by reduction under conditions analogous to the conditions mentioned for the reduction of hydrazones of formula XII*.

Compounds of formula III* can also be obtained from the corresponding compounds of formula III', which are as defined as described below, by reacting the latter with compounds of formula X*, defined above, to form the hydrazones of formula III* under conditions analogous to those described above for the reaction of carbonyl compounds of formula X* with hydrazines of formula XI.

A compound of formula IV can be obtained, for example, by reduction of an amino acid of formula

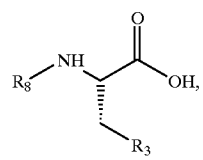

(XIII)

wherein $R_8$ is hydrogen or especially one of the amino-protecting groups mentioned under Process a), especially tert-lower alkoxycarbonyl, such as tert-butoxycarbonyl, aryl-lower alkoxycarbonyl, such as benzyloxycarbonyl or 9-fluorenylmethoxycarbonyl, or one of the acyl-amino-protecting groups mentioned under Process a), especially trifluoroacetyl, and $R_3$ is as defined for compounds of formula I, to form an aldehyde of formula

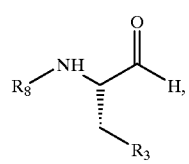

(XIV)

wherein the radicals are as last defined, subsequent reaction of that aldehyde with a ylid compound, preferably a sulfur ylid compound, to form an epoxide of formula

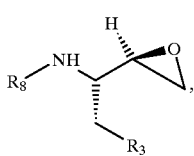

(XV)

wherein the radicals are as last defined, removal of the protecting group $R_8$ (the resulting free amino compound wherein $R_8$=hydrogen may be stable, for example in the form of an acid addition salt) and finally acylation of the amino group of the resulting compound with an acid of formula VIII, wherein the radicals are as defined for formula VIII, under suitable conditions analogous to the conditions described for Process b).

The reduction of amino acid of formula XIII to the corresponding aldehydes of formula XIV is carried out, for example, by reduction to the corresponding alcohols and subsequent oxidation to the mentioned aldehydes.

The reduction to the alcohols (a free compound or (if necessary after the introduction of protecting groups, as described under Process a)) a compound N-protected by $R_8$, having the formula

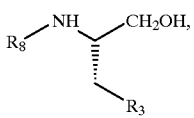

(XIII*)

wherein the radicals are as defined for compounds of formula XIII) is carried out, for example, by hydrogenation of the acid halides or other activated carboxylic acid derivatives mentioned under Process b) under the conditions mentioned for the hydrogenation of hydrazones obtained from compounds of formula XII, with diborane or with complex hydrides, such as sodium borohydride. The subsequent oxidation of the resulting alcohols is possible, for example, by oxidation of the hydroxy group with a sulfoxide, such as dimethyl sulfoxide, in the presence of a reagent that activates the hydroxy group, such as a carboxylic acid chloride, for example oxalyl chloride, in inert solvents, for example a halogenated hydrocarbon, such as dichloromethane, and/or an acyclic or cyclic ether, such as tetrahydrofuran, at from −80° to 0° C., for example form −78° to −50° C., or by oxidation, for example, with chromic acid or a derivative thereof, such as pyridinium chromate or tert-butyl chromate, dichromate/sulfuric acid, sulfur trioxide in the presence of heterocyclic bases, such as pyridine/$SO_2$, and also nitric acid, pyrolusite or selenium dioxide, in water, organic solvents, such as halogenated solvents, for example methylene chloride, carboxylic acid amides, such as dimethylformamide, or di-lower alkylsulfoxides, such as dimethyl sulfoxide, in the presence or absence of basic amines, for example tri-lower alkylamines, such as triethylamine, at temperatures of from −50° to 100° C., preferably at from −10° to 50° C., or by catalytic dehydrogenation, for example in the presence of metallic silver, copper, copper chromium oxide or zinc oxide at approximately from 200° to 400° C. (in the contact tube) with subsequent rapid cooling. Oxidation with 2,2,6,6-tetramethyl-piperidin-1-oxyl in the presence of NaOCl is also possible (see Anelli et al. Org. Synth. 69, 212 (1990)).

The direct reduction of the amino acids to the aldehydes is also possible, for example by hydrogenation in the presence of a partially poisoned palladium catalyst or by reduction of the corresponding amino acid esters, for example the lower alkyl esters, such as the ethyl ester, with complex hydrides, for example borohydrides, such as sodium borohydride, or preferably aluminum hydrides, for example lithium aluminum hydride, lithium tri(tert-butoxy) aluminum hydride or especially diisobutylaluminum hydride, in non-polar solvents, for example in hydrocarbons or aromatic solvents, such as toluene, at from −100° to 0° C., preferably from −70° to −30° C., and subsequent reaction to form the corresponding semicarbazones, for example with the corresponding acid salts of semicarbazones, such as semicarbazide hydrochloride, in aqueous solvent systems, such as alcohol/water, for example ethanol/water, at temperatures of from −20° to 60° C., preferably from 10° to 30° C., and reaction of the resulting semicarbazone with a reactive aldehyde, for example formaldehyde, in an inert solvent, for example a polar organic solvent, for example a carboxylic acid amide, such as dimethylformamide, at temperatures of from −30° to 60° C., preferably from 0° to 30° C., and then with an acid, for example a strong mineral acid, such as a hydrogen halide, in aqueous solution, optionally in the presence of the solvent used previously, at temperatures of from −40° to 50° C., preferably from −10° to 30° C. The corresponding esters are obtained by reaction of the amino acids with the corresponding carboxylic acids, for example ethanol, analogously to the conditions employed in the condensation under Process b), for example by reaction with inorganic acid halides, such as thionyl chloride, in organic solvent mixtures, such as mixtures of aromatic and alcoholic solvents, for example toluene and ethanol, at temperatures of from −50° to 50° C., preferably from −10° to 20° C.

The preparation of the compounds of formula XIV is carried out in an especially preferred manner under conditions analogous to the reaction conditions mentioned in J. Org. Chem. 47, 3016 (1982) or J. Org. Chem. 43, 3624 (1978).

A sulfur ylid suitable for the conversion of compounds of formula XIV into the epoxides of formula XV is, for example, a dialkylsulfonium methylide, for example dimethylsulfonium methylide, an alkyl- or phenyl-dialkyaminosulfoxonium methylide, for example methyl- or phenyl-dimethylaminosulfoxonium methylide, or a dialkysulfoxonium methylide, for example dimethyl- or diethyl-sulfoxonium methylide.

The sulfur ylid compound in question is advantageously prepared in situ from the corresponding sulfonium or sulfoxonium salt and a base, for example sodium hydride, in a dipolar aprotic solvent, for example dimethyl sulfoxide, or an ether, for example tetrahydrofuran or 1,2-dimethoxyethane, and is then reacted with the compound of formula XIV. The reaction is normally carried out at room temperature, with cooling, for example down to −20° C., or with gentle heating, for example up to 40° C. The sulfide, sulfinamide or sulfoxide formed at the same time is removed in the subsequent aqueous working-up.

The reaction with a sulfur ylid is effected in an especially preferred manner analogously to the conditions mentioned in J. Org. Chem. 50, 4615 (1985).

A compound of formula XV can also be obtained from a compound of formula XIV, as defined above, by reaction thereof with a tri-lower alkylsilymethyl Grigard compound, for example prepared from the corresponding halomethylsilane, such as chloromethyl-trimethyl-silane, in an inert solvent, for example an ether, such as dioxane or diethyl ether, at temperatures of from 0° to 50° C., for example from room temperature to approximately 40° C., subsequent elimination with removal of the silyl radical and formation of a double bond, for example by means of a Lewis acid, such as $BF_3$, any amino-protecting group $R_8$ preferably also being removed, in an inert solvent, for example an ether, such as diethyl ether, or a halogenated hydrocarbon, such as dichloromethane, or a mixture thereof, at temperature of from −50° C. to the reflux temperature, especially from 0° to 30° C., if necessary acylation again with the introduction of an amino-protecting group $R_{12}$, as defined above, and oxidation of the resulting double bond to form the oxirane, preferably with a percarbonxylic acid, for example m-chloroperbenzoic acid or monoperphtalic acid (for example in magnesium salt form), in an inert solvent, for example a halogenated hydrocarbon, such as dichloromethane, or alcohols, such as methanol, lower alkanoylnitriles, such as acetonitrile water or mixtures thereof, as temperatures of from −20° C. to the reflux temperature of the mixture, for example at from 10° to 50° C.

Compounds of formula IV are preferably prepared by starting directly with an alcohol of formula XIII*, as defined above, which is also commercially available, reacting that alcohol with an acid of formula VIII, or with a reactive derivative thereof, as defined for Process c), under the conditions mentioned therein, with, if necessary, protecting groups being introduced, as described under Process a), and removed at suitable times, as described under the heading "Removal of protecting groups", there being obtained a compound analogous to the compound of formula XIII* wherein the place of $R_8$ is taken by the corresponding acyl radical from the acid of formula VIII; the resulting compound is oxidised under conditions analogous to those mentioned for the oxidation of alcohols of formula XIII* to form the corresponding aldehyde of formula

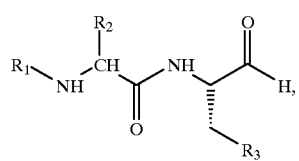

(XIV*)

wherein the radicals are as defined, and that aldehyde is then converted, for example with an ylid compound, as described for the conversion of compounds of formula XIV into compounds of formula XV, into the compound of formula IV.

The starting materials of Processes b), c) and d) are known or, if novel, can be prepared in accordance with processes known per se: for example a compound of formula V can be prepared from a suitable hydrazine derivative of formula XII wherein $R_7$ is a protecting group and the remaining radicals are as defined for compounds of formula V and a suitable epoxide of formula IV wherein the radicals are as defined for compounds of formula I (Process b); a compound of formula VII can be prepared from a suitable hydrazine derivative of formula III wherein the radicals are as defined for compounds of formula I and a suitable epoxide of formula XV wherein $R_8$ is a protecting group and the remaining radicals are as defined for compounds of formula I (Process c); and the compound of formula IX can be prepared from a suitable hydrazine derivative of formula XII wherein $R_7$ is hydrogen and the remaining radicals are as defined for compounds of formula I and a suitable epoxide of formula XV wherein $R_8$ is a protecting group and the remaining radicals are as defined for compounds of formula I (Process d), analogously to Process a), optionally using and removing protecting groups, as described under Process a) and under the heading "Removal of protecting groups", the protecting groups $R_7$ and $R_8$ preferably being as defined above in the definition of compounds of formula XI and XIII, respectively.

Compounds of formula I', wherein the substituents are as defined above, can be prepared, for example, from compounds of formula III',

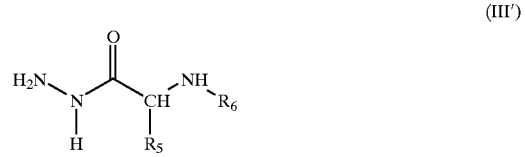

(III')

wherein the radicals are as defined for compounds of formula I, in a manner analogous to that described in Process b), by reaction with a compound of formula IV, wherein any functional groups present that are not to participate in the reaction may be protected as described in Process b) and freed again after the reaction.

Compounds of formula III' can be obtained from compounds of formula XI, as defined above, by reaction with an acid of formula VI, or a reactive acid derivative thereof, wherein the radicals are as defined above, in a manner analogous to that described for the reaction of compounds of formula XII with an acid of formula VI, and, as necessary, subsequent removal of the protecting group $R_7$ in accordance with one of the methods described under the heading "Removal of protecting groups".

Where two amino-protecting groups are present they may be identical or different.

The amino-protecting groups used are, for example, the amino-protecting groups mentioned above under Process a). Preference is given to the corresponding compounds wherein the protecting groups are selected from those described as being preferred for $R_7$ and $R_8$ in compounds of formulae XI and XIII, respectively.

The preparation of the protected compounds of formula I is carried out, for example, in accordance with any of the processes mentioned hereinbelow, especially from compounds of formulae III and IV wherein functional groups may be protected by protecting groups, as described under Process a).

The acids of formulae VI, VIII and VIIIa and the compounds of formula X, and the aldehydes suitable for the introduction of the radical of sub-formula A that are used for the preparation of the compounds of formula XII can be prepared in accordance with processes known per se if they are not already known.

The preparation of the acids of formula VI is effected by reaction of derivatives of a lower alkoxycarbonxylic acid that are suitable for the introduction of lower alkoxycarbonyl radicals, for example by reaction of the corresponding pyrocarbonic acid di-lower alkyl esters (especially pyrocarbonic acid dimethyl ester; Aldrich, Buchs, Switzerland) or preferably haloformic acid lower alkyl esters, such as chloroformic acid lower alkyl esters (especially chloroformic acid methyl ester, Fluka, Buchs, Switzerland), with amino acids of the formula

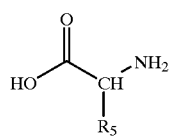

(XVI)

wherein $R_5$ is as defined for compounds of formula VI, under conditions analogous to those described for acylation under Process b), especially in an aqueous alkali metal hydroxide solution, for example aqueous sodium hydroxide solution, in the presence of dioxane at temperatures of from 20° to 100° C. especially from 50° to 70° C.

Correspondingly, the compounds of formula VIII can be obtained from amino acids of formula

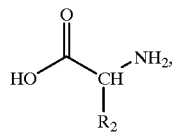

(XVII)

wherein $R_2$ is as defined for compounds of formula I, and the compounds of formula VIIIa can be obtained from amino acids of formula

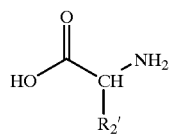

(XVIII)

wherein $R_2'$ is as defined for compounds of formula VIII', by reaction with derivatives of a lower alkoxycarbonxylic acid that are suitable for the introduction of lower alkoxycarbonyl radicals.

The amino acids of formulae XVI, XVII and XVIII are known or can be prepared in accordance with processes known per se. They are preferably in the (S)-form (in respect of the α-carbon atom).

Compounds of formula IV can also be prepared by condensing a compound of formula XIX

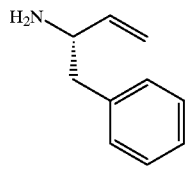

(XIX)

with a compound of formula XVIII, as defined above. The condensation with an acid of formula VIII, or an acid derivative thereof, is carried out under conditions analogous to those mentioned above under Process e). A compound of formula XX.

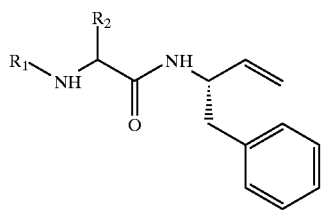

(XX)

wherein $R_1$ and $R_2$ are as defined for compounds of formula I, is obtained.

Epoxidations with oxygen, or preferably chemically bonded oxygen, for example in hydroperoxides, hydrogen peroxides or peroxy acids, such and perbenzoic acid, performic acid, peracetic acid, monoperoxyphtalic acid, pertungstic acid or especially m-chloroperbenzoic acid, in inert solvents, such as ethers, for example diethyl ether, or chlorinated hydrocarbons, such as chloroform or dichloromethane, at preferred temperatures of from –20 to 50° C., yields a compound of formula IV, as defined above.

The starting material of formula XIX is obtained preferably by reaction of a compound of formula XIV wherein $R_3$ is phenyl and $R_8$ is a protecting group with a Grignard reagent that introduces the methylidene group, especially with the trimethylsilylmethyl Grigard reagent (ClMgCH$_2$SI (CH$_3$)$_3$—which can be prepared from chloromethyltrimethylsilane (Fluka, Buchs, Switzerland) under conditions customary for the preparation of Grigand compounds) in an inert solvent, such as an ether, for example diethyl ether, at a preferred temperature of from –65 to 0° C. and subsequent removal of the hydroxy group and trimethylsilyl group, for example with boron trifluoride in an ether, such as diethyl ether, at preferred temperatures of from –20 to 30° C., with simultaneous removal of the protecting group $R_8$ (especially in the case of removal of the tert-butoxycarbonyl protecting group) or with subsequent removal of the protecting group, as described under the heading "Removal of protecting groups".

Also possible is synthesis starting with a compound of formula XIV wherein $R_3$ is phenyl and $R_8$ is a protecting group using a suitable Wittig reagent, such as methyltriphenylphosphonium bromide or iodide in the presence of a strong base, such as sodium amide, at temperatures of from –90 to 0° C., followed by removal of the protecting group $R_8$ in accordance with the conditions mentioned under the heading "Removal of protecting groups".

Compounds of formula X* are known, can be prepared in accordance with processes known per se or can be prepared, for example, as follows:

Using a compound of formula XXI,

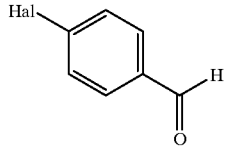

(XXI)

wherein Hal is hydrogen, especially bromine or chlorine, and reacting it with an unsaturated heterocycle that has from 5 to 8 ring atoms, contains from 1 to 4 hetero atoms selected from nitrogen, oxygen, sulfur, sulfinyl (—SO—) and sulfonyl (—SO$_2$—) and is unsubstituted or substituted by lower alkyl or by phenyl-lower alkyl, especially with thiazole or thiophene, in the presence of tetrakis(tripehnylphosphine) palladium as catalyst and in the presence of an alkali metal lower alkanoate, such as potassium acetate, in a suitable solvent, especially a N,N-di-lower alkyl-lower alkanoylamide, such as dimethyl acetamide, at preferred temperatures of from 80° C. to the boiling temperature of the mixture, for example at approximately 150° C., the corresponding compound of formula X*, especially 4-(thiazol-5-yl)-benzaldehyde or 4-(thiopen-2-yl)-benzaldehyde, can be obtained.

Alternatively, it is possible, starting with a compound of formula XXI, as last defined, to obtain the corresponding di-lower alkylacetal (see for example J. Org. Chem. 56, 4280 (1991)), for example the bromobenzaldehyde with orthoformic acid trimethyl ester in an alcohol, such as methanol, in the presence of an acid, such as p-toluenesulfonic acid (can also be used in the form of the hydrate)). The resulting 4-halo-benzaldehyde di-lower alkylacetal is then converted, by reaction with magnesium in the presence of a catalytic amount of iodine in a suitable solvent, such as an ether, for example tetrahydrofuran, at preferred temperatures of from 0° to 70° C., into the corresponding Grigand reagent of formula XXII.

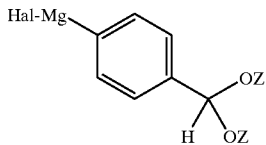

(XXII)

wherein Hal is halogen, especially chlorine or bromine, and Z is lower alkyl, which is then reacted, in the presence of 1,3-bis(diphenylphosphino)propane nickel(II) chloride as catalyst in a suitable solvent, such as ether, for example tetrahydrofuran, there being added in an especially preferred process variant a suitable complex hydride, especially diisobutyl-aluminum hydride, (for example dissolved in a hydrocarbon, such as hexane), at preferred temperatures of from 0° to 60° C., with a compound of formula XXIII, R$_9$–Hal' (XXIII)

wherein R$_9$ is an unsaturated heterocycle that has from 5 to 8 ring atoms, contains from 1 to 4 hetero atoms selected from nitrogen, oxygen, sulfur, sulfinyl (—SO—) and sulfonyl (—SO$_2$—) and is unsubstituted or substituted by lower alkyl or by phenyl-lower alkyl, and wherein Hal' is chlorine or especially bromine, with subsequent acid hydrolysis of the acetal (for example with hydrogen chloride in water), to form the corresponding aldehyde compound of formula X*. Especially preferred as components of formula XXII are 2-bromothiazole, 2- or 3-bromo-pyridine or 2-chloropyrazine in the preparation of the following compounds of formula X*. 4(thiazol-2-yl)-benzaldehyde, 4-(pyridin-2-yl or -3-yl)-benzaldehyde or 4-(pyrazin-2-yl)-benzaldehyde.

Compounds of formula X* wherein R$_4$ is 4-(tetrazolyl-5-yl)-phenyl, are obtainable by reaction of 4-cyanobenzaldehyde with an alkali metal azide, such as sodium azide, in the presence of a suitable alkali metal halide, such as lithium chloride, in a suitable solvent, such as 2-methoxyethanol, preferably at boiling temperature. By reaction with phenyl-lower alkyl halides or preferably with phenyl-lower alkenes, such as 2-phenylpropene, in a suitable solvent, such as toluene, and a suitable acid, such as methanesulfonic acid, preferably under reflux, the corresponding 1- or 2-phenyl-lower alkyl compounds of formula X* are obtained. By reaction with a lower alkyl halide, such as the iodide or bromide, for example methyl iodide, in the presence of alkali metal carbonates, such as potassium or especially caesium carbonate, and suitable solvents, such as dioxane, at preferred temperatures of from approximately 0° to approximately 30° C., compounds of formula X* substituted in the tetrazolyl ring by lower alkyl or by phenyl-lower alkyl, especially 4-(1-methyl-tetrazol-5-yl)-benzaidehyde, are obtained.

Compounds of formula X may be obtained from the corresponding compounds of formula X* by reduction of the aldehyde function to a hydroxymethyl group (for example with complex hydrides, such as lithium aluminum hydride in ethanol, disiamylborane in tetrahydrofuran, sodium borohydride in the presence of lithium chloride in diglycol or sodium borohydride in ethanol) and subsequent introduction of the radical X by esterification by a strong inorganic or organic acid, such as by a mineral acid, for example a hydrohalic acid, such as hydrochloric, hydrobromic or hydriodic acid, or by a strong organic sulfonic acid, such as an unsubstitued or substituted, for example halo-substituted, for example fluorosubstituted, lower alkanesulfonic acid or an aromatic sulfonic acid, for example a benzenesulfonic acid that is unsubstituted or substituted by lower alkyl, such as methyl, halogen, such as bromine, and/or by nitro, for example methanesulfonic acid, p-bromo-toluenesulfonic acid, or p-toluenesulfonic acid, or hydrazoic acid, in accordance with standard methods. For example, by reaction with inorganic acid halides, such as thionyl or phosphoryl halides (for example the chlorides, bromides or iodides), halogen radicals X can be introduced, or the remaining compounds of formula X can be obtained by reaction with other suitable organic or inorganic acids, such as strong organic sulfonic acids (used for example as acid chlorides).

Starting materials (especially those of formulae IV*, V*, VII*, IX* and (I')*) can also be prepared analogously to the processes mentioned in EP 0 521 827 or EP 0 672 448 or are obtainable from the reference sources mentioned therein, or they are known, can be prepared according to processes known per se or are commercially available.

The preparation of starting materials for the preparation of compounds of formula I is preferably carried out analogously to the processes and process steps mentioned in the Examples.

Of the starting materials according to the invention the following are especially preferred (when radicals are not specifically defined, the meanings mentioned in the definition for compounds of formula I apply in each case):

(1) compounds of formula XX wherein R$_1$ is methoxycarbonyl or ethoxycarbonyl and R$_2$ is tert-butyl;

(2) compounds of formula IV wherein R$_1$ is methoxycarbonyl or ethoxycarbonyl and R$_2$ is tert-butyl;

(3) compounds of formula III*, especially those wherein R$_5$ is tert-butyl and R$_6$ is ethoxycarbonyl;

(4) compounds of formula XII;

(5) compounds of formula XII*;

(6) compounds of formula III;

(7) compounds of formula V;

(8) compounds of formula VII;

(9) compounds of formula IX;

(10) compounds of formula X;

(11) a compound of formula X* selected from 4-(1-methyl-tetrazol-5-yl)-benzaldehyde, 4-(thiazol-2-yl)-benzaldehyde, 4-(pyridin-2-yl) or -3-yl)-benzaldehyde, 4-(pyrazin-2-yl)-benzaldehyde, 4-(thiazol-5-yl)-benzaldehyde and 4-(thiophen-2-yl)-benzaldehyde.

(12) compounds of formula XXIV

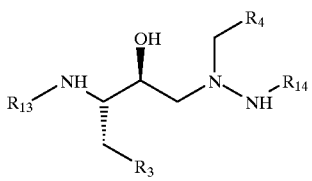

(XXIV)

wherein $R_{13}$ and $R_{14}$ are amino-protecting groups, which are different from one another, selected from those mentioned under Process a), especially tert-lower alkoxycarbonyl, such as tert-butoxycarbonyl, or an acylamino-protecting group, especially trifluoroacetyl; preferably $R_{13}$ is trifluoroacetyl and $R_{14}$ is tert-butoxycarbonyl; (those compounds are compounds of formula IX that are protected at both amino groups);

(13) compounds of formula XXV,

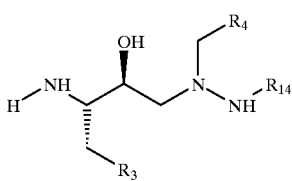

(XXV)

wherein $R_{14}$ is an amino-protecting group, as defined for compounds of formula XXIV, especially tert-butoxycarbonyl;

(14) compounds of formula XXVI,

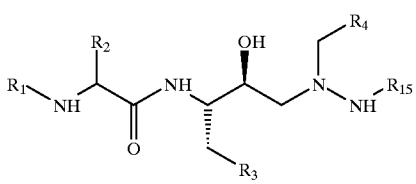

(XXVI)

wherein $R_{15}$ is an amino-protecting group, especially tert-butoxycarbonyl, and the remaining radicals are as defined for compounds of formula I. (15) 1-[4-(2-tert-butyl-2H-tetrazol-5-yl)-phenyl]-4(S)-hydroxy-5(S)-N-(tert-butyloxycarbonyl)amino-2-N-[N-methoxycarbonyl-(L)-tert-leucyl]amino-6-phenyl-2-azahexane (as intermediate, but also pharmaceutically active).

When salt-forming groups are present, the compounds mentioned above under (1) to (15) as starting materials may also be in the form of a salt.

EXAMPLES

The following Examples serve to illustrate the invention without limiting the scope thereof:

Temperatures are indicated in degrees Celsius (° C.). Where no temperature is indicated, the reactions that follow are carried out at room temperature. The $R_f$ values, which indicate the ratio of the seepage propagation of the substance in question to the seepage propagation of the eluant front, are determined on silica gel thin-layer plates (Merck, Darmstadt, Germany) by thin-layer chromatography (TLC) using the solvent systems mentioned in each case.

HPLC gradients used:

| | |
|---|---|
| $HPLC_{20-100}$ | 20% → 100% a) in b) for 20 min. |
| $HPLC_{20-100(12')}$ | 20% → 100% a) in b) for 12 min., then 8 min 100% a) |
| $HPLC_{5-60}$ | 5% → 60% a) in b) for 15 min. |

Eluant a): acetonitrile+0.05% TFA; eluant b): water+ 0.05% TFA. Column (250×4 . . . 6 mm) packed with "reversed-phase" material C18-Nucleosil (5 μm mean particle size, silica gel covalently derivatised with octadecylsilanes, Macherey & Nagel, Düren, Germany). Detection by UV-absorption at 254 nm. Retention times ($t_{Ret}$) are given in minutes. Flow rate 1 ml/min.

The other abbreviations used have the following meanings:

| | |
|---|---|
| abs. | absolute (indicates that solvent is anhydrous) |
| anal. | elemental analysis |
| Boc | tert-butoxycarbonyl |
| calc. | calculated |
| DBU | 1,8-diazabicyclo[5.4.0]undec-7-ene-(1,5-5) |
| TLC | thin-layer chromatography |
| DIPE | diisopropyl ether |
| DMF | dimethylformamide |
| DPPP | [1,3-bis(diphenylphosphino)propane]nickel(II) chloride (Aldrich, Milwaukee, USA) |
| EDC | N-ethyl-N'-(3-dimethylaminopropyl)-carbodiimide hydrochloride |
| ether | diethyl ether |
| FAB-MS | fast atom bombardment mass spectroscopy |
| sat. | saturated |
| HOAc | acetic acid |
| HOBT | 1-hydroxy-benzotriazole |
| HPLC | High Performance Liquid Chromatography |
| Hünig base | N-ethyldiisopropylamine |
| MeOH | methanol |
| min | minute(s) |
| NMM | N-methylmorpholine |
| Pd/C | palladium on charcoal |
| $Pd(PPh_3)_4$ | tetrakis(triphenylphosphine)palladium |
| iso-PrOH | isopropanol |
| $R_f$ | ratio of seepage propagation to the eluant front in TLC |
| $SiO_2$ | silica gel |
| m.p. | melting point |
| brine | saturated sodium chloride solution |
| TEA | triethylamine |
| TFA | trifluoroacetic acid |
| THF | tetrahydrofuran (dist. over sodium/benzophenone) |
| TPTU | O-(1,2-dihydro-2-oxo-1-pyridyl)-N,N,N',N'-tetramethyluronium tetrafluoroborate |
| p-TSA | p-toluenesulfonic acid |

Source of some amino acid derivatives used as starting materials:

(2R)-[(1'S)-Boc-amino-2'-phenylethyl]oxirane J. Org. Chem. 50, 4615 (1985)

(2R)-[(1'S)-(trifluoroacetyl)amino-2'-phenylethyl]oxirane (European Patent Application EP 0 521 827, page 78, Ex. 16d))

N-methoxycarbonyl-(L)-valine (Preparation see Chem. Lett. 705 (1980))

N-ethoxycarbonyl-(L)-valine (Preparation see J. Org. Chem. 60, 7256 (1995))

N-methoxycarbonyl-(L)-iso-leucine (Preparation see Chem. Lett. 705 (1980))

EXAMPLE 1

1-[4-(Thiazol-5-yl)-phenyl]-4(S)-hydroxy-5(S)-2,5-bis[N-(N-methoxycarbonyl-(L)-valyl)amino]-6-phenyl-2-azahexane With the exclusion of moisture, 735 mg (4.20 mmol) of N-methoxycarbonyl-(L)-valine (see EP 0 604 368, Example 2b)), 1548 mg (8.07 mmol) of EDC and 654 mg (4.844 mmol) of HOBT are placed in 10 ml of DMF. 1.13 ml (8.07 mmol) of TEA are added to the white suspension and the mixture is stirred at room temperature for 30 min. Then 595 mg (1.62 mmol) of 1-[4-(thiazol-5-yl)-phenyl]-4(S)-hydroxy-5(S)-2,5-diamino-6-phenyl-2-azahexane dissolved in 1 ml of DMF are added and the mixture is stirred ovenight to complete the reaction. The reaction mixture is concentrated by evaporation; the resulting oil is dissolved in methylene chloride and washed with 10% citric acid solution, sat. $NaHCO_3$ solution and brine. The aqueous phases are extracted 2× with methylene chloride; the combined organic phases are filtered through cotton wadding and concentrated by evaporation. Column chromatography ($SiO_2$; $CH_2Cl_2$/MeOH/$H_2O$/HOAc 85:13:1.5:0.5) and precipitation with DIPE from a concentrated solution in methylene chloride yield the title compound: TLC: $R_f$=0.57 ($CH_2Cl_2$/MeOH/$H_2O$/HOAc 85:13:1.5:0.5); $HPLC_{20-100}$: $t_{Ret}$=13.0; FAB MS $(M+H)^+$=683.

The starting material is prepared as follows:

1a) 4-(Thiazol-5-yl)-benzaldehyde

In a bomb tube, a mixture of 3.7 g (20 mmol) of 4-bromobenzaldehyde (Fluka, Buchs, Switzerland), 6.64 ml (93 mmol) of thiazole, 2.94 g of potassium acetate and 1.16 g (1 mmol) of $Pd(PPh_3)_4$ in 50 ml of dimethylacetamide is stirred at 150° C. for 12 hours. The reaction mixture is concentrated by evaporation. Water is added to the residue and the mixture is extracted 3× with methylene chloride. The organic phases are filtered through cotton wadding, concentrated by evaporation and chromatographed ($SiO_2$; hexane/ethyl acetate 1:2), yielding the title compound: $HPLC_{20-100}$:$t_{Ret}$=11.4; $^1$H-NMR ($CD_3OD$) δ 9.98 (s, HCO), 9.03 (s, H(2)$^{thiazole}$), 8.32 (s, H(4)$^{thiazole}$), 7.95 and 7.85 (2d, J=8, each 2H); additionally also signals of the hydrate (≈12%): 8.92 (s, H2)$^{thiazole}$), 8.15 (s, H(4)$^{thiazole}$), 7.62 and 7.53 (2d, J=8, each 2H), 5.54 (s, HC(OH)$_2$).

1b) N-1-(tert-Butoxycarbonyl)-N-2-{[4-(thiazol-5-yl)-phenyl]-methylidene}-hydrazone A solution of 1.22 g (6.45 mmol) of 4-(thiazol-5-yl)-benzaldehyde and 1.12 g (6.14 mmol) of tert-butyl carbazate (Fluka, Buchs, Switzerland) in 40 ml of ethanol is stirred at 80° C. for 12 hours. Cooling and crystallisation by the addition of 60 ml of water at 0° C. yield the title compound: m.p: 170–171° C.; $HPLC_{20-100}$:$t_{Ret}$=13.5.

1c) N-1-(tert-Butoxycarbonyl)-N-2-[4-(thiazol-5-yl)-benzyl]-hydrazine

Under a nitrogen atmosphere, 20.4 g (67.2 mmol) of N-1-(tert-butoxycarbonyl)-N-2-{[4-(thiazol-5-yl)-phenyl]-methylidene}-hydrazone are placed in 120 ml of THF, and 4.67 g (70.7 mmol; 95%) of sodium cyanoborohydride are added. A solution of 12.8 g (67.2 mmol) of p-toluenesulfonic acid monohydrate in 120 ml of THF (pH 3–4) is then added dropwise thereto. After 7 hours, water and ethyl acetate are added and the aqueous phase is separated off and extracted a further 2× with ethyl acetate. The organic phases are washed with brine, sat. $NaHCO_3$ solution and brine, dried ($Na_2SO_4$) and concentrated by evaporation. To the resulting viscous oil there are added 80 ml of dichloroethane and 80 ml of 1N NaOH solution (foams) and the mixture is boiled under reflux for 7 hours. The reaction mixture is cooled and diluted with methylene chloride and water; the aqueous phase is separated off and extracted 2× with methylene chloride. The organic phases are dried ($Na_2SO_4$), concentrated by evaporation and chromatographed ($SiO_2$; hexane/ethyl acetate 2:1). Stirring in hexane yields the title compound: m.p: 93–95° C.; TLC: $R_f$=0.12 (hexane/ethyl acetate 2:1); Anal. ($C_{15}H_{19}N_3O_2S$) calc. C 58.99, H 6.27, N 13.76, S 10.50; found C 58.98, H 6.34, N 13.64, S 10.66; $HPLC_{20-100}$: $t_{Ret}$=10.1.

1d) 1-[4-Thiazol-5-yl)-phenyl]-4(S)-hydroxy-5(S)-2,5-bis[(tert-butoxycarbonyl)amino]-6-phenyl-2-azahexane A suspension of 1.21 g (4.6 mmol) of (2R)-[(1'S)-Boc-amino-2'-phenylethyl]oxirane and 1.4 g (4.6 mmol) of N-1-(tert-butoxycarbonyl)-N-2-[4-(thiazol-5-yl)-benzyl]-hydrazine in 25 ml of iso-PrOH is heated at boiling overnight. The reaction mixture is cooled and water is added. The supernatant phase is decanted off from the oil that has separated out; the oil is dried in vacuo and chromatographed ($SiO_2$; methylene chloride/methanol 30:1), yielding the title compound: TLC: $R_f$=0.2 (methylene chloride/methanol 30:1); $HPLC_{20-100}$: $t_{Ret}$=17.2.

1e) 1-[4-(Thiazol-5-yl)-phenyl]-4(S)-hydroxy-5(S)-2,5-diamino-6-phenyl-2-azahexane A solution of 1.14 g (2.0 mmol) of 1-[4-(thiazol-5-yl)-phenyl]-4(S)-hydroxy-5(S)-2,5-bis[(tert-butoxycarbonyl)amino]-6-phenyl-2-azahexane in 100 ml of formic acid is stirred at room temperature for 3 hours and then concentrated by evaporation. Sat. $HaHCO_3$ solution and methylene chloride are added to the residue; the aqueous phase is separated off and extracted 2× with methylene chloride. The organic phases are treated with brine, filtered through cotton wadding and concentrated by evaporation to form the title compound which is used further directly.

EXAMPLE 2

1-[4-(Thiazol-5-yl)-phenyl]-4(S)-hydroxy-2-N-(N-methoxycarbonyl-(L)-valyl)-amino-5(S)-N-(N-methoxycarbonyl-(L)-tert-leucyl)amino-6-phenyl-2-azahexane Under an argon atmosphere, 344 mg of 1-[4-(thiazol-5-yl)-phenyl]-4(S)-hydroxy-2-amino-5(S)-N-(N-methoxycarbonyl-(L)-tert-leucyl)amino-6-phenyl-2-azahexane and 191 μl (1.74 mmol) of NMM in 5.6 ml of DMF are added to 122 mg (0.696 mmol) of N-methoxycarbonyl-(L)-valine and 173 mg (0.58 mmol) of TPTU in 2.9 ml of DMF and the mixture is stirred at room temperature for 16 hours. The reaction mixture is poured into ice-water, stirred for 30 min and filtered. Column chromatography of the residue ($SiO_2$; methylene chloride/THF 4:1) and stirring in ether yield the title compound: m.p: 134–135° C.; $HPLC_{20-100}$: $t_{Ret}$=14.0; FAB MS $(M+H)^+$=697.

The starting material is prepared as follows:

2a) 1-[4-(Thiazol-5-yl)-phenyl]-4(S)-hydroxy-2-(tert-butoxycarbonyl)amino-5(S)-(trifluoroacetyl)amino-6-phenyl-2-azahexane A suspension of 5.32 g (20.5 mmol) of (2R)-[(1'S)-(trifluoroacetyl)amino-2'-phenylethyl]-oxirane and 5.7 g (18.6 mmol) of N-1-(tert-butoxycarbonyl)-N-2-[4-(thiazol-5-yl)-benzyl]-hydrazine (Example 1c) in 95 ml of iso-PrOH is heated at boiling for 8 hours. After cooling, the reaction mixture is partially concentrated by evaporation and left to stand at 0° C., resulting in the crystallisation of the title compound which is filtered off with suction and dried. TLC: $R_f$=0.39 (methylene chloride/THF 10:1); $HPLC_{20-100}$: $t_{Ret}$=16.5; FAB MS $(M+H)^+$=565. Further product can be obtained from the mother liquor by boiling again with (2R)-[(1'S)-(trifluoroacetyl)amino-2'-phenylethyl]oxirane in iso-PrOH and column chromatography ($SiO_2$; methylene chloride/THF 15:1).

2b) 1-[4-(Thiazole-5-yl)-phenyl]-4(S)-hydroxy-2-(tert-butoxycarbonyl)amino-5(S)-amino-6-phenyl-2-azahexane 100 ml of a 1N $K_2CO_3$ solution are added dropwise to a solution of 5.646 g (10.0 mmol) of 1-[4-(thiazol-5-yl)-phenyl]-4(S)-hydroxy-2-(tert-butoxycarbonyl)amino-5(S)-(trifluoroacetyl)amino-6-phenyl-2-azahexane in 100 ml of methanol and the mixture is stirred at 70° C. for 15 hours. Methylene chloride and water are added; the aqueous phase is separated off and extracted 2× with methylene chloride. The organic phases are washed 2× with water, dried ($Na_2SO_4$) and concentrated by evaporation, yielding the title compound: Anal. ($C_{25}H_{32}N_4O_3S$ (0.53 $H_2O$)) calc. C 62.80, H 6.97, N 11.72, S 6.71, $H_2O$ 2.00: found C 63.2, H 7.01, N 11.57, S 6.49, $H_2O$ 1.98; $HPLC_{20-100}$: $t_{Ret}$=11.5.

2c) 1-[4-(Thiazol-5-yl)-phenyl]-4(S)-hydroxy-2-(tert-butoxycarbonyl)amino-5(S)-N-(N-methoxycarbonyl-(L)-tert-leucyl)amino-6-phenyl-2-azahexane Under an nitrogen atmosphere, 1.36 g (7.2 mmol) of N-methoxycarbonyl-(L)-tert-leucine (Example 2e), 2.59 g (13.5 mmol) of EDC and 1.22 g (9.0 mmol) of HOBT are dissolved in 20 ml of DMF. After 15 min, 3.79 ml (27 mmol) of TEA are added and then a solution of 2.11 g (4.5 mmol) of 1-[4-(thiazol-5-yl)-phenyl]-4(S)-hydroxy-2-(tert-butoxycarbonyl)amino-5(S)-amino-6-phenyl-2-azahexane in 41 ml of DMF is added dropwise. After 3 hours the reaction mixture is concentrated by evaporation. The resulting oil is dissolved in ethyl acetate and a small amount of THF and washed with 2× water, sat. $NaHCO_3$ solution, 2× water and brine. The aqueous phases are extracted with ethyl acetate; the combined organic phases are dried ($Na_2SO_4$) and concentrated by evaporation. Column chromatography ($SiO_2$; methylene chloride/THF 5:1) and crystallisation from ethyl acetate/DIPE yield the title compound: $HPLC_{20-100}$: $t_{Ret}$=16.0; FAB MS $(M+H)^+$=640.

2d) 1-[4-(Thiazol-5-yl)-phenyl]-4(S)-hydroxy-2-amino-5(S)-N-(N-methoxycarbonyl-(L)-tert-leucyl)amino-6-phenyl-2-azahexane 742 mg (1.16 mmol) of 1-[4-(thiazol-5-yl)-phenyl]-4(S)-hydroxy-2-(tert-butoxycarbonyl)amino-5(S)-N-(N-methoxycarbonyl-(L)-tert-leucyl)amino-6-phenyl-2-azahexane and 12 ml of formic acid are stirred at room temperature for 7 hours and then concentrated by evaporation. Sat. $NaHCO_3$ solution and ethyl acetate are added to the residue; the aqueous phase is separated off and extracted with ethyl acetate. The organic phases are treated with water and brine, dried ($Na_2SO_4$) and concentrated by evaporation, yielding the title compound which is used further directly.

2e) N-(Methoxycarbonyl)-(L)-tert-leucine 23.5 ml (305 mmol) of methyl chloroformate are added over a period of 20 min to a solution of 20 g (152 mmol) of (L)-tert-leucine (=2(S)-amino-3,3-dimethyl-butyric acid=(L)-α-tert-butylglycine; Fluka, Buchs/Switzerland) in a mixture of 252 ml (504 mmol) of 2N aqueous sodium hydroxide solution and 80 ml of dioxane and the reaction solution is heated at 60° C. for 14 hours. After cooling to room temperature, the reaction solution is washed 2× with methylene chloride. The aqueous phase is acidified to pH 2 with 4N aqueous hydrochloric acid and extracted three times with ethyl acetate. The organic extracts are combined, dried ($Na_2SO_4$) and concentrated by evaporation, the product beginning to solidify. Digestion of the solidified solid with hexane yields the title compound in the form of a white powder. M.p. 106–108° C.

Example 3
1-[4-(Thiazol-5-yl)-phenyl]-4(S)-hydroxy-5(S)-2,5-bis[N-(N-methoxycarbonyl-(L)-tert-leucyl)amino]-6-phenyl-2-azahexane Under an argon atmosphere, 292 mg of 1-[4-(thiazole-5-yl)-phenyl]-4(S)-hydroxy-2-amino-5(S)-N-(N-methoxycarbonyl-(L)-tert-leucyl)amino-6-phenyl-2-azahexane (Example 2d) and 165 μl (1.5 mmol) of NMM in 4.8 ml of DMF are added to 113.5 mg of N-methoxycarbonyl-(L)-tert-leucine (Example 2e) and 149 mg (0.50 mmol) of TPTU in 2.5 ml of DMF and the mixture is stirred at room temperature for 14 hours. The reaction mixture is poured into 0.2 liter of ice-water, stirred for 45 min and filtered. Column chromatography of the residue ($SiO_2$; methylene chloride/ethanol 20:1) and crystallisation from ethyl acetate/ether/hexane yield the title compound: m.p: 207–209° C.; TLC: $R_f$=0.25 (methylene chloride/ethanol 20:1); $HPLC_{20-100}$: $t_{Ret}$=14.7; FAB MS $(M+H)^+$=711.

Example 4
1-[4-(Thiazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane Under an argon atmosphere, 292 mg of 1-[4-(thiazol-5-yl)-phenyl]-4(S)-hydroxy-2-amino-5(S)-N-(N-methoxycarbonyl-(L)-tert-leucyl)amino-6-phenyl-2-azahexane (Example 2d) and 165 μl (1.5 mmol) of NMM in 4.8 ml of DMF are added to 113 mg of N-methoxycarbonyl-(L)-iso-leucine and 149 mg (0.50 mmol) of TPTU in 2.5 ml of DMF, and the mixture is stirred at room temperature for 14 hours and worked up analogously to Example 3, yielding the title compound: m.p: 139–141° C.; TLC: $R_f$=0.7 (methylene chloride/methanol 10:1); $HPLC_{20-100}$: $t_{Ret}$=14.6; FAB MS $(M+H)^+$=711.

Example 5
1-[4-(Thiazol-5-yl)-phenyl]-4(S)-hydroxy-2-N-(N-methoxycarbonyl-(L)-S-methylcysteinyl)amino-5(S)-N-(N-methoxycarbonyl-(L)-tert-leucyl)amino-6-phenyl-2-azahexane Under an argon atmosphere, 292 mg of 1-[4-(thiazol-5-yl)-phenyl]-4(S)-hydroxy-2-amino-5(S)-N-(N-methoxycarbonyl-(L)-tert-leucyl)amino-6-phenyl-2-azahexane (Example 2d) and 165 μl (1.5 mmol) of NMM in 4.8 ml of DMF are added to 116 mg (0.60 mmol) of N-methoxycarbonyl-(L)-S-methylcysteine and 149 mg (0.50 mmol) of TPTU in 2.5 ml of DMF, and the mixture is stirred at room temperature for 5 hours and worked up analogously to Example 3, yielding the title compound: TLC: $R_f$=0.4 (methylene chloride/methanol 10:1); $HPLC_{20-100}$: $t_{Ret}$=13.6; FAB MS $(M+H)^+$=715.

The starting material is prepared as follows:

5a) N-methoxycarbonyl-(L)-S-methylcysteine

With ice-cooling, 16.8 g (177.5 mmol) of chloroformic acid methyl ester are added dropwise to a solution of 12.0 g (88.8 mmol) of S-methyl-(L)-cysteine ((S)-2-amino-3-methylmercapto-propionic acid: Fluka; Buchs/Switzerland) in 150 ml of 2N sodium hydroxide solution and 18 ml of dioxane and the mixture is stirred at 70° C. overnight to complete the reaction. The reaction mixture is diluted with 150 ml of methylene chloride; the aqueous phase is separated off, acidified with 1N HCl and extracted 3× with ethyl acetate. Drying ($Na_2SO_4$) and concentration of the ethyl acetate phases by evaporation yield the title compound: FAB MS $(M+H)^+$=194.

Example 6
1-[4-Thiazol-5-yl)-phenyl]-4(S)-hydroxy-2-N-(N-ethoxycarbonyl-(L)-valyl)amino-5(S)-N-(N-methoxycarbonyl-(L)-tert-leucyl)amino-6-phenyl-2-azahexane Under an argon atmosphere, 344 mg of 1-[4-(thiazol-5-yl)-phenyl]-4(S)-hydroxy-2-amino-5(S)-N-(N-methoxycarbonyl-(L)-tert-leucyl)amino-6-phenyl-2-azahexane (Example 2d) and 191 µl (1.74 mmol) of NMM in 5.6 ml of DMF are added to 132 mg (0.7 mmol) of N-ethoxycarbonyl-(L)-valine (EP 0 604 368, Example 9a) and 173 mg (0.58 mmol) of TPTU in 2.9 ml of DMF, and the mixture is stirred at room temperature overnight and worked up analogously to Example 3, yielding the title compound: TLC: $R_f$=0.45 (methylene chloride/THF 4:1); $HPLC_{20-100}$: $t_{Ret}$=14.7; FAB MS $(M+H)^+$=711.

Example 7

1-[4-(Thiazol-5-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane Under argon, 213 mg (1.13 mmol) of N-methoxycarbonyl-(L)-tert-leucine (Example 2e), 431 mg (2.25 mmol) of EDC and 304 mg (2.25 mmol) of HOBT are placed in 18 ml of DMF. After 15 min, 627 µl (4.5 mmol) of TEA and 0.75 mmol of 1-[4-(thiazol-5-yl)-phenyl]-4(S)-hydroxy-2-amino-5(S)-N-(N-methoxycarbonyl-(L)-valyl)amino-6-phenyl-2-azahexane are added. After 2 hours, water and ethyl acetate are added; the aqueous phase is separated off and extracted a further 2× with ethyl acetate. The organic phases are washed 2× with water, sat. $NaHCO_3$ solution, 2× water and brine, dried ($Na_2SO_4$) and concentrated by evaporation. Column chromatography ($SiO_2$; methylene chloride/THF 5:1) and crystallisation from ether yield the title compound: m.p: 200–201° C.; $HPLC_{20-100}$: $t_{Ret}$=14.0; FAB MS $(M+H)^+$=697.

The starting material is prepared as follows:

7a) 1-[4-(Thiazol-5-yl)-phenyl]-4(S)-hydroxy-2-(tert-butoxycarbonyl)amino-5(S)-N-(N-methoxycarbonyl-(L)-valyl)amino-6-phenyl-2-azahexane Under a nitrogen atmosphere, 2.66 g (15.2 mmol) of N-methoxycarbonyl-(L)-valine, 5.46 g (28.5 mmol) of EDC and 2.57 g (19 mmol) of HOBT are dissolved in 42 ml of DMF. 7.9 ml (57 mmol) of TEA are added and after 20 min a solution of 4.46 g (9.5 mmol) of 1-[4-(thiazol-5-yl)-phenyl]-4(S)-hydroxy-2-(tert-butoxycarbonyl)amino-5(S)-amino-6-phenyl-2-azahexane (Example 2b) in 85 ml of DMF is added dropwise. After 1.5 hours, the reaction mixture is worked up analogously to Example 2c. Crystallisation from THF/ether yields the title compound: m.p: 114–115° C.; $HPLC_{20-100}$:$t_{Ret}$=15.1; FAB MS $(M+H)^+$=626.

7b) 1-[4-(Thiazol-5-yl)-phenyl]-4(S)-hydroxy-2-amino-5(S)-N-(N-methoxycarbonyl-(L)-valyl)amino-6-phenyl-2-azahexane 1.25 g (2.0 mmol) of 1-[4-(thiazol-5-yl)-phenyl]-4(S)-hydroxy-2-(tert-butoxycarbonyl)amino-5(S)-N-(N-methoxycarbonyl-(L)-valyl)amino-6-phenyl-2-azahexane and 18 ml of formic acid are reacted analogously to Example 2d to form the title compound: $HPLC_{20-100}$: $t_{Ret}$=10.0.

Example 8

1-[4-(Thiazol-5-yl)-phenyl]-4(S)-hydroxy-2-N-(N-ethoxycarbonyl-(L)-valyl)amino-5(S)-N-(N-methoxycarbonyl-(L)-valyl)amino-6-phenyl-2-azahexane Analogously to Example 7, 213 mg (1.13 mmol) of N-ethoxycarbonyl-(L)-valine, 431 mg (2.25 mmol) of EDC and 304 mg (2.25 mmol) of HOBT in 18 ml of DMF and 627 µl (4.5 mmol) of TEA are reacted with 0.75 mmol of 1-[4-(thiazol-5-yl)-phenyl]-4(S)-hydroxy-2-amino-5(S)-N-(N-methoxycarbonyl-(L)-valyl)amino-6-phenyl-2-azahexane (Example 7b) to form the title compound: m.p: 243–244° C.; $HPLC_{20-100}$: $t_{Ret}$=14.0; FAB MS $(M+H)^+$=697.

Example 9

1-[4-(Thiazol-5-yl)-phenyl]-4(S)-hydroxy-2-N-(N-methoxycarbonyl-(L)-iso-leucyl)amino-5(S)-N-(N-methoxycarbonyl-(L)-valyl)amino-6-phenyl-2-azahexane Under an argon atmosphere, 0.6 mmol of 1-[4-(thiazol-5-yl)-phenyl]-4(S)-hydroxy-2-amino-5(S)-N-(N-methoxycarbonyl-(L)-valyl)amino-6-phenyl-2-azahexane and 198 µl (1.8 mmol) of NMM in 5.8 ml of DMF are added to 136 mg (0.72 nmol) of N-methoxycarbonyl-(L)-iso-leucine and 179 mg (0.60 mmol) of TPTU in 3 ml of DMF and the mixture is stirred at room temperature for 14 hours and worked up analogously to Example 3, yielding the title compound: TLC: $R_f$=0.59 (methylene chloride/THF 3:1); $HPLC_{20-100}$: $t_{Ret}$=14.0; FAB MS $(M+H)^+$=697.

Example 10

1-[4-(Thiazol-5-yl)-phenyl]-4(S)-hydroxy-2-N-(N-methoxycarbonyl-(L)-S-methylcysteinyl)amino-5(S)-N-(N-methoxycarbonyl-(L)-valyl)amino-6-phenyl-2-azahexane Under an argon atmosphere, 0.58 mmol of 1-[4-(thiazol-5-yl)-phenyl]-4(S)-hydroxy-2-amino-5(S)-N-(N-methoxycarbonyl-(L)-valyl)amino-6-phenyl-2-azahexane and 191 µl (1.74 mmol) of NMM in 5.6 ml of DMF are added to 134 mg (0.696 mmol) of N-methoxycarbonyl-(L)-S-methylcysteine (Example 5a) and 173 mg (0.58 mmol) of TPTU in 2.9 ml of DMF and the mixture is stirred at room temperature for 15 hours and worked up analogously to Example 3, yielding the title compound: TLC: $R_f$=0.17 (methylene chloride/THF 4:1); $HPLC_{20-100}$: $t_{Ret}$=13.0; FAB MS $(M+H)^+$=701.

Example 11

1-[4-(Thiazol-5-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane Under argon, 0.5 mmol of 1-[4-(thiazol-5-yl)-phenyl]-4(S)-hydroxy-2-amino-5(S)-N-(N-methoxycarbonyl-(L)-iso-leucyl)amino-6-phenyl-2-azahexane and 165 µl (1.5 mmol) of NMM in 4.8 ml of DMF are added to 113.5 mg (0.60 mmol) of N-methoxycarbonyl-(L)-tert-leucine (Example 2e) and 149 mg (0.50 mmol) of TPTU in 2.5 ml of DMF and the mixture is stirred at room temperature for 14 hours. Ice-water and and ethyl acetate are added; the aqueous phase is separated off and extracted with ethyl acetate. The organic phases are washed 2× with water and brine, dried ($Na_2SO_4$) and concentrated by evaporation. Column chromatography ($SiO_2$; ethyl acetate) and crystallisation from ethyl acetate/ether/hexane yield the title compound: TLC: $R_f$=0.42 (methylene chloride/ethanol 10:1); $HPLC_{20-100}$: $t_{Ret}$=14.8; FAB MS $(M+H)^+$=711.

The starting material is prepared as follows:

11a) 1-[4-(Thiazol-5-yl)-phenyl]-4(S)-hydroxy-2-(tert-butoxycarbonyl)amino-5(S)-N-(N-methoxycarbonyl-(L)-iso-leucyl)amino-6-phenyl-2-azahexane Under a nitrogen atmosphere, 1.36 g (7.2 mmol) of N-methoxycarbonyl-(L)-iso-leucine, 2.59 g (13.5 mmol) of EDC and 1.22 g (9 mmol) of HOBT are dissolved in 20 ml of DMF. After 30 min, 3.79 ml (27 mmol) of TEA are added and a solution of 2.11 g (4.5 mmol) of 1-[4-(thiazol-5-yl)-phenyl]-4(S)-hydroxy-2-(tert-butoxycarbonyl)amino-5(S)-amino-6phenyl-2-azahexane (Example 2b) in 40 ml of DMF are added dropwise. After 3 hours, the reaction mixture is worked up analogously to Example 2c to form the title compound: m.p: 163–166° C.; Anal. ($C_{33}H_{45}N_5O_6S$ (0.14 $H_2O$) calc. C 61.71, H 7.11, N 10.90, S 4.99, $H_2O$ 0.39: found C 61.61, H 7.10, N 10.79, S 4.76, $H_2O$ 0.4; $HPLC_{20-100}$: $t_{Ret}$=16.0; FAB MS $(M+H)^+$=640.

11b) 1-[4-(Thiazol-5-yl)-phenyl]-4(S)-hydroxy-2-amino-5(S)-N-(N-methoxycarbonyl-(L)-iso-leucyl)amino-6-phenyl-2-azahexane 320 mg (0.50 mmol) of 1-[4-(thiazol-5-yl)-phenyl]-4(S)-hydroxy-2-(tert-butoxycarbonyl)-amino-5(S)-N-(N-methoxycarbonyl-(L)-iso-leucyl)amino-6-phenyl-2-azahexane and 6 ml of formic acid are reacted analogously to Example 2d to form the title compound which is used further directly.

Example 12

1-[4-(Thiazol-5-yl)-phenyl]-4(S)-hydroxy-2-N-(N-methoxycarbonyl-(L)-valyl)amino-5(S)-N-(N-methoxycarbonyl-(L)-iso-leucyl)amino-6-phenyl-2-azahexane Analogously to Example 7, 140 mg (0.80 mmol) of N-methoxycarbonyl-(L)-valine, 288 mg (1.5 mmol) of EDC and 135 mg (1.0 mmol) of HOBT in 2 ml of DMF and 418 $\mu$l of TEA are reacted with 0.5 mmol of 1-[4-(thiazol-5-yl)-phenyl]-4(S)-hydroxy-2-amino-5(S)-N-(N-methoxycarbonyl-(L)-iso-leucyl)amino-6-phenyl-2-azahexane in 5 ml of DMF to form the title compound: m.p: 202–204° C.; HPLC$_{20\text{-}100}$: t$_{Ret}$=14.0; FAB MS (M+H)$^+$=697.

Example 13

1-[4-(Thiazol-5-yl)-phenyl]-4(S)-hydroxy-5(S)-2,5-bis[N-(N-methoxycarbonyl-(L)-iso-leucyl)amino]-6-phenyl-2-azahexane Analogously to Example 7, 175 mg (0.92 mmol) of N-methoxycarbonyl-(L)-iso-leucine, 332 mg (1.7 mmol) of EDC and 156 mg (1.15 mmol) of HOBT in 2.5 ml of DMF and 483 $\mu$l (3.47 mmol) of TEA are reacted with 0.578 mmol of 1-[4-(thiazol-5-yl)-phenyl]-4(S)-hydroxy-2-amino-5(S)-N-(N-methoxycarbonyl-(L)-iso-leucyl)amino-6-phenyl-2-azahexane (Example 11b) in 5.2 ml of DMF to form the title compound: m.p: 213–216° C.; HPLC$_{20\text{-}100}$: t$_{Ret}$=14.7; FAB MS (M+H)$^+$=711.

Example 14

1-[4-(Thiazol-5-yl)-phenyl]-4(S)-hydroxy-2N-(N-ethoxycarbonyl-(L)-valyl)amino-5(S)-N-(N-methoxycarbonyl-(L)-iso-leucyl)amino-6-phenyl-2-azahexane Analogously to Example 7, 175 mg (0.92 mmol) of N-ethoxycarbonyl-(L)-valine, 332 mg (1.7 mmol) of EDC and 156 mg (1.15 mmol) of HOBT in 2.5 ml of DMF and 483 $\mu$l (3.47 mmol) of TEA are reacted with 0.578 mmol of 1-[4-(thiazol-5-yl)-phenyl]-4(S)-hydroxy-2-amino-5(S)-N-(N-methoxycarbonyl-(L)-iso-leucyl)amino-6-phenyl-2-azahexane (Example 11b) in 5.2 ml of DMF to form the title compound: m.p: 200–203° C.; HPLC$_{20\text{-}100}$: t$_{Ret}$=14.6; FAB MS (M+H)$^+$=711.

Example 15

1-[4-(Thiazol-5-yl)-phenyl]-4(S)-hydroxy-2-N-(N-methoxycarbonyl-(L)-S-methylcysteinyl)amino-5(S)-N-(N-methoxycarbonyl-(L)-iso-leucyl)amino-6-phenyl-2-azahexane Under an argon atmosphere, 0.5 mmol of 1-[4-(thiazol-5-yl)-phenyl]-4(S)-hydroxy-2-amino-5(S)-N-(N-methoxycarbonyl-(L)-iso-leucyl)amino-6-phenyl-2-azahexane (Example 11b) and 165 $\mu$l (1.5 mmol) of NMM in 4.8 ml of DMF are added with ice cooling to 116 mg (0.60 mmol) of N-methoxycarbonyl-(L)-S-methylcysteine (Example 5a) and 149 mg (0.50 mmol) of TPTU in 2.5 ml of DMF and the mixture is stirred at room temperature for 12 hours. Water and ethyl acetate are added; the aqueous phase is separated off and extracted a further 2× with ethyl acetate. The organic phases are washed with 2× with water and brine, dried (Na$_2$SO$_4$) and partially concentrated by evaporation. The addition of ether causes the title compound to crystallise: m.p: 179–181° C.; TLC: R$_f$=0.67 (methylene chloride/ethanol 10:1); HPLC$_{20\text{-}100}$: t$_{Ret}$=13.6; FAB MS (M+H)$^+$=715.

Example 16

1-[4-(Thiazol-2-yl)-phenyl]-4(S)-hydroxy-5(S)-2,5-bis[N-(N-methoxycarbonyl-(L)-tert-leucyl)amino]-6-phenyl-2-azahexane Under an argon atmosphere, 2.58 g (13.7 mmol) of N-methoxycarbonyl-(L)-tert-leucine and 4.09 g (13.7 mmol) of TPTU are dissolved in 15.5 ml of DMF; 5.7 ml (24.8 mmol) of Hünig base are added with cooling and the mixture is stirred for 10 min. Then a solution of 2.29 g (6.20 mmol) of 1-[4-(thiazol-2-yl)-phenyl]-4(S)-hydroxy-5(S)-2,5-diamino-6-phenyl-2-azahexane in 15.5 ml of DMF is added and the mixture is stirred at room temperature for 16 hours. The light-yellow reaction solution is poured into ice-water; ethyl acetate is added and the mixture is stirred for 30 min. The aqueous phase is separated off and extracted a further 2× with ethyl acetate. The organic phases are extracted 2× with water, sat. NaHCO$_3$ solution and 2× with brine, dried (Na$_2$SO$_4$) and concentrated by evaporation. Column chromatography (SiO$_2$; hexane/ethyl acetate 1:3) and crystallisation from methylene chloride/DIPE yield the title compound: TLC: R$_f$=0.18 (hexane/ethyl acetate 1:3); HPLC$_{20\text{-}100(12')}$: t$_{Ret}$=11.0; FAB MS (M+H)$^+$=711; [$\alpha$]$^0$.(c=0.6, ethanol)=–46°

The starting material is prepared as follows:

16a) 4-(Thiazol-2-yl)-benzaldehyde

Under argon, 9.2 g (379 mmol) of magnesium are placed in 84 ml of THF and heated to 60° C. A solution of 82.6 g (357 mmol) of 4-bromobenzaldehyde dimethyl acetal (for preparation see *J. Org. Chem.* 56, 4280 (1991)) in 677 ml of THF is added dropwise thereto within a period of 30 min and the mixture is stirred at boiling temperature for a further 40 min. The Grignard solution is cooled, decanted into a dropping funnel and added dropwise within a period of 30 min to a reddish suspension of 31.7 ml (338 mmol) of 2-bromothiazole (Fluka, Buchs, Switzerland) and 5.39 g (9.95 mmol) of DPPP in 1.68 liters of THF. The mixture is stirred at room temperature for 12 hours; a further 5.39 g of DPPP are added and the mixture is stirred for a further 7 hours. 840 ml of water are added and the mixture is stirred for 10 min; the THF is evaporated off using a rotary evaporator and the residue is stirred for 1.5 hours in 1.0 liter of ether and 340 ml of 2N HCl. The aqueous phase is separated off and extracted 2× with ethyl acetate. The organic phases are washed 2× with 0.5N HCl, water, sat. NaHCO$_3$ solution, water and brine, dried (Na$_2$SO$_4$) and concentrated by evaporation. Chromatography (SiO$_2$; hexane/ethyl acetate 4:1) and digestion in hexane yield the title compound: TLC: R$_f$=0.21 (hexane/ethyl acetate 3:1); m.p: 91–92° C.; Anal. (C$_{10}$H$_7$NOS) calc. C 63.47, H 3.73, N 7.40, S 16.94: found C 63.14, H 3.79, N 7.27, S 17.08; $^1$H-NMR (CDCl$_3$) $\delta$ 10.05 (s, HCO), 8.15 (d, J=8, 2H), 7.95 (m, 3H), 7.45 (d, J=3, 1H).

16b) N-1-(tert-Butoxycarbonyl)-N-2-{[4-(thiazol-2-yl)-phenyl]-methylidene}-hydrazone A solution of 27.6 g (145 mmol) of 4-(thiazol-2-yl)-benzaldehyde and 19.7 g (149 mmol) of tert-butyl carbazate in 920 ml of ethanol is stirred at 80° C. for 18 hours. Cooling, concentration by evaporation and stirring from DIPE yield the title compound: TLC: R$_f$=0.31 (toluene/ethyl acetate 3:1); HPLC$_{20\text{-}100}$: t$_{Ret}$=14.5.

16c) N-1-(tert-Butoxycarbonyl)-N-2-[4-(thiazol-2-yl)-benzyl]-hydrazine

Under a nitrogen atmosphere, 77.6 g (256 mmol) of N-1-(tert-butoxycarbonyl)-N-2-{[4-(thiazol-2-yl)-phenyl]-methylidene}-hydrazone are placed in 450 ml THF, and 16.9 g (257 mmol; 95%) of sodium cyanoborohydride are added. A solution of 49.6 g (261 mmol) of p-toluenesulfonic acid monohydrate in 450 ml of THF (pH 3–4) is added dropwise thereto.

After 17 hours, a further 3.38 g of sodium cyanoborohydride are added; the mixture is adjusted to pH 3–4 with p-toluenesulfonic acid monohydrate solution and stirred for 3 hours to complete the reaction. Water and ethyl acetate are added; the aqueous phase is separated off and extracted a further 2× with ethyl acetate. The organic phases are washed with brine, sat. NaHCO$_3$ solution and 2× brine, dried (Na$_2$SO$_4$) and concentrated by evaporation. The resulting viscous oil is taken up with 300 ml of 1,2-dichloroethane; 300 ml of 1N NaOH solution are slowly added (foams) and the mixture is boiled under reflux for 3.5 hours. The mixture is cooled and diluted with methylene chloride and water; the aqueous phase is separated off and extracted 2× with methylene chloride. The organic phases are dried (Na$_2$SO$_4$), concentrated by evaporation and chromatographed (SiO$_2$; toluene/acetone 9:1→6:1). Stirring in hexane yields the title compound: TLC: R$_f$=0.3 (hexane/ethyl acetate 3:2); HPLC$_{20-100}$: t$_{Ret}$=11.1.

16d) 1-[4-(Thiazol-2-yl)-phenyl]-4(S)-hydroxy-5(S)-2,5-bis[(tert-butoxycarbonyl)amino]-6-phenyl-2-azahexane A solution of 6.00 g (22.8 mmol) of (2R)-[(1'S)-Boc-amino-2'-phenylethyl]oxirane and 5.37 g (17.6 mmol) of N-1-(tert-butoxycarbonyl)-N-2-[4-(thiazol-2-yl)-benzyl]-hydrazine in 550 ml of iso-PrOH is heated at boiling overnight. The reaction mixture is cooled to room temperature, poured into 0.2 liter of water, with stirring, and cooled with ice. Filtration with suction, washing with water and ether and drying yield the title compound: TLC: R$_f$=0.36 (hexane/acetone 3:2); HPLC$_{20-100(12')}$: t$_{Ret}$=12.7. Further product can be isolated from the mother liquor by chromatography (SiO$_2$; hexane/acetone 3:2).

16e) 1-[4-(Thiazol-2-yl)-phenyl]-4(S)-hydroxy-5(S)-2,5-diamino-6-phenyl-2-azahexane A solution of 4.3 g (7.56 mmol) of 1-[4-(thiazol-2-yl)-phenyl]-4(S)-hydroxy-5(S)-2,5-bis[(tert-butoxycarbonyl) amino]-6-phenyl-2-azahexane in 378 ml of formic acid is stirred at room temperature for 3.5 hours (argon) and then concentrated by evaporation. Sat. NaHCO$_3$ solution and methylene chloride are added to the residue; the aqueous phase is separated off and extracted 2× with methylene chloride. The organic phases are treated with brine, dried (Na$_2$SO$_4$) and concentrated by evaporation to form the title compound: HPLC$_{20-100(12')}$: t$_{Ret}$=6.8.

Example 17
1-[4-(Thiazol-2-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane Under an argon atmosphere, 294 mg of 1-[4-(thiazol-2-yl)-phenyl]-4(S)-hydroxy-2-amino-5(S)-N-(N-methoxycarbonyl-(L)-valyl)amino-6-phenyl-2-azahexane and 165 μl (1.5 mmol) of NMM in 4.8 ml of DMF are added to 113.5 mg (0.60 mmol) of N-methoxycarbonyl-(L)-tert-leucine (Example 2e) and 149 mg (0.50 mmol) of TPTU in 2.5 ml of DMF at 0° C. and the mixture is stirred at room temperature for 18 hours. Water and ethyl acetate are added; the aqueous phase is separated off and extracted a further 2× with ethyl acetate. The organic phases are washed 2× with water, sat. NaHCO$_3$ solution, water and brine, dried (Na$_2$SO$_4$) and concentrated by evaporation. Column chromatography (SiO$_2$; methylene chloride/THF 4:1) and precipitation with hexane from a concentrated solution in methylene chloride yield the title compound: HPLC$_{20-100}$: t$_{Ret}$=14.5; FAB MS (M+H)$^{30}$ =697.

The starting material is prepared as follows:

17a) 1-[4-(Thiazol-2-yl)-phenyl]-4(S)-hydroxy-2-(tert-butoxycarbonyl)amino-5(S)-(trifluoroacetyl)amino-6-phenyl-2-azahexane With the exclusion of air, 4.8 g (18.5 mmol) of (2R)-[(1'S)-(trifluoroacetyl)amino-2'-phenyl-ethyl]oxirane and 3.78 g (12.4 mmol) of N-1-(tert-butoxycarbonyl)-N-2-[4-(thiazol-2-yl)-benzyl]-hydrazine (Example 16c) in 62 ml of iso-PrOH are heated at boiling for 10 hours. Cooling the reaction mixture, filtration and washing with ether yield the title compound: Anal. (C$_{27}$H$_{31}$N$_4$F$_3$O$_4$S) calc. C 57.44, H 5.53, N 9.92, F 10.09, S 5.68; found C 57.27, H 5.49, N 9.91, F 9.94, S 5.70; HPLC$_{20-100}$: t$_{Ret}$=16.9; FAB MS (M+H)$^+$= 565. Further product can be isolated from the filtrate by concentration by evaporation, column chromatography (SiO$_2$; methylene chloride/THF 25:1) and stirring from ether/ethyl acetate.

17b) 1-[4-(Thiazol-2-yl)-phenyl]-4(S)-hydroxy-2-(tert-butoxycarbonyl)amino-5(S)-amino-6-phenyl-2-azahexane 55 ml of a 1N K$_2$CO$_3$ solution are added dropwise to 3.12 g (5.5 mmol) of 1-[4-(thiazol-2-yl)-phenyl]-4(S)-hydroxy-2-(tert-butoxycarbonyl)amino-5(S)-(trifluoroacetyl)amino-6-phenyl-2-azahexane in 55 ml of methanol and the mixture is stirred at 70° C. for 9 hours. The mixture is cooled and ≈30 ml of methanol are evaporated off; methylene chloride and water are added and the aqueous phase is separated off and extracted with methylene chloride; the organic phases are washed with water, dried (Na$_2$SO$_4$) and concentrated by evaporation, yielding the title compound: HPLC$_{20-100}$: t$_{Ret}$= 11.9; FAB MS (M+H)$^+$=469.

17c) 1-[4-(Thiazol-2-yl)-phenyl]-4(S)-hydroxy-2-(tert-butoxycarbonyl)amino-5(S)-N-(N-methoxycarbonyl-(L)-valyl)amino-6-phenyl-2-azahexane Under a nitrogen atmosphere, 1.4 g (8.0 mmol) of N-methoxycarbonyl-(L)-valine, 2.87 g (15 mmol) of EDC and 1.35 g (10 mmol) of HOBT are dissolved in 22 ml of DMF. After 45 min, 4.2 ml (30 mmol) of TEA are added and then a solution of 2.34 g (5.0 mmol) of 1-[4-(thiazol-2-yl)-phenyl]-4(S)-hydroxy-2-(tert-butoxycarbonyl)amino-5(S)-amino-6-phenyl-2-azahexane in 45 ml of DMF is added dropwise. After 1.5 hours, the reaction mixture is concentrated by evaporation; the residue is taken up in methylene chloride and washed with water, sat. NaHCO$_3$ solution, water and brine. The aqueous phases are extracted 2× with methylene chloride; the combined organic phases are dried (Na$_2$SO$_4$) and concentrated by evaporation. Column chromatography (SiO$_2$; methylene chloride/ethyl acetate 2:1) and crystallisation from ethyl acetate/ether yield the title compound: m.p: 178–179° C.; HPLC$_{20-100}$: t$_{Ret}$=15.8.

17d) 1-[4-(Thiazol-2-yl)-phenyl]-4(S)-hydroxy-2-amino-5(S)-N-(N-methoxycarbonyl-(L)-valyl)amino-6-phenyl-2-azahexane 0.94 g (1.5 mmol) of 1-[4-(thiazol-2-yl)-phenyl]-4(S)-hydroxy-2-(tert-butoxycarbonyl)amino-5(S)-N-(N-methoxycarbonyl-(L)-valyl)amino-6-phenyl-2-azahexane and 18 ml of formic acid are stirred at room temperature for 6 hours and worked up analogously to Example 2d to form the title compound: FAB MS (M+H)$^+$=526.

Example 18
1-[4-(Thiazol-2-yl)-phenyl]-4(S)-hydroxy-2-N-(N-methoxycarbonyl-(L)-iso-leucyl)amino-5(S)-N-(N-methoxycarbonyl-(L)-valyl)amino-6-phenyl-2-azahexane Analogously to Example 7, 106 mg (0.56 mmol) of N-methoxycarbonyl-(L)-iso-leucine, 201 mg (1.05 mmol) of EDC and 95 mg (0.7 mmol) of HOBT in 4.6 ml of DMF and 293 μl (2.1 mmol) of TEA are reacted with 0.35 mmol of 1-[4-(thiazol-2-yl)-phenyl]-4(S)-hydroxy-2-amino-5(S)-N-(N-methoxycarbonyl-(L)-valyl)amino-6-phenyl-2-azahexane to form the title compound: m.p: 227–229° C.; HPLC$_{20-100}$: t$_{Ret}$=14.5; FAB MS (M+H)$^+$=697.

Example 19
1-[4-(Thiazol-2-yl)-phenyl]-4(S)-hydroxy-2-N-(N-ethoxycarbonyl-(L)-valyl)amino-5(S)-N-(N-methoxycarbonyl-(L)-valyl)amino-6-phenyl-2-azahexane Analogously to Example 7, 106 mg (0.56 mmol) of N-ethoxycarbonyl-(L)-valine, 201 mg (1.05 mmol) of EDC and 95 mg (0.7 mmol) of HOBT in 4.6 ml of DMF and 293 μl (2.1 mmol) of TEA are reacted with 0.35 mmol of 1-[4-(thiazol-2-yl)-phenyl]-4(S)-hydroxy-2-amino-5(S)-N-(N-methoxycarbonyl-(L)-valyl)amino-6-phenyl-2-azahexane to form the title compound: Anal. ($C_{35}H_{48}N_6O_7S$ (0.20 $H_2O$)) calc. C 60.01, H 6.96, N 12.00, S 4.58, $H_2O$ 0.51: found C 60.07, H 6.78, N 11.93, S 4.70, $H_2O$ 0.52; HPLC$_{20-100}$: t$_{Ret}$=14.6; FAB MS (M+H)$^+$=697.

Example 20
1-[4-(Thiazol-2-yl)-phenyl]-4(S)-hydroxy-5(S)-2,5-bis[N-(N-methoxycarbonyl-(L)-valyl)amino]-6-phenyl-2-azahexane Analogously to Example 7, 140 mg (0.80 mmol) of N-methoxycarbonyl-(L)-valine, 288 mg (1.5 mmol) of EDC and 135 mg (1.0 mmol) of HOBT in 2.2 ml of DMF and 418 μl (3.0 mmol) of TEA are reacted with 0.5 mmol of 1-[4-(thiazol-2-yl)-phenyl]-4(S)-hydroxy-2-amino-5(S)-N-(N-methoxycarbonyl-(L)-valyl)amino-6-phenyl-2-azahexane in 4.5 ml of DMF to form the title compound: m.p: 207–210° C.; HPLC$_{20-100}$: t$_{Ret}$=13.8; FAB MS (M+H)$^+$=683.

Example 21
1-[4-(Thiazol-2-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane Under an argon atmosphere, 294 mg of 1-[4-(thiazol-2-yl)-phenyl]-4(S)-hydroxy-2-amino-5(S)-N-(N-methoxycarbonyl-(L)-iso-leucyl)amino-6-phenyl-2-azahexane and 165 μl (1.5 mmol) of NMM in 4.8 ml of DMF are added to 113.5 mg (0.60 mmol) of N-methoxycarbonyl-(L)-tert-leucine (Example 2e) and 149 mg (0.50 mmol) of TPTU in 2.5 ml of DMF at 0° C. and the mixture is stirred at room temperature for 16 hours. Ice-water and ethyl acetate are added; the aqueous phase is separated off and extracted with ethyl acetate. The organic phases are washed 2× with water and brine, dried ($Na_2SO_4$) and concentrated by evaporation. Column chromatography ($SiO_2$; ethyl acetate) and crystallisation from ethyl acetate/ether/hexane yield the title compound: Anal. ($C_{36}H_{50}N_6O_7S$ (1.4% $H_2O$)) calc. C 59.97, H 7.15, N 11.66, S 4.45: found C 59.99, H 7.18, N 11.35, S 4.59; TLC: R$_f$=0.51 (methylene chloride/THF 3:1); HPLC$_{20-100}$: t$_{Ret}$=15.2; FAB MS (M+H)$^+$=711.

The starting material is prepared as follows:

21a) 1-[4-(Thiazol-2-yl)-phenyl]-4(S)-hydroxy-2-(tert-butoxycarbonyl)amino-5(S)-N-(N-methoxycarbonyl-(L)-iso-leucyl)amino-6-phenyl-2-azahexane Under a nitrogen atmosphere, 938 mg (4.96 mmol) of N-methoxycarbonyl-(L)-iso-leucine, 1.78 g (9.3 mmol) of EDC and 838 mg (6.2 mmol) of HOBT are dissolved in 13.7 ml of DMF. After 30 min, 2.6 ml (18.6 mmol) of TEA are added and then a solution of 1.45 g (3.1 mmol) of 1-[4-(thiazol-2-yl)-phenyl]-4(S)-hydroxy-2-(tert-butoxycarbonyl)amino-5(S)-amino-6-phenyl-2-azahexane (Example 17b) in 28 ml of DMF is added dropwise thereto. After 3 hours the reaction mixture is concentrated by evaporation; the residue is taken up in ethyl acetate and a small amount of THF and washed with water, sat. $NaHCO_3$ solution, water and brine. The aqueous phases are extracted with ethyl acetate; the combined organic phases are dried over $Na_2SO_4$ and concentrated by evaporation. Column chromatography ($SiO_2$; methylene chloride/THF 5:1) and stirring from ethyl acetate/DIPE yield the title compound: HPLC$_{20-100}$: t$_{Ret}$=16.3; FAB MS (M+H)$^+$=640.

21b) 1-[4-(Thiazol-2-yl)-phenyl]-4(S)-hydroxy-2-amino-5(S)-N-(N-methoxycarbonyl-(L)-iso-leucyl)amino-6-phenyl-2-azahexane 761 mg (1.2 mmol) of 1-[4-(thiazol-2-yl)-phenyl]-4(S)-hydroxy-2-(tert-butoxycarbonyl)amino-5(S)-N-(N-methoxycarbonyl-(L)-iso-leucyl)amino-6-phenyl-2-azahexane and 12 ml of formic acid are stirred at room temperature for 7 hours and worked up analogously to Example 2d to form the title compound.

Example 22
1-[4-(Thiazol-2-yl)-phenyl]-4(S)-hydroxy-2-N-(N-ethoxycarbonyl-(L)-valyl)amino-5(S)-N-(N-methoxycarbonyl-(L)-iso-leucyl)amino-6-phenyl-2-azahexane Under an argon atmosphere, 321 mg (0.60 mmol) of 1-[4-(thiazol-2-yl)-phenyl]-4(S)-hydroxy-2-amino-5(S)-N-(N-methoxycarbonyl-(L)-iso-leucyl)amino-6-phenyl-2-azahexane (Example 21b) and 182 mg (1.8 mmol) of NMM in 5.8 ml of DMF are added to 136 mg (0.72 mmol) of N-ethoxycarbonyl-(L)-valine and 178 mg (0.60 mmol) of TPTU in 3 ml of DMF and the mixture is stirred at room temperature for 15 hours. The reaction mixture is poured into ice-water, stirred for 30 min and filtered. Crystallisation from THF with DIPE and hexane yields the title compound: m.p.: 209–211° C.; HPLC$_{20-100}$: t$_{Ret}$=15.2; FAB MS (M+H)$^+$=711.

Example 23
1-[4-(Thiazol-2-yl)-phenyl]-4(S)-hydroxy-2-N-(N-methoxycarbonyl-(L)-valyl)amino-5(S)-N-(N-methoxycarbonyl-(L)-iso-leucyl)amino-6-phenyl-2-azahexane Under an argon atmosphere, 321 mg (0.60 mmol) of 1-[4-(thiazol-2-yl)-phenyl]-4(S)-hydroxy-2-amino-5(S)-N-(N-methoxycarbonyl-(L)-iso-leucyl)amino-6-phenyl-2-azahexane (Example 21b) and 182 mg (1.8 mmol) of NMM in 5.8 ml of DMF are added to 126 mg (0.72 mmol) of N-methoxycarbonyl-(L)-valine and 178 mg (0.60 mmol) of TPTU in 3 ml of DMF; the mixture is stirred at room temperature for 15 hours and worked up analogously to Example 3. TLC: R$_f$=0.15 (methylene chloride/THF 4:1); HPLC$_{20-100}$: t$_{Ret}$=14.5; FAB MS (M+H)$^+$=697.

Example 24
1-[4-(Thiazol-2-yl)-phenyl]-4(S)-hydroxy-2-N-(N-methoxycarbonyl-(L)-S-methylcysteinyl)amino-5(S)-N-(N-methoxycarbonyl-(L)-iso-leucyl)amino-6-phenyl-2-azahexane Under an argon atmosphere, 303 mg (0.50 mmol) of 1-[4-(thiazol-2-yl)-phenyl]-4(S)-hydroxy-2-amino-5(S)-N-(N-methoxycarbonyl-(L)-iso-leucyl)amino-6-phenyl-2-azahexane (Example 21b) and 165 μl (1.5 mmol) of NMM in 5 ml of DMF are added to 116 mg (0.60 mmol) of N-methoxycarbonyl-(L)-S-methylcysteine (Example 5a)

and 149 mg (0.50 mmol) of TPTU in 2.5 ml of DMF with ice-cooling and the mixture is stirred at room temperature for 4 hours. The mixture is poured into ice-water, stirred for 30 min and extracted 2× with ethyl acetate. The organic phases are washed with 2× with water, sat. NaHCO$_3$ solution, 2× with water and brine, dried (Na$_2$SO$_4$) and concentrated by evaporation. Column chromatography (SiO$_2$; methylene chloride/ethanol 20:1) and stirring from DIPE yield the title compound: TLC: R$_f$=0.39 (methylene chloride/methanol 10:1); HPLC$_{20\text{-}100}$: t$_{Ret}$=14.0; FAB MS (M+H)$^+$=715.

Example 25

1-{4-[2-(1-Methyl-1-phenyl-ethyl)-2H-tetrazol-5-yl]-phenyl}-4(S)-hydroxy-5(S)-2,5-bis[N-(N-methoxycarbonyl-(L)-tert-leucyl)amino]-6-phenyl-2-azahexane With the exclusion of air, 261 mg (1.38 mmol) of N-methoxycarbonyl-(L)-tert-leucine (Example 2e), 496 mg (2.58 mmol) of EDC and 232 mg (1.72 mmol) of HOBT are dissolved in 7.5 ml of DMF. After 15 min, 0.72 ml (5.17 mmol) of TEA and 585 mg (0.86 mmol) of 1-{4-[2-(1-methyl-1-phenyl-ethyl)-2H-tetrazol-5-yl]-phenyl}-4(S)-hydroxy-2-amino-5(S)-N-(N-methoxycarbonyl-(L)-tert-leucyl)amino-6-phenyl-2-azahexane hydrochloride in 3.5 ml of DMF are added. After 20 hours, the mixture is concentrated by evaporation and water and methylene chloride are added to the residue; the aqueous phase is separated off and extracted 2× more with methylene chloride. The organic phases are washed with 10% citric acid solution, sat. NaHCO$_3$ solution, water and brine, dried (Na$_2$SO$_4$) and concentrated by evaporation. Precipitation from a concentrated solution in ethyl acetate with DIPE/hexane yields the title compound: HPLC$_{20\text{-}100}$: t$_{Ret}$=17.5; FAB MS (M+H)$^+$=814.

The starting material is prepared as follows:

25a) 4-(Tetrazol-5-yl)-benzaldehyde 20.0 g (0.47 mol) of lithium chloride and 20.5 g (0.315 mol) of sodium azide are added to 41.2 g (0.315 mol) of 4-cyano-benzaldehyde (Fluka, Buchs, Switzerland) in 310 ml of methoxyethanol (Fluka, Buchs, Switzerland) and the mixture is heated at boiling for 6 hours (argon atmosphere). The cooled reaction mixture is poured into 1 liter of ice/37% HCl 10:1 and stirred thoroughly to complete the reaction. Filtration and washing with water yield the title compound: m.p.: 180–182° C.; $^1$H-NMR (DMSO-d$_6$) δ 10.11 (s, HCO), 8.29 and 8.14 (2d, J=8, each 2H).

25b) 4-[2-(1-Methyl-1-phenyl-ethyl)-2H-tetrazol-5-yl]-benzaldehyde

Under a nitrogen atmosphere, a solution of 6.9 g (58 mmol) of 2-phenyl-propene (Fluka, Buchs, Switzerland) and 22 ml of toluene is added dropwise to 10 g (57 mmol) of 4-(tetrazol-5-yl)-benzaldehyde and 1 g (5.7 mmol) of methanesulfonic acid in 44 ml of boiling toluene and the mixture is then stirred under reflux conditions for 1 hour. The cooled reaction mixture is washed 2× with sat. NaHCO$_3$ solution, water and brine, dried (Na$_2$SO$_4$) and concentrated by evaporation to form the title compound: $^1$H-NMR (DMSO-d$_6$) δ 10.09 (s, HCO), 8.29 and 8.08 (2d, J=8, each 2H), 7.33 and 7.17 (2m, 5H), 2.17 (s, 6H).

25c) N-1-(tert-Butoxycarbonyl)-N-2-{4-[2-(1-methyl-1-phenyl-ethyl)-2H-tetrazol-5-yl]-phenyl-methylidene}-hydrazone 13.0 g (42 mmol) of 4-[2-(1-methyl-1-phenyl-ethyl)-2H-tetrazol-5-yl]-benzaldehyde and 5.98 g (45.2 mmol) of tert-butyl carbazate in 300 ml of ethanol are stirred at 80° C. for 20 hours. The reaction mixture is then concentrated to half by evaporation; 420 ml of water are added and the mixture is extracted 3× with ethyl acetate. The organic phases are washed 2× with sat. NaHCO$_3$ solution and brine, dried (Na$_2$SO$_4$) and concentrated by evaporation to form the title compound: HPLC$_{20\text{-}100}$: t$_{Ret}$=17.7.

25d) N-1-(tert-Butoxycarbonyl)-N-2-{4-[2-(1-methyl-1-phenyl-ethyl)-2H-tetrazol-5-yl]-benzyl}-hydrazine Under a nitrogen atmosphere, 11.6 g (28.5 mmol) of N-1-(tert-butoxycarbonyl)-N-2-{4-[2-(1-methyl-1-phenyl-ethyl)-2H-tetrazol-5-yl]-phenyl-methylidene}-hydrazone are placed in 140 ml of THF, and 2.32 g (31.3 mmol; 85%) of sodium cyanoborohydride are added. A solution of 5.42 g (28.5 mmol) of p-toluenesulfonic acid monohydrate in 90 ml of THF is added dropwise thereto. After 4 hours, the mixture is concentrated by evaporation; the residue is taken up in ethyl acetate and washed with sat. NaHCO$_3$ solution and brine. The aqueous phases are extracted 2× with ethyl acetate; the organic phases are dried (Na$_2$SO$_4$) and concentrated by evaporation. The residue is taken up in 250 ml of methanol and 125 ml of THF, 37 g of K$_2$B$_4$O$_7$×H$_2$O in 125 ml of water are added, with cooling, and the mixture is stirred overnight. The mixture is partially concentrated by evaporation using a rotary evaporator and is diluted with methylene chloride and water; the aqueous phase is separated off and extracted 2× with methylene chloride. The organic phases are dried (Na$_2$SO$_4$) and concentrated by evaporation to form the title compound: HPLC$_{20\text{-}100}$: t$_{Ret}$=16.4.

25e) 1-{4-[2-(1-Methyl-1-phenyl-ethyl)-2H-tetrazol-5-yl]-phenyl}-4(S)-hydroxy-2-(tert-butoxycarbonyl)amino-5(S)-(trifluoroacetyl)amino-6-phenyl-2-azahexane A mixture of 6.05 g (23.4 mmol) of (2R)-[(1'S)-(trifluoroacetyl)amino-2'-phenylethyl]oxirane and 9.54 g (23.4 mmol) of N-1-(tert-butoxycarbonyl)-N-2-{4-[2-(1-methyl-1-phenyl-ethyl)-2H-tetrazol-5-yl]-benzyl}-hydrazine in 200 ml of iso-PrOH is heated at 90° C. for 24 hours. Concentration by evaporation, chromatography (SiO$_2$; methylene chloride/ether 20:1) and crystallisation from MeOH yield the title compound: Anal. (C$_{34}$H$_{40}$N$_7$O$_4$F$_3$) calc. C 61.16, H 6.04, N 14.68; found C 61.37, H 6.02, N 14.80.

25f) 1-{4-[2-(1-Methyl-1-phenyl-ethyl)-2H-tetrazol-5-yl]-phenyl}-4(S)-hydroxy-2-(tert-butoxycarbonyl)amino-5(S)-amino-6-phenyl-2-azahexane 28 ml of a 1N K$_2$CO$_3$ solution are added dropwise, at 70° C., to 1.9 g (2.8 mmol) of 1-{4-[2-(1-methyl-1-phenyl-ethyl)-2H-tetrazol-5-yl]-phenyl}-4(S)-hydroxy-2-(tert-butoxycarbonyl)amino-5(S)-(trifluoroacetyl)amino-6-phenyl-2-azahexane in 29 ml of methanol and the mixture is stirred for 15 hours. After cooling and concentration by evaporation, methylene chloride and water and added; the aqueous phase is separated off and extracted with methylene chloride. The organic phases are washed with water, dried (Na$_2$SO$_4$) and concentrated by evaporation to yield the title compound: HPLC$_{20\text{-}100}$: t$_{Ret}$=15.1; FAB MS (M+H)$^+$=469.

25g) 1-{4-[2-(1-Methyl-1-phenyl-ethyl)-2H-tetrazol-5-yl]-phenyl}-4(S)-hydroxy-2-(tert-butoxycarbonyl)amino-5(S)-N-(N-methoxycarbonyl-(L)-tert-leucyl)amino-6-phenyl-2-azahexane With the exclusion of air, 868 mg (4.59 mmol) of N-methoxycarbonyl-(L)-tert-leucine (Example 2e), 1.64 g (8.58 mmol) of EDC and 773 mg (5.72 mmol) of HOBT are dissolved in 24.5 ml of DMF. After 15 min, 2.39 ml (17.2 mmol) of TEA and 1.64 g (2.86 mmol) of 1-{4-[2-(1-methyl-1-phenyl-ethyl)-2H-tetrazol-5-yl]-phenyl}-4(S)-hydroxy-2-(tert-butoxycarbonyl)amino-5(S)-amino-6-phenyl-2-azahexane in 12 ml of DMF are added. After 20 hours, the mixture is concentrated by evaporation, and water and methylene chloride are added to the residue; the aqueous phase is separated off and extracted 2× more with methylene chloride. The organic phases are washed with 10% citric acid solution, sat. NaHCO$_3$ solution, water and brine, dried (Na$_2$SO$_4$) and concentrated by evaporation. Digestion from DIPE yields the title compound: HPLC$_{20-100}$: $t_{Ret}$=18.6; FAB MS (M+H)$^+$=743.

25h) 1-{4-[2-(1-Methyl-1-phenyl-ethyl)-2H-tetrazol-5-yl]-phenyl}-4(S)-hydroxy-2-amino-5(S)-N-(N-methoxycarbonyl-(L)-tert-leucyl)amino-6-phenyl-2-azahexane hydrochloride Under a nitrogen atmosphere, 1.37 g (1.84 mmol) of 1-{4-[2-(1-methyl-1-phenyl-ethyl)-2H-tetrazol-5-yl]-phenyl}-4(S)-hydroxy-2-(tert-butoxycarbonyl)amino-5(S)-N-(N-methoxycarbonyl-(L)-tert-leucyl)amino-6-phenyl-2-azahexane are stirred in 64 ml of acetonitrile and 64 ml of aqueous 2N HCl at room temperature for 6 days. The reaction mixture is filtered, and the filtrate is concentrated by evaporation under a high vacuum at room temperature and is finally lyophilised from dioxane to yield the title compound: HPLC$_{20-100}$: $t_{Ret}$=14.2; $^1$H-NMR (CD$_3$OD) inter alia δ 8.10 (d, J=8, 2H$^{arom}$), 7.8 (m, 1H$^{arom}$), 7.53 (m, 2H$^{arom}$), 7.32 (m, 3H$^{arom}$), 7.17 (m, 6H$^{arom}$), 2.23 (s, 2H$^3$C$^{tetrazole-protecting\ group}$).

Example 26
1-[4-(Tetrazol-5-yl)-phenyl]-4(S)-hydroxy-5(S)-2,5-bis[N-(N-methoxycarbonyl-(L)-tert-leucyl)amino]-6-phenyl-2-azahexane 34.5 ml of an 80% aqueous H$_2$SO$_4$ solution are added to 345.6 mg (0.424 mmol) of 1-{4-[2-(1-methyl-1-phenyl-ethyl)-2H-tetrazol-5-yl]-phenyl}-4(S)-hydroxy-5(S)-2,5-bis[N-(N-methoxycarbonyl-(L)-tert-leucyl)amino]-6-phenyl-2-azahexane, with ice-cooling. After stirring for 75 min, the mixture is poured into 800 ml of ice-water and extracted 3× with ethyl acetate. The organic phases are washed 3× with water and brine, dried (Na$_2$SO$_4$) and concentrated by evaporation. Column chromatography (SiO$_2$; ethyl acetate/ethanol 8:1→2:1) yields the title compound: TLC: $R_f$=0.38 (ethyl acetate/ethanol 2:1); HPLC$_{20-100}$: $t_{Ret}$=12.5; FAB MS (M+H)$^+$=696.

Example 27
1-[4-(2-Methyl-2H-tetrazol-5-yl)-phenyl]-4(S)-hydroxy-5(S)-2,5-bis[N-(N-methoxycarbonyl-(L)-tert-leucyl)amino]-6-phenyl-2-azahexane (and 1-methyl-1H-tetrazolyl isomer)

Under a nitrogen atmosphere, 100 mg (0.144 mmol) of 1-[4-(tetrazol-5-yl)-phenyl]-4(S)-hydroxy-5(S)-2,5-bis[N-(N-methoxycarbonyl-(L)-tert-leucyl)amino]-6-phenyl-2-azahexane are dissolved in 1 ml of DMF/dioxane 1:1 and, at 0° C., 73.2 mg (0.224 mmol) of Cs$_2$CO$_3$ and 6.9 μl (0.111 mmol) of methyl iodide in 1 ml of dioxane are added. The mixture is allowed to warm up slowly to room temperature overnight and a further 1 equivalent of Cs$_2$CO$_3$ and of methyl iodide are added. After stirring for a further 4 hours at room temperature, the mixture is diluted with ethyl acetate and 1N sodium hydroxide solution. The aqueous phase is separated off and extracted 2× with ethyl acetate. The organic phases are washed 2× with water and brine, dried (Na$_2$SO$_4$) and concentrated by evaporation. Column chromatography (SiO$_2$; methylene chloride/ethyl acetate 1:1→1:2) yields the pure title compound A (≈3 parts), followed by 1-[4-(1-methyl-1H-tetrazol-5-yl)-phenyl]-4(S)-hydroxy-5(S)-2,5-bis[N-(N-methoxycarbonyl-(L)-tert-leucyl)amino]-6-phenyl-2-azahexane (B) (≈1 part): A: TLC: $R_f$=0.26 (methylene chloride/ethyl acetate 1:1); HPLC$_{20-100}$: $t_{Ret}$=14.2; FAB MS (M+H)$^+$=710. B: TLC: $R_f$=0.09 (methylene chloride/ethyl acetate 1:1); HPLC$_{20-100}$: $t_{Ret}$=13.3; FAB MS (M+H)$^+$=710.

Alternative synthesis of the title compound:

Under a nitrogen atmosphere, 14.56 g (77 mmol) of N-methoxycarbonyl-(L)-tert-leucine and 22.87 g (77 mmol) of TPTU are stirred in 77 ml of DMF and 37.3 ml (218 mmol) of Hünig base at room temperature for 30 min. The reaction mixture is then added dropwise to an ice-cooled solution of 35.2 mmol of 1-[4-(2-methyl-2H-tetrazol-5-yl)-phenyl]-4(S)-hydroxy-5(S)-2,5-diamino-6-phenyl-2-azahexane dihydrochloride in 77 ml of DMF. After stirring at room temperature for 15 hours, the reaction mixture is partially concentrated by evaporation and the residue (≈80 ml) is poured into 5 liters of water; the mixture is stirred for 30 min and the crude product is filtered off. Dissolution in 90 ml of boiling ethanol, addition of 600 ml of DIPE and cooling yield the title compound: m.p.: 191–192° C.; [α]$_D$=−46° (c=0.5; ethanol).

The starting material is prepared as follows:

27a) 4-(2- Methyl-2H-tetrazol-5-yl)-benzaldehyde

With ice-cooling, a solution of 75.5 g (0.434 mol) of 4-(tetrazol-5-yl)-benzaldehyde (Example 25a) in 550 ml of DMF/dioxane 1:1 is added dropwise to 179.7 g (1.30 mol) of K$_2$CO$_3$ in 200 ml of DMF/dioxane 1:1; the mixture is stirred for 30 min and then 40 ml (0.64 mol) of methyl iodide are added. The mixture is stirred in an ice bath for 3 hours and, finally, at room temperature for 15 hours; the reaction mixture is poured into 2.8 liters of ice-water and stirred for 10 min; the title compound is filtered off and washed with water: m.p.: 137–139° C.; $^1$H-NMR (CD$_3$OD/CDCl$_3$) d 10.05 (s, HCO), 8.29 and 8.03 (2d, J=8, each 2H), 4.43 (s, 3H).

27b) N-1-(tert-Butyloxycarbonyl)-N-2-[4-(2-methyl-2H-tetrazol-5-yl)-phenyl-methylidene]-hydrazone 75.0 g (0.40 mol) of 4-(2-methyl-2H-tetrazol-5-yl)-benzaldehyde and 56.4 g (0.426 mol) of tert-butyl carbazate in 1400 ml of iso-PrOH are stirred at 90° C. for 24 hours, 2.2 liters of water are added to the cooled reaction mixture and the mixture is stirred thoroughly to complete the reaction; the title compound is filtered off and washed with water: m.p.: 195–197° C.; Anal. (C$_{14}$H$_{18}$N$_6$O$_2$) calc. C 55.62, H 6.00, N 27.80: found C 55.50, H 5.93, N 27.61.

27c) N-1-(tert-Butyloxycarbonyl)-N-2-[4-(2-methyl-2H-tetrazol-5-yl)-benzyl]-hydrazine Under a nitrogen atmosphere, 30.0 g (99.2 mmol) of N-1-(tert-butyloxycarbonyl)-N-2-[4-(2-methyl-2H-tetrazol-5-yl)-phenyl-methylidene]-hydrazone are placed in 350 ml of THF, and 8.79 g (119 mmol; 85%) of NaCNBH$_3$ are added. A solution of 22.6 g (119 mmol) of ρ-toluenesulfonic acid monohydrate in 175 ml of THF is added dropwise thereto (→precipitation). After 2 hours, the solid is filtered off, washed thoroughly with ethyl acetate and discarded. Water and ethyl acetate are added to the filtrate; the aqueous phase is separated off and extracted 2× more with ethyl acetate. The organic phases are washed with sat. NaHCO$_3$ solution, water and brine, dried (Na$_2$SO$_4$) and concentrated by evaporation. The resulting crystals are taken up in 417 ml of methanol and 208 ml of THF, and a solution of 127 g (415 mmol) of K$_2$B$_4$O$_7$.4H$_2$O in 417 ml of H$_2$O is added dropwise (→production of foam). The mixture is stirred at room temperature overnight, poured into 2.2 liters of water and extracted 3× with ethyl acetate. The organic phases are washed with sat. NaHCO$_3$ solution, water and brine, dried (Na$_2$SO$_4$) and concentrated by evaporation. The crude product is combined with material from a second, identical batch and filtered through silica gel using methylene chloride/THF 10:1 as the eluant. Concentration by evaporation to a residual volume of about 0.1 liters and addition of 150 ml of DIPE yield the crystalline title compound (which, alternatively, may also be obtained by catalytic hydrogenation of N-1-(Boc)-N-2-[4-(2-methyl-2H-tetrazol-5-yl)-phenyl-methylidene]-hydrazone with Lindlar catalyst in methanol): m.p.: 100–102° C.; TLC: $R_f$=0.47 (methylene chloride/THF 10:1); $^1$H-NMR (CD$_3$OD) d 8.06 and 7.52 (2d, J=8, each 2H), 4.42 (s, 3H); 4.00 (s, 2H); 1.44 (s, 9H); HPLC$_{20-100}$: $t_{Ret}$=10.2.

27d) 1-[4-(2-Methyl-2H-tetrazol-5-yl)-phenyl]-4(S)-hydroxy-5(S)-2,5-bis[(tert-butyloxycarbonyl)amino]-6-phenyl-2-azahexane 36.33 g (138 mmol) of (2R)-[(1'S)-Boc-amino-2'-phenylethyl]oxirane and 38.17 g (125 mmol) of N-1-(tert-butyloxycarbonyl)-N-2-[4-(2-methyl-2H-tetrazol-5-yl)-benzyl]-hydrazine are heated in 964 ml of iso-PrOH at 90° C. for 20 hours. The crystallised title compound can be separated from the cooled reaction mixture by filtration. Further product crystallises out of the filtrate after the addition of 1.2 liters of water: m.p.: 175–178° C.; TLC: $R_f$=0.22 (methylene chloride/ethyl acetate 6:1); HPLC$_{20-100}$: $t_{Ret}$=16.9.

27e) 1-[4-(2-Methyl-2H-tetrazol-5-yl)-phenyl]-4(S)-hydroxy-5(S)-2,5-diamino-6-phenyl-2-azahexane dihydrochloride 93 ml of 4N aqueous hydrochloride acid solution are added to a solution of 20.0 g (35.2 mmol) of 1-[4-(2-methyl-2H-tetrazol-5-yl)-phenyl]-4(S)-hydroxy-5(S)-2,5-bis[(tert-butyloxycarbonyl)amino]-6-phenyl-2-azahexane in 279 ml of THF. The mixture is stirred at 50° C. for 8 hours and then concentrated gently by evaporation (room temperature; high vacuum). The oily residue is taken up 3× more in ethanol and again concentrated by evaporation, yielding the crystalline title compound. In order to determine the analytical data, 1 g of the crude product was stirred in 6 ml of hot iso-PrOH, 6 ml of DIPE was added, and cooling and separation by filtration were carried out: m.p.: 227–230° C.; HPLC$_{20-100}$: $t_{Ret}$=7.4; Anal. (C$_{19}$H$_{25}$N$_7$O.2HCl(+0.20 H$_2$O)) calc. C 51.40, H 6.22, N 22.08, Cl 15.97, H$_2$O 0.81: found C 51.50, H 6.33, N 22.28, Cl 15.88, H$_2$O 0.80.

Example 28
1-{4-[2-(1-Methyl-1-phenyl-ethyl)-2H-tetrazol-5-yl]-phenyl}-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane With the exclusion of air, 261 mg (1.38 mmol) of N-methoxycarbonyl-(L)-iso-leucine, 496 mg (2.58 mmol) of EDC and 232 mg (1.72 mmol) of HOBT are dissolved in 7.5 ml of DMF. After 15 min, 0.72 ml (5.17 mmol) of TEA and 585 mg (0.86 mmol) of 1-{4-[2-(1-methyl-1-phenyl-ethyl)-2H-tetrazol-5-yl]-phenyl}-4(S)-hydroxy-2-amino-5(S)-N-(N-methoxycarbonyl-(L)-tert-leucyl)amino-6-phenyl-2-azahexane hydrochloride (Example 25h) in 3.5 ml of DMF are added. After 20 hours, the mixture is worked up as described under Example 25i. Precipitation with DIPE from a concentrated solution in methylene chloride yields the title compound: HPLC$_{20-100}$: $t_{Ret}$=17.5; FAB MS (M+H)$^+$=814.

Example 29
1-[4-(Tetrazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane 35 ml of an 80% aqueous H$_2$SO$_4$ solution are added to 354 mg (0.435 mmol) of 1-{4-[2-(1-methyl-1-phenyl-ethyl)-2H-tetrazol-5-yl]-phenyl}-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane, with ice-cooling. After stirring for 75 min, the mixture is worked up analogously to Example 26 to yield the title compound: HPLC$_{20-100}$: $t_{Ret}$=12.6; FAB MS (M+H)$^+$=696.

Example 30
1-[4-(2-Methyl-2H-tetrazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane Under a nitrogen atmosphere, 72 mg (0.103 mmol) of 1-[4-(tetrazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino]-6-phenyl-2-azahexane are dissolved in 0.5 ml of DMF and, at 0° C., 71 mg (0.217 mmol) of Cs$_2$CO$_3$ and 6.9 µl (0.111 mmol) of methyl iodide in 1 ml of dioxane are added. The mixture is allowed to warm up slowly to room temperature overnight and is then diluted with ethyl acetate and 1N sodium hydroxide solution. The aqueous phase is separated off and extracted 2× with ethyl acetate. The organic phases are washed 2× with water and brine, dried (Na$_2$SO$_4$) and concentrated by evaporation to yield title compound A, which additionally contains ≈20% 1-[4-(1-methyl-1H-tetrazol-5-yl)-phenyl]-4(S)-hydroxy-2-N-(N-methoxycarbonyl-(L)-iso-leucyl)amino-5(S)-N-(N-methoxycarbonyl-(L)-tert-leucyl)amino-6-phenyl-2-azahexane (B): HPLC$_{20-100}$A: $t_{Ret}$=14.3; HPLC$_{20-100}$B: $t_{Ret}$=13.3; FAB MS (M+H)$^+$=710.

Example 31
1-{4-[2-(1-Methyl-1-phenyl-ethyl)-2H-tetrazol-5-yl]-phenyl}-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane With the exclusion of air, 128 mg (0.67 mmol) of N-methoxycarbonyl-(L)-tert-leucine (Example 2e), 243 mg (1.27 mmol) of EDC and 114 mg (0.84 mmol) of HOBT are dissolved in 2 ml of DMF. After 15 min, 0.35 ml (2.5 mmol) of TEA and 286 mg (0.42 mmol) of 1-{4-[2-(1-methyl-1-phenyl-ethyl)-2H-tetrazol-5-yl]-phenyl}-4(S)-hydroxy-2-amino-5(S)-N-(N-methoxycarbonyl-(L)-iso-leucyl)amino-6-phenyl-2-azahexane hydrochloride in 1.5 ml of DMF are added. After 20 hours, the mixture is worked up as described under Example 25. Chromatography (SiO$_2$; ethyl acetate/toluene/methylene chloride 2:1:1) yields the title compound: TLC: $R_f$=0.22 (methylene chloride/ethyl acetate 1:1); HPLC$_{20-100}$: $t_{Ret}$=17.3; FAB MS (M+H)$^+$=814.

The starting materials are prepared as follows:

31a) 1-{4-[2-(1-Methyl-1-phenyl-ethyl)-2H-tetrazol-5-yl]-phenyl}-4(S)-hydroxy-2-(tert-butoxycarbonyl)amino-5(S)-N-(N-methoxycarbonyl-(L)-iso-leucyl)amino-6-phenyl-2-azahexane With the exclusion of air, 270 mg (1.43 mmol) of N-methoxycarbonyl-(L)-iso-leucine, 513 mg (2.67 mmol) of EDC and 241 mg (1.78 mmol) of HOBT are dissolved in 7.8 ml of DMF. After stirring for 15 min, 0.75 ml (5.4 mmol) of TEA and 510 mg (0.89 mmol) of 1-{4-[2-(1-methyl-1-phenyl-ethyl)-2H-tetrazol-5-yl]-phenyl}-4(S)-hydroxy-2-(tert-butoxycarbonyl)amino-5(S)-amino-6-phenyl-2-azahexane (Example 25f) in 3.7 ml of DMF are added. After 20 hours, the mixture is worked up analogously to Example 25g to yield the title compound: HPLC$_{20-100}$: $t_{Ret}$=18.5; FAB MS (M+H)$^+$=743.

31b) 1-{4-[2-(1-Methyl-1-phenyl-ethyl)-2H-tetrazol-5-yl]-phenyl}-4(S)-hydroxy-2-amino-5(S)-N-(N-methoxycarbonyl-(L)-iso-leucyl)amino-6-phenyl-2-azahexane hydrochloride Under a nitrogen atmosphere, 317 mg (0.43 mmol) of 1-{4-[2-(1-methyl-1-phenyl-ethyl)-2H-tetrazol-5-yl]- phenyl}-4(S)-hydroxy-2-(tert-butoxycarbonyl)amino-5(S)-N-(N-methoxycarbonyl-(L)-iso-leucyl)amino-6-phenyl-2-azahexane in 15 ml of acetonitrile and 15 ml of 2N HCl are stirred at 50° C. for 20 hours and worked up analogously to Example 25h to form the title compound: HPLC$_{20\text{-}100}$: t$_{Ret}$=14.4.

Example 32

1-[4-(Tetrazol-5-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane Analogously to Example 26, 1-{4-[2-(1-methyl-1-phenyl-ethyl)-2H-tetrazol-5-yl]-phenyl}-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane is deprotected with 80% sulfuric acid to form the title compound.

Example 33

1-[4-(2-Methyl-2H-tetrazol-5-yl)-phenyl]-4(S)-hydroxy-2-N-(N-methoxycarbonyl-(L)-tert-leucyl)amino-5(S)-N-(N-methoxycarbonyl-(L)-iso-leucyl)amino-6-phenyl-2-azahexane Analogously to Example 30, 1- [4-(tetrazol-5-yl)-phenyl]-4(S)-hydroxy-2-N-(N-methoxycarbonyl-(L)-tert-leucyl)amino-5(S)-N-(N-methoxycarbonyl-(L)-iso-leucyl)amino]-6-phenyl-2-azahexane in DMF/dioxane is methylated with Cs$_2$CO$_3$ and methyl iodide.

Example 34

1-[4-(2-tert-Butyl-2H-tetrazol-5-yl)-phenyl]-4(S)-hydroxy-5(S)-2,5-bis[N-(N-methoxycarbonyl-(L)-tert-leucyl)amino]-6-phenyl-2-azahexane Under a nitrogen atmosphere, 54 mg (0.28 mmol) of N-methoxycarbonyl-(L)-tert-leucine and 84 mg (0.28 mmol) of TPTU in 1 ml of DMF and 94 μl (0.85 mmol) of NMM are stirred at room temperature for 10 min. 175 mg (0.283 mmol) of 1-[4-(2-tert-butyl-2H-tetrazol-5-yl)-phenyl]-4(S)-hydroxy-5(S)-amino-2-N-[N-methoxycarbonyl-(L)-tert-leucyl]amino-6-phenyl-2-azahexane hydrochloride in 2 ml of DMF are then added thereto and the mixture is stirred at room temperature overnight to complete the reaction. The reaction mixture is poured into 40 ml of water and extracted 3× with methylene chloride. The organic phases are filtered through cotton wadding, concentrated by evaporation and chromatographed (SiO$_2$; methylene chloride/methanol 25:1): TLC: R$_f$=0.48 (methylene chloride/methanol 19:1); HPLC$_{20\text{-}100(12')}$: t$_{Ret}$=11.8; FAB MS (M+H)$^+$=752.

The starting material is prepared as follows:

34a) N-1-(tert-Butyloxycarbonyl)-N-2-[N-methoxycarbonyl-(L)-tert-leucyl]-hydrazine With the exclusion of air, 10.0 g (52.8 mmol) of N-methoxycarbonyl-(L)-tert-leucine, 11.1 g (58 mmol) of EDC and 7.85 g (58 mmol) of HOBT are placed in 130 ml of ethyl acetate, and 7.0 ml (63 mmol) of NMM are added. After 30 min, 7.69 g (58 mmol) of tert-butyl carbazate are added and the mixture is then stirred at room temperature for 16 hours. The reaction mixture is diluted with 300 ml of ethyl acetate and washed with sat. NaHCO$_3$ solution, water and brine. The aqueous phases are back-extracted 2× with ethyl acetate. The organic phases are dried (Na$_2$SO$_4$) and concentrated by evaporation to form the title compound: $^1$H-NMR (CD$_3$OD) d 3.98 (s, 1H), 3.66 (s, 3H), 1.47 and 1.03 (2s, 2× 9H).

34b) [N-Methoxycarbonyl-(L)-tert-leucyl]-hydrazine 52.8 mmol of N-1-(tert-butyloxycarbonyl)-N-2-[N-methoxycarbonyl-(L)-tert-leucyl]-hydrazine are dissolved in 100 ml of 4N HCl/dioxane and stirred at room temperature for 18 hours. The suspension is concentrated by evaporation; the residue is taken up in sat. NaHCO$_3$ solution and extracted 4× with large amounts of methylene chloride. Filtration of the organic phases through cotton wadding and concentration by evaporation yield the title compound: $^1$H-NMR (CD$_3$OD) d 3.89 (s, 1H), 3.66 (s, 3H), 0.99 (s, 9H).

34c) N-1-[N-Methoxycarbonyl-(L)-tert-leucyl]-N-2-[4-(tetrazol-5-yl)-phenyl-methylidene]-hydrazone A solution of 3.0 g (14.8 mmol) of [N-methoxycarbonyl-(L)-tert-leucyl]-hydrazine and 2.57 g (14.8 mmol) of 4-(tetrazol-5-yl)-benzaldehyde (Example 25a) in 30 ml of isoPrOH is heated at boiling for 18 hours. The mixture is cooled; 100 ml of water are added and the precipitated title compound is filtered off: $^1$H-NMR (CD$_3$OD) d 8.23 (s, 1H), 8.15–7.9 (m, 4H), 4.08 (s, 1H), 3.67 (s, 3H), 1.06 (s, 9H).

34d) N-1-[N-Methoxycarbonyl-(L)-tert-leucyl]-N-2-[4-(2-tert-butyl-2H-tetrazol-5-yl)-phenyl-methylidene]-hydrazone In an autoclave, 3.0 g (8.3 mmol) of N-1-[N-methoxycarbonyl-(L)-tert-leucyl]-N-2-[4-(tetrazol-5-yl)-phenyl-methylidene]-hydrazone, 1.2 g of iso-butene and 54 μl of methanesulfonic acid in 25 ml of toluene are heated at 110° C. for 1 hour. The reaction mixture is diluted with ethyl acetate and washed with sat. NaHCO$_3$ solution and brine. The aqueous phases are back-extracted 2× with ethyl acetate; the organic phases are dried (Na$_2$SO$_4$) and concentrated by evaporation. Column chromatography (SiO$_2$; hexane/ethyl acetate 1:1) yields the title compound: TLC: R$_f$=0.22 (hexane/ethyl acetate 1:1); HPLC$_{20\text{-}100(12')}$: t$_{Ret}$=11.1; FAB MS (M+H)$^+$=416.

34e) N-1-[N-Methoxycarbonyl-(L)-tert-leucyl]-N-2-[4-(2-tert-butyl-2H-tetrazol-5yl)-benzyl]-hydrazine Under a nitrogen atmosphere, 2.00 g (4.81 mmol) of N-1-[N-methoxycarbonyl-(L)-tert-leucyl]-N-2-[4-(2tert-butyl-2H-tetrazol-5-yl)-phenyl-methylidene]-hydrazone are dissolved in 9 ml of THF, and 317 mg (4.8 mmol; 95%) of NaCNBH$_3$ are added. A solution of 915 mg (4.8 mmol) of p-toluenesulfonic acid monohydrate in 9 ml of THF is added dropwise thereto. After 18 hours, ethyl acetate is added and the mixture is washed with sat. NaHCO$_3$ solution and brine. The aqueous phases are extracted with a further 2× with ethyl acetate. The organic phases are dried (Na$_2$SO$_4$) and concentrated by evaporation. The residue is taken up in 20 ml of THF and 20 ml of water; 6.18 g (20 mmol) of K$_2$B$_4$O$_7$.4H$_2$O are added and the mixture is stirred at room temperature overnight. The reaction mixture is diluted with ethyl acetate and washed with sat. NaHCO$_3$ solution and brine. The aqueous phases are extracted 2× with ethyl acetate; the organic phases are dried (Na$_2$SO$_4$) and concentrated by evaporation. Column chromatography (SiO$_2$; hexane/ethyl acetate 1:2) yields the title compound: TLC: R$_f$=0.28 (hexane/ethyl acetate 1:2); $^1$H-NMR (CD$_3$OD) d 8.07 and 7.53 (2d, J=8, each 2H), 4.03 (s, 2H); 3.84 (s, 1H); 3.64 (s, 3H); 1.81 and 0.92 (2s, each 9H).

34f) 1-[4-(2tert-Butyl-2H-tetrazol-5-yl)-phenyl]-4(S)-hydroxy-5(S)-N-(tert-butyloxycarbonyl)amino-2-N-[N-methoxycarbonyl-(L)-tert-leucyl]amino-6-phenyl-2-azahexane 737 mg (2.80 mmol) of (2R)-[(1'S)-Boc-amino-2'-phenylethyl]oxirane and 1.17 g (2.80 mmol) of N-1-[N-methoxycarbonyl-(L)-tert-leucyl]-N-2-[4-(2-tert-butyl-2H-tetrazol-5-yl)-benzyl]-hydrazine are heated in 15 ml of iso-PrOH at 90° C. for 16 hours. On the addition of 100 ml of water the product crystallises and can be filtered off. Recrystallisation by the addition of DIPE/hexane to a concentrated solution in methylene chloride at 0° C. yields the title compound: TLC: $R_f$=0.34 (CH$_2$Cl$_2$/MeOH 30:1); HPLC$_{20\text{-}100(12')}$: $t_{Ret}$=12.5.

34g) 1-[4-(2-tert-Butyl-2H-tetrazol-5-yl)-phenyl]-4(S)-hydroxy-5(S)-amino-2-N-[N-methoxycarbonyl-(L)-tert-leucyl]amino-6-phenyl-2-azahexane hydrochloride Under a nitrogen atmosphere, 200 mg (0.293 mmol) of 1-[4-(2-tert-butyl-2H-tetrazol-5-yl)-phenyl]-4(S)-hydroxy-5(S)-N-(tert-butyloxycarbonyl)amino-2-N-[N-methoxycarbonyl-(L)-tert-leucyl]amino-6-phenyl-2-azahexane are dissolved in 2.3 ml of THF; 1.6 ml of aqueous 2N HCl are added and the mixture is stirred at 50° C. for 8 hours. The reaction solution is concentrated by evaporation; the residue is taken up several times in ethanol and concentrated by evaporation again (→title compound): TLC: $R_f$=0.08 (CH$_2$Cl$_2$/MeOH 30:1); HPLC$_{20\text{-}100(12')}$: $t_{Ret}$=9.9; $^1$H-NMR (CD$_3$OD) d 8.03 and 7.50 (2d, J=8, each 2H), 7.32 (m, 5H), 4.18 and 3.91 (2d, J=4, 2H), 3.80 (m, 1H), 3.68 (s, 1H), 3.58 (s, 3H), 3.57 (m, 1H), 3.3–2.9 (m, 4H), 1.81 and 0.75 (2s, each 9H).

Example 35

1-[4-(2-tert-Butyl-2H-tetrazol-5-yl)-phenyl]-4(S)-hydroxy-2N-(N-methoxycarbonyl-(L)-tert-leucyl)amino-5(S)-N-(N-methoxycarbonyl-(L)-valyl)amino-6-phenyl-2-azahexane Under a nitrogen atmosphere, 54 mg (0.308 mmol) of N-methoxycarbonyl-(L)-valine and 92 mg (0.308 mmol) of TPTU in 1 ml of DMF and 101 µl (0.91 mmol) of NMM are stirred at room temperature for 10 min. 190 mg (0.308 mmol) of 1-[4-(2-tert-butyl-2H-tetrazol-5-yl)-phenyl]-4(S)-hydroxy-5(S)-amino-2-N-[N-methoxycarbonyl-(L)-tert-leucyl]amino-6-phenyl-2-azahexane hydrochloride (Example 34g) in 2 ml of DMF are added thereto and the mixture is stirred at room temperature overnight to complete the reaction. The reaction mixture is diluted with methylene chloride and washed with brine. The aqueous phases are extracted 2× with methylene chloride; the organic phases are filtered through cotton wadding, concentrated by evaporation and chromatographed (SiO$_2$; methylene chloride/methanol 30:1): TLC: $R_f$=0.21 (methylene chloride/methanol 19:1); FAB MS (M+H)$^+$=738.

Example 36

1-[4-(2-Methyl-2H-tetrazol-5-yl)-phenyl]-4(S)-hydroxy-2-N-(N-methoxycarbonyl-(L)-tert-leucyl)amino-5(S)-N-(N-methoxycarbonyl-(L)-valyl)amino-6-phenyl-2-azahexane The title compound may be prepared analogously to one of the Examples mentioned hereinabove and hereinbelow.

Example 37

1-[4-(Pyridin-2-yl)-phenyl]-4(S)-hydroxy-5(S)-2,5-bis[N-(N-methoxycarbonyl-(L)-valyl)amino]-6-phenyl-2-azahexane With the exclusion of moisture, 455 mg (2.6 mmol) of N-methoxycarbonyl-(L)-valine, 940 mg (4.9 mmol) of EDC and 405 mg (3 mmol) of HOBT are placed in 10 ml of DMF and heated at 40° C. 1.1 ml (7.9 mmol) of TEA are added and the mixture is stirred for a further 15 min. 500 mg (0.98 mmol) of 1-[4-(pyridin-2-yl)-phenyl]-4(S)-hydroxy-5(S)-2,5-diamino-6-phenyl-2-azahexane hydrochloride are added thereto and the mixture is stirred at room temperature overnight. The reaction mixture is extensively concentrated by evaporation under a high vacuum; the residue is dissolved in methylene chloride and washed in succession with sodium carbonate solution (1×), phosphate buffer pH=7 (2×) and brine. After removal of the solvent, the residue is chromatographed on silica gel (eluant: methylene chloride/methanol 15:1). The product-containing fractions are concentrated and the title compound is precipitated with DIPE.

The product can be lyophilised from dioxane. HPLC$_{20\text{-}100}$: $t_{Ret}$=10.06; FAB MS (M+H)$^+$=677. 1H-NMR (CD$_3$OD; 200 MHz) i.a.: 8.58/m (1H); 7.78 and 7.50/each d, J=5 (2×2H); 8.0–7.73/m (2H); 7.33/m (1H); 7.30–7.05/m (5H); 3.62 and 3.60/each s (2×3H); 1.85 and 1.68/each m (2×1H); 0.76/'t', J=4 (6H); 0.65 and 0.58/each d, J=4 (2×3H).

The starting material is prepared as follows:

37a) 4-Bromobenzaldehyde dimethyl acetal 21.1 g (114 mmol) of 4-bromobenzaldehyde and 20 ml (182 mmol) of trimethyl orthoformate (both Fluka, Buchs, Switzerland) are dissolved in 35 ml of methanol, and 0.65 g (3.4 mmol) of p-toluenesulfonic acid monohydrate is added at room temperature (exothermic reaction). The reaction mixture is stirred at room temperature under nitrogen for 20 hours. The acid is then neutralised with 0.62 ml of 30% sodium methanolate solution in methanol (3.4 mmol); the reaction mixture is concentrated using a rotary evaporator and the residue is distilled. The title compound is obtained in the form of a colourless liquid. TLC: $R_f$=0.58 (hexane/ethyl acetate 2:1). B.p.: 90–92° C. (4 mbar). 1H-NMR (CDCl$_3$; 200 MHz): 7.50 and 7.32/each d, J=9 (2×2H); 5.36/s (1H); 3.31/s (6H).

37b) 4-(Pyridin-2-yl)-benzaldehyde 6.93 g (29.9 mmol) of 4-bromobenzaldehyde dimethyl acetal in 40 ml of THF are added dropwise to a warm (from 40° C. to 50° C.) suspension of 0.8 g (31.6 mmol) of magnesium turnings and a small amount of iodine in 10 ml of THF. The reaction mixture is heated to 65° C. and stirred at that temperature for about 30 min. The mixture is allowed to cool to room temperature and the Grignard reagent is added dropwise to a solution of 4.46 g (28.2 mmol) of 2-bromopyridine (Fluka, Buchs, Switzerland) and 0.4 g (0.74 mmol) of DPPP (Fluka, Buchs, Switzerland) in 100 ml of THF (slightly exothermic reaction). After the dropwise addition is complete, the reaction mixture is boiled under reflux for 4 hours and is then allowed to cool; 100 ml of water are added. The mixture is concentrated to about 50 ml using a rotary evaporator, diluted with ethyl acetate and extracted with 0.1N hydrochloric acid (3×). The combined HCl extracts are stirred at room temperature for 20 min, rendered basic with concentrated ammonia solution and extracted with methylene chloride. After removal of the solvent, the residue is chromatographed on silica gel (hexane/ethyl acetate 2:1). The product-containing fractions are concentrated, with the desired title compound crystallising out spontaneously. TLC: $R_f$=0.22 (hexane/ethyl acetate 2:1). HPLC$_{20\text{-}100}$: $t_{Ret}$=6.08. 1H-NMR (CDCl$_3$; 200 MHz): 8.73/d, J=5 (2H); 8.16 and 7.97/each d (2×2H); 7.80/d, J=4 (2H); 7.3/m (1H).

37c) N-1-(tert-Butoxycarbonyl)-N-2-{4-[(pyridin-2-yl)-phenyl]-methylidene}-hydrazone A solution of 2 g (1.05 mmol) of 4-(pyridin-2-yl)-benzaldehyde and 1.37 g (1 mmol) of tert-butyl carbazate (Fluka, Buchs, Switzerland) in 30 ml of ethanol is stirred at 80° C. for 5 hours (after 4 hours, a further 0.05 equivalent of tert-butyl carbazate is added). The reaction mixture is allowed to cool and diluted with water, with the desired title compound crystallising out. TLC: $R_f$=0.51 (methylene chloride/methanol 15:1). HPLC$_{20\text{-}100}$: $t_{Ret}$=8.92. 1H-NMR (CDCl$_3$; 200 MHz); 8.68/m (1 H); 8.21/s (1 H); 7.98/d, J=9 (2 H, portion A or aromatic AB system); 7.85/s (1 H); 7.8-7.6/m (4 H); 7.22/m (1 H); 1.53/s (9 H).

37d) N-1-(tert-Butoxycarbonyl)-N-2-[4-(pyridin-2-yl)-benzyl]-hydrazine 2 g (6.7 mmol) of N-1-(tert-butoxycarbonyl)-N-2-{4-[(pyridin-2-yl)phenyl]-methylidene}-hydrazone and 0.2 g of 5% of Pd/C in 30 ml of methanol are hydrogenated under normal pressure at room temperature for 8 hours. The catalyst is filtered off and washed with methanol; the solvent is removed. The title compound is obtained in the form of a colourless, viscous oil, which solidifies on drying under a high vacuum. TLC: $R_f$=0.46 (methylene chloride/methanol 15:1). HPLC$_{20-100}$: $t_{Ret}$=6.71. 1H-NMR (CDCl$_3$; 200 MHz) i.a.: 8.69/m (1 H); 7.96 and 7.45/each d, J=2 (2×2 H); 7.8-7.65/m (2 H); 7.22/m (1 H); 4.06/s (2 H); 1.47/s (9 H).

37e) 1-[4-(Pyridin-2-yl)-phenyl]-4(S)-hydroxy-5(S)-2,5-bis[(tert-butoxycarbonyl)amino]-6-phenyl-2-azahexane A solution of 1.06 g (4 mmol) of (2R)-[(1'S)-Boc-amino-2'-phenylethyl]oxirane and 1.2 g (4 mmol) of N-1-(tert-butoxycarbonyl)-N-2-[4-(pyridin-2-yl)-benzyl]-hydrazine in 20 ml of iso-PrOH is stirred at 80° C. for 16 hours. After cooling, the reaction solution is concentrated using a rotary evaporator, with the title compound precipitating out as a colourless precipitate. Further product can be precipitated out by adding water to the mother liquor. TLC: $R_f$=0.53 (methylene chloride/methanol 15:1). HPLC$_{20-100}$: $t_{Ret}$=13.15. 1H-NMR (CD$_3$OD; 200 MHz) i.a.: 8.57/s (1 H); 7.85 and 7.48/each d, J=9(2×2 H); 8.0-7.7/m (2 H); 7.33/m (1 H); 7.3-7.0/m (6 H); 3.91/s (2 H); 3.82-3.55/m (2 H); 3.05-2.45/m (4 H ); 1.31/s (18 H).

37f) 1-[4-(Pyridin-2-yl)-phenyl]-4(S)-hydroxy-5(S)-2,5-diamino-6-phenyl-2-azahexane hydrochloride 10 ml of DMF are added to a mixture consisting of 1.43 g (2.54 mmol) of 1-[4-(pyridin-2-yl)-phenyl]-4(S)-hydroxy-5(S)-2,5-bis[(tert-butoxycarbonyl)amino]-6-phenyl-2-azahexane in 30 ml of 4 N hydrogen chloride in dioxane (Aldrich) (exothermic reaction) and the mixture is stirred at room temperature for 2 hours. The solvent is then removed; toluene is added to the residue three times and the mixture is concentrated by evaporation. The residue is dissolved in hot methanol and the title compound is precipitated in the form of a resinous precipitate with DIPE/hexane. On drying under a high vacuum, a voluminous foam is obtained. HPLC$_{5-60}$: $t_{Ret}$=9.87. 1H-NMR (CD$_3$OD; 200 MHz) i.a.: 8.78/d, J=5 (1 H); 8.72/dxt, J=2.5 and 7.5 (1 H); 8.35/d, J=7.5 (1 H); 8.1/dxd, J=each 7.5 (1 H); 8.02 and 7.72/each d, J=9 (2×2 H); 7.45-7.15/m (5 H); 4.27 and 4.15/each d, J=12.5 (2×2 H).

Example 38

1-[4-(Pyridin-2-yl)-phenyl]-4(S)-hydroxy-5(S)-2,5-bis[N-(N-ethoxycarbonyl-(L)-valyl)amino]-6-phenyl-2-azahexane Analogously to Example 37, after working up the title compound is obtained from 300 mg (0.59 mmol) of 1-[4-(pyridin-2-yl)-phenyl]-4(S)-hydroxy-5(S)-2,5-diamino-6-phenyl-2-aza-hexane hydrochloride (Example 37f), 446 mg (2.36 mmol) of N-ethoxycarbonyl-(L)-valine, 679 mg (3.54 mmol) of EDC, 398 mg (2.95 mmol) of HOBT and 0.82 ml (5.9 mmol) of TEA in 10 ml of DMF. TLC: $R_f$=0.19 (methylene chloride/methanol 15:1). HPLC$_{20-100}$: $t_{Ret}$=11.68. FAB MS (M+H)$^{30}$ =705.

Example 39

1-[4-(Pyridin-3-yl)-phenyl]-4(S)-hydroxy-5(S)-2,5-bis[N-(N-methoxycarbonyl-(L)-valyl)amino]-6-phenyl-2-azahexane Analogously to Example 37, the title compound is obtained from 550 mg (1.52 mmol) of 1-[4-(pyridin-3-yl)-phenyl]-4(S)-hydroxy-5(S)-2,5-diamino-6-phenyl-2-azahexane, 691 mg (3.94 mmol) of N-methoxycarbonyl-(L)-valine, 1.45 g (7.59 mmol) of EDC, 641 mg (4.55 mmol) of HOBT and 1.06 ml (7.59 mmol) of TEA in 10 ml of DMF. (Contrary to the description in Example 37, the organic phase is washed with sat. sodium hydrogen carbonate solution, 10% citric acid and brine.) TLC: $R_f$=0.4 (methylene chloride/methanol 15:1). HPLC$_{20-100}$: $t_{Ret}$=9.91; FAB MS (M+H)$^+$=677.

The starting material is prepared as follows:

39a) 4-(Pyridin-3-yl)-benzaldehyde

Analogously to Example 37b, the title compound is obtained from 6.39 g (29.9 mmol) of 4-bromobenzaldehyde dimethyl acetal (prepared in accordance with Example 37a), 0.8 g (31.6 mmol) of magnesium turnings, 2.77 ml (28.2 mmol) of 3-bromopyridine (Fluke, Buchs, Switzerland) and 0.4 g (0.74 mmol) of DPPP in 150 ml of THF. HPLC$_{20-100}$: $t_{Ret}$=5.50. 1H NMR (CD$_3$OD; 200 MHz); 10.04/s (1 H); 8.87/d, J=2.5 (1 H); 8.58/dxd, J=about 1.5 and 5 (1 H); 8.17/m i.a. J=7.5 (1 H); 8.05 and 7.88/each d, J=9 (2×2 H); 7.56/dxd, J=7.5 and 5 (1 H).

39b) N-1-(tert-Butoxycarbonyl)-N-2-{4-[(pyridin-3-yl)-phenyl]-methylidene}-hydrazone Analogously to Example 37c, the title compound is obtained from 4.11 g (22.4 mmol) of 4-(pyridin-3-yl)-benzaldehyde and 2.82 g (21.3 mmol) of tert-butyl carbazate (Fluke, Buchs, Switzerland) in 60 ml of ethanol. HPLC$_{20-100}$: $t_{Ret}$=8.88. 1H-NMR (CD$_3$OD; 200 MHz): 8.83/d, J=2.5 (1 H); 8.53/d, J=5 (1 H); 8.14/m i.a. J=7.5 (1 H); 7.97/s (1 H); 7.85 and 7.71/each d, J=9 (2×2 H); 7.53/dxd, J=7.5 and 5 (1 H).

39c) N-1-(tert-Butoxycarbonyl)-N-2-[4-(pyridin-3-yl)-benzyl]-hydrazine

Analogously to Example 37d, the title compound is obtained from 5.03 g (16.9 mmol) of N-1-(tert-butoxycarbonyl)-N-2-{4-[(pyridin-3-yl)-phenyl]-methylidene}-hydrazone and 0.5 g of 5% Pd/C in 120 ml of methanol, the title compound being processed further in unpurified form. HPLC$_{20-100}$: $t_{Ret}$=6.36. 1H-NMR (CD$_3$OD; 200 MHz) i.a.: 7.63 and 7.51/each d, J=9 (2×2 H); 3.97/s (2 H); 1.43/s (9 H).

39d) 1-[4-(Pyridin-3-yl)-phenyl]-4(S)-hydroxy-5(S)-2,5-bis[(tert-butoxycarbonyl)amino]-6-phenyl-2-azahexane Analogously to Example 37e, the title compound is obtained from 3.82 g (12.8 mmol) of N-1-(tert-butoxycarbonyl)-N-2-[4-(pyridin-3-yl)-benzyl]-hydrazine and 3.36 g (12.8 mmol) of (2R)-[(1'S)-Boc-amino-2'-phenylethyl]oxirane after 14 hours at 80° C. Purification is carried out by chromatography on silica gel (hexane/ethyl acetate 1:2). TLC: $R_f$=0.27 (hexane/ethyl acetate 1:2). HPLC$_{20-100}$: $t_{Ret}$=13.0. 1H-NMR (CD$_3$OD; 200 MHz) i.a.: 7.62 and 7.52/each d, J=9 (2×2 H); 7.4-7.0/m (5 H); 3.93/s (2 H); 1.33 and 1.31/each s (2×9 H).

39e) 1-[4-(Pyridin-3-yl)-phenyl]-4(S)-hydroxy-5(S)-2,5-diamino-6-phenyl-2-azahexane 1 g (1.88 mmol) of 1-[4-(pyridin-3-yl)-phenyl]-4(S)-hydroxy-5(S)-2,5-bis[(tert-butoxycarbonyl)amino]-6-phenyl-2-azahexane is dissolved in 10 ml of formic acid and the solution is stirred at room temperature for 5 hours. The reaction mixture is concentrated by evaporation, the residue dissolved in methylene chloride and the organic phase washed with sat. sodium hydrogen carbonate solution and brine. After removal of the solvent, the title compound is obtained in the form of a brown oil, which is processed further without purification.

Example 40

1-[4-(Pyrazin-2-yl)-phenyl]-4(S)-hydroxy-5(S)-2,5-bis[N-(N-methoxycarbonyl-(L)-valyl)amino]-6-phenyl-2-azahexane Analogously to Example 37, the title compound is obtained from 473 mg (0.75 mmol) of 1-[4-(pyrazin-2-yl)- phenyl]-4(S)-hydroxy-2-amino-5(S)-N-(N-methoxycarbonyl-(L)-valyl)amino-6-phenyl-2-azahexane hydrochloride, 263 mg (1.5 mmol) of N-methoxycarbonyl-(L)-valine, 575 mg (3 mmol) of EDC (Fluka, Buchs, Switzerland), 405 mg (3 mmol) of HOBT (Fluka) and 1.7 ml (12 mmol) of TEA in 10 ml of DMF. Working up is performed analogously to Example 40f, using ethyl acetate instead of methylene chloride. The compound can be lyophilised from dioxane. TLC: $R_f$=0.28 (ethyl acetate). HPLC$_{20-100}$: $t_{Ret}$=13.11; FAB MS (M+H)$^+$=678.

The starting material is prepared as follows:

40a) 4-(Pyrazin-2-yl)-benzaldehyde

[see EP 0 344 577]

50 ml of THF are poured over 2.72 g (112 mmol) of magnesium turnings, which have been de-greased with hexane and activated with a small amount of iodine, and the mixture is heated at 50° C. A solution of 4-bromobenzaldehyde dimethyl acetal (prepared in accordance with Example 37a) in 200 ml of THF is added dropwise to the mixture within a period of about 30 min. Initially, the reaction is exothermic; towards the end of the dropwise addition the reaction mixture is heated to about 60° C. After stirring at 60° C. for a further 30 min, the mixture is allowed to cool to room temperature and decanted off from the unreacted magnesium; the resulting solution containing the Grignard reagent is added dropwise at room temperature over a period of 20 min to a suspension of 11.45 g (100 mmol) of 2-chloropyrazine (Fluke, Buchs, Switzerland) and 1.6 g of DPPP (Aldrich, Buchs, Switzerland) in 500 ml of THF (slightly exothermic reaction). The mixture is then stirred at room temperature for 19 hours. Then 250 ml of water are added to the reaction mixture and the mixture is stirred for 10 min. The THF is removed in vacuo; 300 ml of ethyl acetate and 100 ml of 2 N hydrochloric acid are added to the emulsion that remains and the mixture is stirred for 5 min. After separation of the organic phase, that phase is stirred twice more with 100 ml, in each case, of 0.5 N hydrochloric acid for 5 min. The ethyl acetate phase is washed in succession with sat. sodium hydrogen carbonate solution, water and brine and is concentrated. The title compound is obtained in the form of light-brown crystals. Recrystallisation from methylene chloride/hexane is carried out. M.p.: 86–88° C. TLC: $R_f$=0.17 (hexane/ethyl acetate 2:1). HPLC$_{20-100}$: $t_{Ret}$=11.06. 1H-NMR (CDCl$_3$; 200 MHz): 10.12/s (1 H); 9.14/d, J≦1 (1 H); 8.70/d, J≦1 (1 H); 8.60/t, J≦1 (1 H); 8.22 and 8.03/each d, J=9 (2×2 H).

40b) N-1-(tert-Butoxycarbonyl)-N-2-{4-[(pyrazin-2-yl)-phenyl]-methylidene}-hydrazone Analogously to Example 37c, the title compound is obtained from 12.4 g (67.3 mmol) of 4-(pyrazin-2-yl)-benzaldehyde and 8.5 g (64 mmol) of tert-butyl carbazate (Fluke, Buchs, Switzerland) in 170 ml of ethanol after 5 hours at 80° C., with the title compound crystallising out spontaneously. M.p.: 190–198° C. TLC: $R_f$=0.47 (ethyl acetate). HPLC$_{20-100}$: $t_{Ret}$=13.41.

40c) N-1-(tert-Butoxycarbonyl)-N-2-[4-(pyrazin-2-yl)-benzyl]-hydrazine

Analogously to Example 37d, the title compound is obtained in the form of an oil from 0.6 g (2 mmol) of N-1-(tert-butoxycarbonyl)-N-2-{4-[(pyrazin-2-yl)-phenyl]-methylidene}-hydrazone and 0.15 g of 5% Pd/C in 15 ml of THF after hydrogenation for 13 hours at room temperature. The title compound crystallises out on trituration with ether. Recrystallisation from ethyl acetate/petroleum ether is carried out. M.p.: 110–111° C. HPLC$_{20-100}$: $t_{Ret}$=9.62.

1H-NMR (CD$_3$OD; 200 MHz): 9.09/s (1 H); 8.65/t, J≦1 (1 H); 8.51/t, J≦1 (1 H); 8.05 and 7.53/each d, J=5 (2×2 H); 4.00/s (2 H); 1.43/s (9 H).

40d) 1-[4-(Pyrazin-2-yl)-phenyl]-4(S)-hydroxy-2-(tert-butoxycarbonyl)amino-5(S)-(trifluoroacetyl)amino-6-phenyl-2-azahexane Analogously to Example 37e, the title compound is obtained in the form of beige crystals from 10.5 g (35 mmol) of N-1-(tert-butoxycarbonyl)-N-2-[4-(pyrazin-2-yl)-benzyl]-hydrazine and 11.7 g (45 mmol) of (2R)-[(1'S)-(trifluoroacetyl)amino-2'-phenylethyl]oxirane (EP 0 521 827, Example 16d) in 150 ml of isopropanol. M.p.: 194–196° C. TLC: $R_f$=0.38 (hexane/ethyl acetate 1:2). HPLC$_{20-100}$: $t_{Ret}$=16.27.

40e) 1-[4-(Pyrazin-2-yl)-phenyl]-4(S)-hydroxy-2-(tert-butoxycarbonyl)amino-5(S)-amino-6-phenyl-2-azahexane 11.75 g (21 mmol) of 1-[4-(pyrazin-2-yl)-phenyl]-4(S)-hydroxy-2-(tert-butoxycarbonyl)amino-5(S)-(trifluoroacetyl)amino-6-phenyl-2-azahexane are suspended in 500 ml of methanol and, at 60° C., 105 ml of a 1 M K$_2$CO$_3$ solution in water are added. The mixture is stirred at 75° C. for about 3 hours; the methanol is evaporated off and the residue is extracted with ethyl acetate. The organic phase is washed once each with water and brine and concentrated. The title compound is obtained in the form of orange-brown crystals, which can be recrystallised from ethyl acetate/petroleum ether. M.p.: 146–148° C. TLC: $R_f$=0.08 (methylene chloride/methanol 10:1). HPLC$_{20-100}$: $t_{Ret}$=11.23.

40f) 1-[4-(Pyrazin-2-yl)-phenyl]-4(S)-hydroxy-2-(tert-butoxycarbonyl)amino-5(S)-N-(N-methoxycarbonyl-(L)-valyl)amino-6-phenyl-2-azahexane Analogously to Example 37, the title compound is obtained from 3.2 g (7 mmol) of 1-[4-(pyrazin-2-yl)-phenyl]-4(S)-hydroxy-2-(tert-butoxycarbonyl)amino-5(S)-amino-6-phenyl-2-azahexane, 2.54 g (14 mmol) of N-methoxycarbonyl-(L)-valine, 5.4 g (28 mmol) of EDC (Fluka, Buchs, Switzerland), 3.8 g (28 mmol) of HOBT (Fluka, Buchs, Switzerland) and 7.1 g (70 mmol) of TEA in 130 ml of DMF. The reaction mixture is worked up by removing the DMF, taking up the residue in methylene chloride and washing the organic phase in succession with water, sat. sodium hydrogen carbonate solution/water 1:1, 10% citric acid, water and brine. The compound crystallises out on concentration. M.p.: 218–220° C. TLC: $R_f$=0.29 (methylene chloride/methanol 10:1). HPLC$_{20-100}$: $t_{Ret}$=15.11.

40g) 1-[4-(Pyrazin-2-yl)-phenyl]-4(S)-hydroxy-2-amino-5(S)-N-(N-methoxycarbonyl-(L)-valyl)amino-6-phenyl-2-azahexane hydrochloride 3.4 g (5.5 mmol) of 1-[4-(pyrazin-2-yl)-phenyl]-4(S)-hydroxy-2-(tert-butoxycarbonyl)amino-5(S)-N-(N-methoxycarbonyl-(L)-valyl)amino-6-phenyl-2-azahexane in 100 ml of 4 N hydrogen chloride in dioxane (Aldrich) and 10 ml of methanol are stirred at room temperature for 2 hours. The solvents are removed; dioxane is added twice to the residue and evaporated off. The title compound is obtained in the form of a viscous oil, with the compound crystallising out on trituration with ether. M.p.: 194–198° C. TLC: $R_f$=0.35 (methylene chloride/methanol 10:1). HPLC$_{20-100}$: $t_{Ret}$=9.77.

Example 41

1-[4-(Pyrazin-2-yl)-phenyl]-4(S)-hydroxy-2-[N-(N-methoxycarbonyl-(L)-iso-leucyl)amino]-5(S)-[N-(N-methoxycarbonyl-(L)-valyl)amino]-6-phenyl-2-azahexane 142 mg (0.75 mmol) of N-methoxycarbonyl-(L)-iso-leucine and 223 mg (0.75 mmol) of TPTU in 3 ml of DMF are stirred at room temperature for 10 min and then a solution of 473 mg (0.75 mmol) of 1-[4-(pyrazin-2-yl)-phenyl]-4(S)-hydroxy-2-amino-5(S)-N-(N-methoxycarbonyl-(L)-valyl)amino-6-phenyl-2-azahexane hydrochloride (Example 40g) and 0.33 ml of NMM in 3 ml of DMF is added. The mixture is stirred at room temperature overnight. Working up is carried out by the slow, dropwise addition of the reaction mixture to 100 ml of water, stirring at room temperature for 20 min and isolation of the resulting precipitate by filtration. The precipitate is washed with water and taken up in methylene chloride; the organic phase is washed in succession with water, sat. sodium hydrogen carbonate solution/water 1:1, water and brine. After removal of the solvent, the residue is digested in ether, with the title compound being obtained in the form of a colourless powder. The compound can be lyophilised from dioxane. TLC: $R_f$=0.28 (ethyl acetate). $HPLC_{20-100}$: $t_{Ret}$=13.78. FAB MS(M+H)$^+$=692.

Example 42

1-[4-(Pyrazin-2-yl)-phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane Analogously to Example 41, after working up the title compound is obtained from 142 mg (0.75 mmol) of N-methoxycarbonyl-(L)-tert-leucine (Example 2e), 223 mg (0.75 mmol) of TPTU in 3 ml of DMF (solution A) and 435 mg (0.75 mmol) of 1-[4-(pyrazin-2-yl)-phenyl]-4(S)-hydroxy-2-amino-5(S)-N-(N-methoxycarbonyl-(L)-valyl)amino-6-phenyl-2-azahexane hydrochloride (Example 40g) and 0.33 ml of NMM in 3 ml of DMF (solution B), the title compound crystallising out spontaneously on evaporation of the solvent. The compound can be lyophilised from dioxane. TLC: $R_f$=0.46 (methylene chloride/methanol 10:1). $HPLC_{20-100}$: $t_{Ret}$=13.85. FAB MS(M+H)$^+$=692.

Example 43

1-[4-(Pyrazin-2-yl)-phenyl]-4(S)-hydroxy-5(S)-2,5-bis[N-(N-methoxycarbonyl-(L)-iso-leucyl)amino]-6-phenyl-2-azahexane Analogously to Example 41, after working up the title compound is obtained from 132 mg (0.7 mmol) of N-methoxycarbonyl-(L)-iso-leucine and 208 mg (0.7 mmol) of TPTU in 3 ml of DMF (solution A) and 400 mg (0.7 mmol) of 1-[4-(pyrazin-2-yl)-phenyl]-4(S)-hydroxy-2-amino-5(S)-N-(N-methoxycarbonyl-(L)-iso-leucyl)amino-6-phenyl-2-azahexane hydrochloride (Example 44b) and 0.31 ml (2.8 mmol) of NMM in 3 ml of DMF, the title compound being obtained in crystalline form by digestion with ether. M.p.: 211–217° C. TLC: $R_f$=0.41 (methylene chloride/methanol 10:1). $HPLC_{20-100}$: $t_{Ret}$=14.49. FAB MS(M+H)$^+$=706.

Example 44

1-[4(Pyrazin-2-yl)-phenyl]-4(S)-hydroxy-2-[N-(N-methoxycarbonyl-(L)-valyl)amino]-5(S)-[N-(N-methoxycarbonyl-(L)-tert-leucyl)amino]-6-phenyl-2-azahexane Analogously to Example 41, after working up the title compound is obtained from 175 mg (1 mmol) of N-methoxycarbonyl-(L)-valine, 297 mg (1 mmol) of TPTU (Fluka, Buchs, Switzerland) in 4 ml of DMF (solution A) and 571 mg (1 mmol) of 1-[-4-(pyrazin-2-yl)-phenyl]-4(S)-hydroxy-2-amino-5(S)-N-(N-methoxycarbonyl-(L)-iso-leucyl)amino-6-phenyl-2-azahexane hydrochloride and 0.44 ml (4 mmol) of NMM in 4 ml of DMF (solution B); the title compound can be obtained in crystalline form by digestion with ether. M.p.: 205–208° C. $HPLC_{20-100}$: $t_{Ret}$=13.87. FAB MS(M+H)$^+$=692.

The starting material is prepared as follows:

44a) 1-[-4-(Pyrazin-2-yl)-phenyl]-4(S)-hydroxy-2-(tert-butoxycarbonyl)amino-5(S)-N-(N-methoxycarbonyl-(L)-iso-leucyl)amino-6-phenyl-2-azahexane Analogously to Example 37, the title compound is obtained from 2.3 g (5 mmol) of 1-[4-(pyrazin-2-yl)-phenyl]-4(S)-hydroxy-2-(tert-butoxycarbonyl)amino-5(S)-amino-6-phenyl-2-azahexane (Example 40e), 1.9 g (10 mmol) of N-methoxycarbonyl-(L)-iso-leucine, 3.8 g (20 mmol) of EDC, 2.7 g (20 mmol) of HOBT and 5.1 g (50 mmol) of TEA in 90 ml of DMF. Working up is carried out as described in Example 40f. The compound can be recrystallised from ethyl acetate. TLC: $R_f$=0.58 (methylene chloride/methanol 10:1). $HPLC_{20-100}$: $t_{Ret}$=15.68. 1H-NMR (CD$_3$OD; 200 MHz) i.a.: 9.08/s (1 H); 8.65/bs (1 H); 8.51/t, J≦1 (1 H); 8.02 and 7.52/each d, J=5 (2×2 H); 7.3-7.1/m (5 H); 3.92/s (2 H); 3.62/s (3 H); 1.28/s (9 H); 0.8/t, J=5 (3 H); 0.73/d, J=4 (3 H).

44b) 1-[4-(Pyrazin-2-yl)-phenyl]-4(S)-hydroxy-2-amino-5(S)-N-(N-methoxycarbonyl-(L)-iso-leucyl)amino-6-phenyl-2-azahexane hydrochloride Analogously to Example 40g, the title compound is obtained from 2.1 g (3.3 mmol) of 1-[4-(pyrazin-2-yl)-phenyl]-4(S)-hydroxy-2-(tert-butoxycarbonyl)amino-5(S)-N-(N-methoxycarbonyl-(L)-iso-leucyl)amino-6-phenyl-2-azahexane in 60 ml of 4 N hydrogen chloride in dioxane and 10 ml of methanol, with the title compound being caused to crystallise with ether. M.p.: 200–201° C. $HPLC_{20-100}$: $t_{Ret}$=10.52.

Example 45

1-[4-(Thiophen-2-yl)-phenyl]-4(S)-hydroxy-5(S)-2,5-bis[N-(N-methoxycarbonyl-(L)-valyl)amino]-6-phenyl-2-azahexane Analogously to Example 37, the title compound is obtained from 500 mg (1.36 mmol) of 1-[4-(thiophen-2-yl)-phenyl]-4(S)-hydroxy-5(S)-2,5-diamino-6-phenyl-2-azahexane, 620 mg (3.54 mmol) of N-methoxycarbonyl-(L)-valine, 1.3 g (6.8 mmol) of EDC, 551 mg (4.08 mmol) of HOBT and 0.95 ml (6.8 mmol) of TEA in 10 ml of DMF, the title compound being lyophilised from dioxane. TLC: $R_f$=0.51 (methylene chloride/methanol 15:1). $HPLC_{20-100}$: $t_{Ret}$=15.30. FAB MS(M+H)$^+$=682.

The starting material is prepared as follows:

45a) 4-(Thiophen-2-yl)-benzaldehyde

[see Heterocycles 31, 1951 (1990)]

3.7 g (20 mmol) of 4-bromobenzaldehyde, 9.5 ml (120 mmol) of thiophene, 2.94 g (30 mmol) of potassium acetate and 1.16 g (1 mmol) of tetrakis(triphenylphosphine) palladium (Fluka, Buchs, Switzerland) in 50 ml of dimethylacetamide are placed in a pressure reactor and stirred at 150° C. under nitrogen for 16 hours. The reaction mixture is concentrated by evaporation; the residue is taken up in water and extracted three times with methylene chloride. After removal of the solvent, the residue is chromatographed on silica gel (hexane/ethyl acetate 4:1). The title compound is obtained in the form of a yellow solid. TLC: $R_f$=0.36

(hexane/ethyl acetate 4:1). HPLC$_{20-100}$: t$_{Ret}$=15.26. 1H-NMR (CD$_3$OD; 200 MHz): 9.98/s (1 H); 7.93 and 7.85/each d, J=9.5 (2×2 H); 7.60/d, J=2.5 (1 H); 7.52/d, J=5 (1 H); 7.17/dxd, J=2.5 and 5 (1 H).

45b) N-1-(tert-Butoxycarbonyl)-N-2-{4-[(thiophen-2-yl)-phenyl]-methylidene}-hydrazone Analogously to Example 37c, the title compound is obtained in the form of yellow crystals from 2.47 g (13.1 mmol) of 4-(thiophen-2-yl)-benzaldehyde and 1.65 g (12.49 mmol) of tert-butyl carbazate (Fluke, Buchs, Switzerland) in 30 ml of ethanol (4.5 hours at 90° C.). M.p.: 162–165° C. HPLC$_{20-100}$: t$_{Ret}$=16.08. 1H-NMR (CD$_3$OD; 200 MHz) i.a.: 7.91/s (1 H); 1.53/s (9 H).

45c) N-1-(tert-Butoxycarbonyl)-N-2-[4-(thiophen-2-yl)-benzyl]-hydrazine 3.35 g (11.1 mmol) of N-1-(tert-butoxycarbonyl)-N-2-{4-[(thiophen-2-yl)-phenyl]-methylidene}-hydrazone and 0.819 g (11.1 mmol) of sodium cyanoborohydride (Fluka, Buchs, Switzerland) are dissolved in 11 ml of THF (black solution) and added dropwise over a period of 5 hours to 2.11 g (11.1 mmol) of p-toluenesulfonic acid monohydrate dissolved in 11 ml of THF. The mixture is stirred overnight at room temperature and under nitrogen (pH=about from 3 to 4) and then diluted with ethyl acetate; the organic phase is washed in succession with brine, sat. sodium hydrogen carbonate solution and again brine. The organic phase is concentrated by evaporation and the residue is taken up in 13.3 ml of 1 N sodium hydroxide solution; 15 ml of methylene chloride are added and the mixture is boiled under reflux for 3 hours at a bath temperature of 60° C. After separation of the organic phase, that phase is concentrated to dryness by evaporation. The title compound is obtained in the form of a slightly yellowish oil. HPLC$_{20-100}$: t$_{Ret}$=12.36. 1H-NMR (CD$_3$OD; 200 MHz) i.a.: 3.91/s (2 H); 1.42/s (9 H).

45d) 1-[4-(Thiophen-2-yl)-phenyl]-4(S)-hydroxy-5(S)-2,5-bis[(tert-butoxycarbonyl)amino]-6-phenyl-2-azahexane Analogously to Example 37e, the title compound is obtained from 3.39 g (11.1 mmol) of N-1-(tert-butoxycarbonyl)-N-2-[4-(thiophen-2-yl)-benzyl]-hydrazine and 2.93 g (11.1 mmol) of (2R)-[(1'S)-Boc-amino-2'-phenylethyl]oxirane (J. Org. Chem. 50, 4615 (1985) in 50 ml of isopropanol, with the title compound crystallising out spontaneously on cooling of the reaction solution. M.p.: 165–168° C. HPLC$_{20-100}$: t$_{Ret}$=18.84. 1H-NMR (CD$_3$OD; 200 MHz) i.a.: 7.56/d, J=9 (2 H); 7.5-7.3/m (4 H); 7.3-7.1/m (5 H); 7.08/dxd, J=2 and 5 (1 H); 3.85/s (2 H); 1.33 and 1.32/each s (2×9 H).

45e) 1-[4-(Thiophen-2-yl)-phenyl]-4(S)-hydroxy-5(S)-2,5-diamino-6-phenyl-2-azahexane Analogously to Example 39e, the title compound is obtained in the form of a slightly yellowish oil from 3.16 g (5.57 mmol) of 1-[4-(thiophen-2-yl)-phenyl]-4(S)-hydroxy-5(S)-2,5-bis[(tert-butoxycarbonyl)amino]-6-phenyl-2-azahexane in 30 ml of formic acid after stirring at room temperature for 6 hours, that oil being processed further without purification. 1H-NMR (CD$_3$OD; 200 MHz) i.a.: 7.62/d, J=9 (2 H); 7.5-7.1/several m's, superimposed (9 H); 7.09/dxd, J=2 and 5 (1 H); 3.82/s (2 H).

Example 46

1-[4-(Pyridin-2-yl)-phenyl]-4(S)-hydroxy-5(S)-2,5-bis[N-(N-methoxycarbonyl-(L)-tert-leucyl)amino]-6-phenyl-2-azahexane Process A With the exclusion of moisture, 10.85 g of N-methoxycarbonyl-(L)-tert-leucine (Example 2e) and 17.1 g of TPTU are placed in 65 ml of DMF. 35.1 ml of Hünig base are added to the white suspension and the mixture is stirred at room temperature for 20 min. Then 13.2 g (26 mmol) of 1-[4-(pyridin-2-yl)-phenyl]-4(S)-hydroxy-5(S)-2,5-diamino-6-phenyl-2-aza-hexane hydrochloride (Example 37f) dissolved in 65 ml of DMF are added and the mixture is stirred for 24 hours to complete the reaction (after 20 hours, a further 5 ml of Hünig base are added). The reaction mixture is poured into 600 ml of water and the resulting precipitate is filtered off and washed with water. The filter residue is then dissolved in methylene chloride and washed 2× with sat. NaHCO$_3$ solution, water and brine. After drying over sodium sulfate and concentration, the resulting foam is digested with DIPE; the solid is filtered off and dried. The resulting crude product is dissolved again in methylene chloride, treated with active carbon and, after filtration, precipitated with ether. The resulting title compound is dried in a heated desiccator at 40° C. under a high vacuum: m.p.: 202–204° C.; TLC: R$_f$=0.38 (ethyl acetate); HPLC$_{20-100}$: t$_{Ret}$=11.81; FAB MS (M+H)$^+$=705. Further product can be obtained from the mother liquor after chromatography (SiO$_2$, hexane/ethyl acetate, then ethyl acetate) and after crystallisation from ether (m.p. 206–207° C.).

Process B

Analogously to Example 4, 1.32 g of 1-[4-(pyridin-2-yl)-phenyl]-4(S)-hydroxy-2-amino-5(S)-N-(N-methoxycarbonyl-(L)-tert-leucyl)amino-6-phenyl-2-azahexane in 5 ml of DMF are added to 0.42 g (2.2 mmol) of (N-methoxycarbonyl-(L)-tert-leucine, 0.654 g (2.2 mmol) of TPTU and 840 μl (5 mmol) of Hünig Base in 5 ml of DMF, and the mixture is stirred at room temperature for 22 hours and worked up analogously to Example 3 to yield the title compound.

The starting compounds are prepared as follows:

46a) 1-[4-(Pyridin-2-yl)-phenyl]-4(S)-hydroxy-2-Boc-amino-5(S)-N-(N-methoxycarbonyl-(L)-tert-leucyl)amino-6-phenyl-2-azahexane Analogously to Example 1, a solution of 3.93 g (8.5 mmol) of 1-[4-(pyridin-2-yl)-phenyl]-4(S)-hydroxy-2-(N-Boc-amino)-5(S)-amino-6-phenyl-2-azahexane hydrochloride (Example 47b) in 50 ml of DMF is added dropwise to a mixture of 2.58 g (13.6 mmol) of N-methoxycarbonyl-(L)-tert-leucine, 4.88 g (25.5 mmol) of EDC and 2.3 g (17 mmol) of HOBT in 50 ml of DMF. After working up, the crude product is digested in methylene chloride/DIPE, filtered off and dried to yield the title compound. TLC: R$_f$=0.5 (ethyl acetate); HPLC$_{20-100}$: t$_{Ret}$=12.32; FAB MS (M+H)$^+$=634.

46b) 1-[4-(Pyridin-2-yl)-phenyl]-4(S)-hydroxy-2-amino-5(S)-N-(N-methoxycarbonyl-(L)-tert-leucyl)amino-6-phenyl-2-azahexane hydrochloride Analogously to Example 37f), 130 ml of 4 M HCl in dioxane are added to 4.4 g (6.94 mmol) of 1-[4-(pyridin-2-yl)-phenyl]-4(S)-hydroxy-2-N-Boc-amino-5(S)-N-(N-methoxycarbonyl-(L)-tert-leucyl)amino-6-phenyl-2-azahexane and the mixture is diluted with 7 ml of DMF. After 2.75 hours, the mixture is worked up. The title compound is obtained: TLC: R$_f$=0.44 (methylene chloride/methanol: 9/1); HPLC$_{20-100}$: t$_{Ret}$=8.47; FAB MS (M+H)$^+$=534.

An alternative procedure for the preparation of the title compound from Example 46 is as follows:

Example 46*

1-[4-(Pyridin-2-yl)-phenyl]-4(S)-hydroxy-5(S)-2,5-bis[N-(N-methoxycarbonyl-(L)-tert-leucyl)amino]-6-phenyl-2-azahexane With the exclusion of moisture, 567 g (3.0 mol) of N-methoxycarbonyl-(L)-tert-leucine (Example 2e) and 891 g (3.0 mol) of TPTU are placed in 3 liters of methylene chloride; with ice-cooling, 775 g (6 mol) of Hünig base are added dropwise and the mixture is stirred for 20 min. A suspension of 432 g (1.0 mol) of 1-[4-(pyridin-2-yl)-phenyl]-4(S)-hydroxy-5(S)-2,5-diamino-6-phenyl-2-azahexane trihydrochloride in 3 liters of methylene chloride is then added to the solution and the mixture is stirred at room temperature overnight to complete the reaction. The reaction mixture is washed with 10 liters of water, 10 liters of sat. NaHCO$_3$ solution and 5 liters of brine. The aqueous phases are extracted a further 2× with 5 liters of methylene chloride; the organic phases are dried (Na$_2$SO$_4$) and concentrated by evaporation. The residue is dissolved in 6 liters of ethyl acetate and filtered through 500 g of silica gel; the column is rinsed with 6 liters of ethyl acetate and the product-containing fractions are concentrated by evaporation. Stirring in boiling DIPE/ethanol 49:1 (9 liters; 1 hour), cooling and filtration yield the title compound, which can be further purified by recrystallisation from ethanol/water (m.p. 207–209° C.).

The starting compounds are prepared as follows:

*a) 4-(Pyridin-2-yl)-benzaldehyde 11 g of iodine, followed by 200 g of 4-bromobenzaldehyde dimethyl acetal (Example 37a), are added to 317 g (13.0 mol) of magnesium in 3.5 liters of THF (nitrogen atmosphere). Once the reaction has started (heating if necessary), 2540 g (in total 2740 g; 11.8 mol) of 4-bromobenzaldehyde dimethyl acetal in 3.5 liters of toluene are added dropwise (from 25° to 30° C., 1 hours) and the mixture is then stirred at room temperature for 1 hour. The Grignard reagent is then transferred to the dropping funnel of a second apparatus containing 1750 g (11.0 mol) of 2-bromopyridine (Fluka, Buchs, Switzerland) in 3.3 liters of THF, 38 g (70 mmol) of DPPP and 330 ml of diisobutylaluminium hydride (20% in hexane). At from 15° to 20° C., the Grignard reagent is added dropwise (45 min). After being stirred at room temperature for 90 min, the reaction mixture is poured into 10 kg of ice, 1.5 liters of concentrated hydrochloric acid and 1.5 kg of citric acid. 1 kg of Hyflo Super Cel is added, and the mixture is stirred for 1 hour and then filtered; the residue is washed with 2 liters of water, 2×2 liters of toluene and, finally, 2×2 liters of 1 N HCl solution. The first filtrate and the washing water are combined; the aqueous phase is separated off and extracted 2× with the two toluene filtrates. The resulting organic phases are washed with the two hydrochloric-acid-containing filtrates. The aqueous phases are combined; 6 liters of toluene are added and the mixture is adjusted to a pH of from 8 to 9 with 4.6 liters of sodium hydroxide solution (30% in water). The mixture is filtered through Hyflo (filtration aid based on kieselguhr, Fluka, Buchs, Switzerland); the aqueous phase is separated off and extracted 2× with 2 liters of toluene. The organic phases are washed 2× with water, dried (Na$_2$SO$_4$) and treated with active carbon. Addition of 0.5 kg of silica gel, stirring, filtration and concentration by evaporation yield the title compound (physical data as Example 37b).

*b) N-1-(tert-Butoxycarbonyl)-N-2-{4-[(pyridin-2-yl)-phenyl]-methylidene}-hydrazone A solution of 1770 g (9.67 mol) of 4-(pyridin-2-yl)-benzaldehyde and 1220 g (9.2 mol) of tert-butyl carbazate (Fluka, Buchs, Switzerland) in 12.5 liters of ethanol is heated at boiling for 4 hours. The mixture is cooled to 40° C. and 6 kg of ice are added; the mixture is filtered off and the title compound is washed with 6 liters of water, that compound then being obtained in pure form (physical data as in Example 37c).

*c) N-1-(tert-Butoxycarbonyl)-N-2-[4-(pyridin-2-yl)-benzyl]-hydrazine

A suspension of 1655 g (5.57 mol) of N-1-(tert-butoxycarbonyl)-N-2-{4-[(pyridin-2-yl)-phenyl]-methylidene}-hydrazone in 12 liters of methanol is hydrogenated in the presence of 166 g of 10% Pd/C under normal pressure at room temperature. The catalyst is filtered off and washed thoroughly with methanol; the solvent is removed. Crystallisation from hexane yields the title compound: m.p.: 74–77° C.

*d) 1-[4-(Pyridin-2-yl)-phenyl]-4(S)-hydroxy-5(S)-2,5-bis[(tert-butoxycarbonyl)amino]-6-phenyl-2-azahexane A solution of 1185 g (4.5 mol) of (2R)-[(1'S)-(tert-butoxycarbonyl)-amino-2'-phenylethyl]-oxirane and 1230 g (4.1 mol) of N-1-(tert-butoxycarbonyl)-N-2-[4-(pyridin-2-yl)-benzyl]-hydrazine in 14 liters of iso-propanol are heated at boiling for 16 hours. After cooling, 15 kg of ice and 10 liters of water are added; the mixture is stirred for 2 hours; the crystals are filtered off and washed with 6 liters of water. Stirring twice in 5 liters of ether in each case, filtration, washing with 2 liters of ether and, finally, 2 liters of ether/tert-butyl methyl ether 1:1 yield the title compound: m.p.: 183–188° C.

*e) 1-[4-(Pyridin-2-yl)-phenyl]-4(S)-hydroxy-5(S)-2,5-diamino-6-phenyl-2-azahexane trihydrochloride A solution of 1465 g (2.6 mol) of 1-[4-(pyridin-2-yl)-phenyl]-4(S)-hydroxy-5(S)-2,5-bis[(tert-butoxycarbonyl)amino]-6-phenyl-2-azahexane in 12 liters of THF and 4 liters of hydrochloric acid (4 N in water) is stirred at 50° C. for 4 hours. The aqueous phase is separated from the resulting two-phase mixture and concentrated by evaporation in vacuo. The residue is diluted with 4 liters of ethanol, concentrated by evaporation, diluted with 4 liters of ethanol/toluene 1:1, concentrated by evaporation, diluted with 4 liters of ethanol and concentrated by evaporation again. Stirring in 9 liters of DIPE and filtration yield the title compound (physical data as Example 37f).

*e(i): Alternatively, 1-(4-(pyridin-2-yl)-phenyl)-4(S)-hydroxy-5(S)-2,5-di[(tert-butoxycarbonyl)amino]-6-phenyl-2-azahexane as prepared as follows Under a nitrogen atmosphere, 2.1 ml (2.1 mmol) of a 1.00 M solution of diisobutylaluminium hydride in methylene chloride are slowly added dropwise to an ice-cooled solution of 200 mg (0.347 mmol) of 1-[4-(pyridin-2yl)phenyl]-1-oxo-5-(S)-2,5-di[(tert-butoxycarbonyl)amino]-4(S)-hydroxy-6-phenyl-2-azahexane in 5 ml of THF (foams). After 2 hours, 7 ml of ethyl acetate are added and, after a further 30 min, 70 ml of methanol. The reaction mixture is warmed to room temperature and stirred for 2 hours; 0.5 ml of water and 5 g of sodium sulfate are added and the mixture is stirred again for 1 hour to complete the reaction. The salts are filtered off and the filtrate is concentrated by evaporation. Medium-pressure chromatography (SiO$_2$, hexane/ethyl acetate 3:2→ethyl acetate) yields the title compound: m.p. 184° C.; TLC (hexane/ethyl acetate 1:1); R$_f$=0.26; FAB MS (M+H)$^+$=563.

The synthesis of the starting material, 1-[4-(pyridin-2-yl) phenyl]-1-oxo-5-(S)-2,5-di[(tert-butoxycarbonyl)amino]-4 (S)-hydroxy-6-phenyl-2-azahexane, is carried out via the following steps:

Step (1) 4-Pyridin-2-yl)-benzoic acid methyl ester 24.0 g (150 mmol) of 4-cyanobenzoic acid methyl ester (Fluka, Buchs, Switzerland) in 150 ml of toluene are placed under an acetylene atmosphere in an autoclave and 0.30 g (1.6 mmol) of cobaltocene (=dicyclopentadienylcobalt; Aldrich, Milwaukee, USA), is added. The mixture is then subjected to an acetylene pressure of 15 atm, heated at 180° C. and stirred for 12 hours. After cooling and release of the pressure, 9.5 g of active carbon are added to the black suspension; the mixture is diluted with 250 ml of toluene, stirred for 30 min, filtered and concentrated by evaporation. Crystallisation from warm ether by the addition of hexane yields the title compound: m.p. 96° C.; TLC (hexane/ethyl acetate 4:1): $R_f$=0.37; FAB MS (M+H)$^+$=214. Further produce can be obtained from the mother liquor by column chromatography (SiO$_2$, hexane/ethyl acetate (19:1→4:1).

Step (2) 4-(Pyridin-2-yl)-benzoic acid 12.85 g (60.2 mmol) of 4-(pyridin-2-yl)-benzoic acid methyl ester in 125 ml of methanol and 67 ml of 1 N sodium hydroxide solution are stirred at room temperature for 6 hours. The resulting solution is partially concentrated by evaporation; the aqueous residue is extracted with ethyl acetate and acidified to pH≈1.5 with 2 N HCl solution. The title compound precipitates out and can be filtered off and washed with water: TLC (ethyl acetate): $R_f$=0.35; FAB MS (M+H)$^+$=200.

Step (3) 4-Pyridin-2-yl)-benzoic acid iso-butyloxyformic acid anhydride

With the exclusion of air, 6.0 g (30 mmol) of 4-(pyridin-2-yl)-benzoic acid are suspended at –20° C. in 90 ml of THF, and 9.90 ml (90 mmol) of N-methyl-morpholine and 4.32 ml (33 mmol) of isobutyl chloroformate are added. After 30 min, the mixture is filtered, washed with a small amount of cold THF, and the filtrate is partially concentrated by evaporation; the residue is diluted with methylene chloride, washed with ice-water and cold brine, dried (Na$_2$SO$_4$) and concentrated by evaporation to form the title compound: $^1$H-NMR (CDCl$_3$) i.a. 8.75 (m, 1 H), 8.16 (AB, J=8, 4 H), 7.81 (m, 2 H), 7.32 (4-line system, J=5, 1 H), 4.16 (d, J=7, 2 H), 2.10 (9-line system, J=7, 1 H), 1.02 (d, J=7, 6 H).

Step (4) 1-(R)-Cyano-2(S)-(N-tert-butoxycarbonylamino)-3-phenylpropyl[4-(2-pyridyl)]-benzoate At 0° C., 250 mg (0.9 mmol) of benzyltriethylammonium chloride are added to 2.0 g (30 mmol) of potassium cyanide in 7.5 ml of water and 7.5 ml of methylene chloride. Then a solution of 6.21 g (24.9 mmol) of Boc-(L)-phenylalaninal in 10 ml of methylene chloride and a solution of ≈309 mmol of 4-(pyridin-2-yl)-benzoic acid-iso-butyloxyformic acid anhydride in 10 ml of methylene chloride are simultaneously added dropwise. After 20 min at 0° C., stirring is carried out at room temperature for a further 4 hours and the reaction mixture is finally diluted with methylene chloride/water. The aqueous phase is separated off and extracted 2× with methylene chloride; the organic phase is washed 3× with water and brine, dried (Na$_2$SO$_4$) and concentrated by evaporation. Column chromatography (SiO$_2$; hexane/ethyl acetate 4:1→2:1) yields a ≈5:1 mixture of 1-(R)-cyano-2(S)-(N-tert-butoxycarbonylamino)-3-phenylpropyl[4-(2-pyridyl)]-benzoate and 1-(S)-cyano-2(S)-(N-tert-butoxycarbonylamino)-3-phenylpropyl[4-(2-pyridyl)]-benzoate: TLC (hexane/ethyl acetate 4:1): $R_f$=0.11; FAB MS (M+H)$^+$=458; $^1$H-NMR (CDCl$_3$) i.a. 5.66 (d, J=6, ⅚ H, 1-(R) epimer), 5.53 (m, ⅙ H, 1-(S) epimer).

Digestion in DIPE results in diastereoisomerically pure 1-(R)-cyano-2(S)-(N-tert-butoxycarbonylamino)-3-phenylpropyl[4-(2-pyridyl)]-benzoate: m.p. 140–141° C.

Step (5) 4-(S)-1,4-Di[(tert-butoxycarbonyl)amino]-3(R)-[4-(pyridin-2-yl)phenyl]-carbonyloxy-5-phenyl-1-azapent-1-ene 2.29 g (5.0 mmol) of 1-(R)-cyano-2(S)-(N-tert-butoxycarbonylamino)-3-phenylpropyl[4-(2-pyridyl)]-benzoate are dissolved in 80 ml of methanol, and 900 mg (15 mmol) of acetic acid and 661.5 mg (5 mmol) of tert-butyl carbazate are added; after the addition of 2.3 g of Raney nickel, the mixture is hydrogenated. The partially precipitated produce is dissolved by the addition of methanol and gentle heating; the catalyst is filtered off and the filtrate is concentrated by evaporation. The residue is taken up in ethyl acetate/sat. NaHCO$_3$ solution; the aqueous phase is separated off and extracted in further 2× with ethyl acetate. The organic phases are washed with brine, dried (Na$_2$SO$_4$) and concentrated by evaporation. Medium-pressure chromatography (SiO$_2$; hexane/ethyl acetate 4:1→ethyl acetate) yields the title compound: m.p. 195–196° C.; TLC (hexane/ethyl acetate 1:1): $R_f$=0.39; FAB MS (M+H)$^+$=575.

Step (6) 1-[4-(Pyridin-2-yl)phenyl]-1-oxo-5-(S)-2,5-di [(tert-butoxycarbonyl)amino]-4(S)-hydroxy-6-phenyl-2-azahexane Under a nitrogen atmosphere, 111 mg (85%; 1.5 mmol) of NaCNBH$_3$ are added to a solution of 862 mg (1.5 mmol) of 4-(S)-1,4-di[(tert-butoxycarbonyl)amino]-3(R)-[4-(pyridin-2-yl)phenyl]-carbonyloxy-5-phenyl-1-azapent-1-ene in 10 ml of THF. A solution of 290 mg (1.5 mmol) of p-toluenesulfonic acid in 4 ml of THF is added dropwise thereto. After stirring for 2.5 hours, a further 55 mg of NaCNBH$_3$ and 145 mg of p-toluenesulfonic acid in 2 ml of THF are added and the mixture is stirred again for 2.5 hours. The reaction mixture is then poured into 230 ml of a 1% solution of K$_2$B$_4$O$_7$·4H$_2$O in water, stirred overnight to complete the reaction, filtered and washed with water. The residue is taken un in ethyl acetate; the solution is washed with brine, dried (Na$_2$SO$_4$) and concentrated by evaporation {→4-(S)-1,4-di[(tert-butoxycarbonyl)amino]-3(S)-[4-(pyridin-2-yl)phenyl]-carbonyloxy-5-phenyl-1-azapentane: TLC (hexane/ethyl acetate 1:1): $R_f$=0.45}. The resulting foam is dissolved in 25 ml of diethylene glycol dimethyl ether; 250 μl of 7-methyl-1,5,7-triazabicyclo[4.4.0]dec-5-ene (Fluka, Buchs, Switzerland) are added and the mixture is heated at 80° C. for 1.5 hours. The mixture is concentrated by evaporation under a high vacuum and the residue is taken up in ethyl acetate/water; the aqueous phase is separated off and extracted a further 2× with ethyl acetate. The organic phases are washed with brine, dried (Na$_2$SO$_4$) and concentrated by evaporation. Crystallisation from DIPE/hexane yields the title compound: m.p. 104–105° C.; TLC (hexane/ethyl acetate 1:1): $R_f$=0.20; FAB MS (M+H)$^+$=577.

Example 47

[4-(Pyridin-2-yl)-phenyl]-4(S)-hydroxy-5(S)-2,5-bis [N-(N-methoxycarbonyl-(L)-iso-leucyl)amino]-6-phenyl-2-azahexane Under a nitrogen atmosphere, 0.45 g (1.5 mmol) of N-methoxycarbonyl-(L)-iso-leucine, 0.85 g (4.5 mmol) of EDC and 0.4 g (3 mmol) of HOBT are dissolved in 10 ml of DMF. After the addition of 1.26 ml of TEA and stirring for 10 min, a solution of 0.96 g (1.5 mmol) of 1-[4-(pyridin-2-yl)-phenyl]-4(S)-hydroxy-2-amino-5(S)-N-(N-methoxycarbonyl-(L)-iso-leucyl)-amino-6-phenyl-2-azahexane hydrochloride in 10 ml of DMF is then added dropwise. After 2 hours, the reaction mixture is concentrated by evaporation. The resulting oil is taken up in methylene chloride and washed with water, 2× sat. NaHCO$_3$ solution, water and brine. The aqueous phases are extracted with methylene chloride; the combined organic phases are dried (Na$_2$SO$_4$) and concentrated by evaporation. The residue is digested first in DIPE and then in methylene chloride/ether, then filtered off and dried to yield the title compound: TLC: R$_f$=0.45 (ethyl acetate); HPLC$_{20-100}$: t$_{Ret}$=11.71; FAB MS (M+H)$^+$=705.

The starting material is prepared as follows:

47a) 1-[4-(Pyridin-2-yl)-phenyl]-4(S)-hydroxy-2-(N-Boc-amino)-5(S)-trifluoroacetyl-amino-6phenyl-2-azahexane Analogously to Example 37e), 7 g (23 mmol) of N-1-(tert-butoxycarbonyl)-N-2-[4-(pyridin-2-yl)-benzyl]-hydrazine are reacted with 6 g (23 mmol) of (2R)-[(1'S)-trifluoroacetyl-amino-2'-phenylethyl]oxirane in 125 ml of isopropanol at 80° C. to form the title compound. TLC: R$_f$=0.33 (methylene chloride/methanol: 1/1); HPLC$_{20-100}$: t$_{Ret}$=12.76; FAB MS (M+H)$^+$=559.

47b) 1-[4-(Pyridin-2-yl)-phenyl]-4(S)-hydroxy-2-(N-Boc-amino)-5(S)-amino-6-phenyl-2-azahexane Analogously to Example 40e, 5.6 g (10 mmol) of 1-[4-(pyridin-2-yl)-phenyl]-4(S)-hydroxy-5(S)-2-(N-Boc-amino)-5-(trifluoroacetyl-amino)-6-phenyl-2-azahexane are dissolved in 130 ml of methanol, heated to 65° C. and converted into the title compound by the dropwise addition of 50 ml of a 1 M aqueous potassium carbonate solution. TLC: R$_f$=0.17 (methylene chloride/methanol: 9/1); HPLC$_{20-100}$: t$_{Ret}$=8.50; FAB MS (M+H)$^+$=463.

47c) 1-[4-(Pyridin-2-yl)-phenyl]-4(S)-hydroxy-2-N-Boc-amino-5(S)-N-(N-methoxycarbonyl-(L)-iso-leucyl)amino-6-phenyl-2-azahexane Analogously to Example 1, a solution of 1.62 g (3.5 mmol) of 1-[4-(pyridin-2-yl)-phenyl]-4(S)-hydroxy-2-(N-Boc-amino)-5(S)-amino-6-phenyl-2-azahexane in 25 ml of DMF is added dropwise to a mixture of 1.06 g (5.6 mmol) of N-methoxycarbonyl-(L)-iso-leucine, 2.01 g (10.5 mmol) of EDC and 0.95 g (7 mmol) of HOBT in 20 ml of DMF. After working up, the crude product is digested in DIPE, filtered off and dried. TLC: R$_f$=0.59 (ethyl acetate); HPLC$_{20-100}$: t$_{Ret}$=12.52. FAB MS (M+H)$^+$=634.

47d) 1-[4-(Pyridin-2-yl)-phenyl]-4(S)-hydroxy-2-amino-5(S)-N-(N-methoxycarbonyl-(L)-iso-leucyl)amino-6-phenyl-2-azahexane hydrochloride Analogously to Example 40g, 40 ml of 4 M HCl in dioxane are added to 1.9 g (3 mmol) of 1-[4-(pyridin-2-yl)-phenyl]-4-(S)-hydroxy-2-N-Boc-amino-5(S)-N-(N-methoxycarbonyl-(L)-iso-leucyl)amino-6-phenyl-2-azahexane and the mixture is diluted with 3 ml of DMF. After 2.5 hours, the mixture is worked up. The title compound is obtained: TLC: R$_f$=0.55 (methylene chloride/methanol: 9/1); HPLC$_{20-100}$: t$_{Ret}$=8.74; FAB MS (M+H)$^+$=534.

Example 48

1-[4-(Pyridin-2-yl)-phenyl]-4(S)-hydroxy-2-N-(N-methoxy-carbonyl-(L)-valyl)amino-5(S)-N-(N-methoxycarbonyl-(L)-tert-leucyl)amino-6-phenyl-2-azahexane Analogously to Example 1, a solution of 0.964 g (1.5 mmol) of 1-[4-(pyridin-2-yl)-phenyl]-4(S)-hydroxy-2-amino-5(S)-N-(N-methoxycarbonyl-(L)-tert-leucyl)amino-6-phenyl-2-aza-hexane hydrochloride in 10 ml of DMF is added dropwise to a mixture of 0.42 g (2.4 mmol) of N-methoxycarbonyl-(L)-valine, 0.862 g (4.5 mmol) of EDC, 0.405 g (3 mmol) of HOBT and 1.26 ml of TEA in 10 ml of DMF. After working up, the crude product is digested in DIPE, filtered off and dried. Subsequent column chromatography (SiO$_2$; hexane/ethyl acetate: 1/1 to 3/1) yields the pure title compound (TLC: R$_f$=0.35 (ethyl acetate); HPLC$_{20-100}$: t$_{Ret}$=10.9. FAB MS (M+H)$^+$=691.

Example 49

1-[4-(Pyridin-2-yl)-phenyl]-4(S)-hydroxy-2-N-(N-methoxy-carbonyl-(L)-tert-leucyl)amino-5-(S)-N-(N-methoxycarbonyl-(L)-valyl)amino-6-phenyl-2-azahexane Analogously to Example 1, a solution of 0.315 g (0.5 mmol) of 1-[4-(pyridin-2-yl)-phenyl]-4(S)-hydroxy-2-amino-5(S)-N-(N-methoxycarbonyl-(L)-valyl)amino-6-phenyl-2-azahexane hydrochloride in 3 ml of DMF is added dropwise to a mixture of 0.152 g (0.8 mmol) of N-methoxycarbonyl-(L)-tert-leucine, 0.287 g (1.5 mmol) of EDC, 0.135 g (1mmol) of HOBT and 0.49 ml of TEA in 3 ml of DMF. After working up, the crude product is purified by subsequent medium-pressure column chromatography (SiO$_2$; hexane/ethyl acetate) to yield the title compound. TLC: R$_f$=0.35 (ethyl acetate); HPLC$_{20-100}$: t$_{Ret}$=11.05. FAB MS (M+H)$^+$=691.

The starting compounds are prepared as follows:

49a) 1-[4-(Pyridin-2yl)-phenyl]-4(S)-hydroxy-2-N-Boc-amino-5(S)-N-(N-methoxycarbonyl-(L)-valyl)amino-6-phenyl-2-azahexane Analogously to Example 1, a solution of 4.1 g (8.87 mmol) of 1-[4-(pyridin-2-yl)-phenyl]-4-(S)-hydroxy-2-(N-Boc-amino)-5(S)-amino-6-phenyl-2-azahexane (Example 47b) in 50 ml of DMF is added dropwise to a mixture of 2.49 g (14.2 mmol) of N-methoxycarbonyl-(L)-valine, 5.1 g (26.6 mmol) of EDC, 2.4 g (17.7 mmol) of HOBT and 7.45 ml of TEA in 50 ml of DMF. After working up, the crude product is digested 2× in DIPE, filtered off and dried to yield the title compound. TLC: R$_f$=0.42 (ethyl acetate); HPLC$_{20-100}$: t$_{Ret}$=11.92. FAB MS (M+H)$^+$=620.

49b) 1-[4-(Pyridin-2-yl)-phenyl]-4(S)-hydroxy-2-amino-5(S)-N-(N-methoxycarbonyl-(L)-valyl)amino-6-phenyl-2-azahexane hydrochloride Analogously to Example 37f), 30 ml of 4 M HCl in dioxane are added to 3.5 g (5.65 mmol) of 1-[4-(pyridin-2-yl)-phenyl]-4-(S)-hydroxy-2-N-Boc-amino-5(S)-N-(N-methoxycarbonyl-(L)-valyl)amino-6-phenyl-2-azahexane and the mixture is diluted with 5 ml of DMF. After 3.5 hours, the mixture is worked up. The title compound is obtained: TLC: R$_f$=0.53 (methylene chloride/methanol: 9/1); HPLC$_{20-100}$: t$_{Ret}$=8.00; FAB MS (M+H)$^+$=520.

Example 50

1-[4-(Pyridin-2-yl)-phenyl]-4(S)-hydroxy-2-N-(N-methoxy-carbonyl-(L)-valyl)amino-5(S)-N-(N-methoxycarbonyl-(L)-iso-leucyl)amino-6-phenyl-2-azahexane Analogously to Example 46, 0.96 g (1.5 mmol) of 1-[4-(pyridin-2-yl)-phenyl]-4(S)-hydroxy-2-amino-5(S)-N-(N-methoxycarbonyl-(L)-iso-leucyl)amino-6-phenyl-2-azahexane 3 HCl (Example 47d) in 10 ml of DMF are reacted with 0.263 g (1.5 mmol) of N-methoxycarbonyl-(L)-valine, 0.446 g (1.5 mmol) of TPTU and 0.78 ml (4.5

Example 51

1-[4-(Pyridin-2-yl)-phenyl]-4(S)-hydroxy-2-N-(N-methoxy-carbonyl-(L)-iso-leucyl)amino-5(S)-N-(N-methoxycarbonyl-(L)-valyl)amino-6-phenyl-2-azahexane Analogously to Example 1, a solution of 1.26 g (2 mmol) of 1-[4-(pyridin-2-yl)-phenyl]-4(S)-hydroxy-2-amino-5(S)-N-(N-methoxycarbonyl-(L)-valyl)amino-6-phenyl-2-azahexane hydrochloride (Example 49b) in 12 ml of DMF is added dropwise to a mixture of 0.6 g (3.2 mmol) of N-methoxycarbonyl-(L)-iso-leucine, 1.14 g (6 mmol) of EDC, 0.54 g (4 mmol) of HOBT and 1.68 ml of TEA in 13 ml of DMF. After working up, the crude product is digested in DIPE and purified by subsequent medium-pressure column chromatography ($SiO_2$; hexane/ethyl acetate) to yield the title compound. TLC: $R_f$=0.32 (ethyl acetate); $HPLC_{20-100}$: $t_{Ret}$=11.04. FAB MS $(M+H)^+$=691.

Example 52

1-[4-(Pyridin-2-yl)-phenyl]-4(S)-hydroxy-2-N-(N-ethoxy-carbonyl-(L)-valyl)amino-5(S)-N-(N-methoxycarbonyl-(L)-valyl)amino-6-phenyl-2-azahexane Analogously to Example 1, a solution of 0.629 g (1 mmol) of 1-[4-(pyridin-2-yl)-phenyl]-4(S)-hydroxy-2-amino-5(S)-N-(N-methoxycarbonyl-(L)-valyl)amino-6-phenyl-2-azahexane hydrochloride (Example 49b) in 5 ml of DMF is added dropwise to a mixture of 0.303 g (1.6 mmol) of N-ethoxycarbonyl-(L)-valine, 0.575 g (3 mmol) of EDC, 0.27 g (2 mmol) of HOBT and 0.98 ml of TEA in 7 ml of DMF. After working up, the crude product is digested in DIPE and purified by subsequent medium-pressure column chromatography ($SiO_2$; hexane/ethyl acetate) to yield the title compound. TLC: $R_f$=0.33 (ethyl acetate); $HPLC_{20-100}$: $t_{Ret}$=11.13. FAB MS $(M+H)^+$=691.

Example 53

1-[4-(Pyrid-2-yl)-phenyl]-4(S)-hydroxy-5(S)-2,5-bis[N-(N-methoxycarbonyl-(L)-tert-leucyl)amino]-6-phenyl-2-azahexane methansulfonate salt 210 mg (0.28 mmol) of 1-[4-(pyridin-2-yl)-phenyl]-4(S)-hydroxy-5(S)-2,5-bis[N-(N-methoxycarbonyl-(L)-tert-leucyl)amino]-6-phenyl-2-azahexane (Example 46) are dissolved in 10 ml of methylene chloride with heating and 19.5 µl (0.3 mmol) of methansulfonic acid are added. The title compound is precipitated with ether, filtered off and dried under reduced pressure at 50° C. FAB MS $(M+H)^+$=705. $^1$H-NMR ($CD_3OD$) (chemical shifts of the pyridine protons of the free base in brackets); δ: 8.81 (8.6), 8.65 (7.9), 8.36 (7.8), 8.05 (7.35) and also, in addition, signals of the methyl group of the salt: δ: 2.7 ppm.

Example 54

1-[4-(Pyrid-2-yl)-phenyl]-4(S)-hydroxy-5(S)-2,5-bis[N-(N-methoxycarbonyl-(L)-tert-leucyl)amino]-6-phenyl-2-azahexane hydrochloride salt 70 mg (0.094 mmol) of 1-[4-(pyrid-2-yl)-phenyl]-4(S)-hydroxy-5(S)-2,5-bis[N-(N-methoxycarbonyl-(L)-tert-leucyl)amino]-6-phenyl-2-azahexane (Example 46) are dissolved in 6 ml of dioxane, and 25 µl of a 4 M HCl solution is dioxane are added. The resulting precipitate is filtered off and dried. FAB MS $(M+H)^+$=705. $^1$H-NMR ($CD_3OD$) (chemical shifts of the pyridine protons of the free base in brackets); δ: 8.81 (8.6), 8.65 (7.9), 8.36 (7.8), 8.05 (7.35). Elemental analysis of the hydrate of the title compound: Cl found: 4.6%; calc.: 4.63%.

Example 55

Gelatin Solution

A sterile-filtered aqueous solution, containing 20% cyclodextrins as solubiliser, of one of the compounds of formula I mentioned in the preceding Examples (e.g. the title compound from Example 2) as active ingredient, is so mixed, with heating and under aseptic conditions, with a sterile gelatin solution containing phenol as preservative that 1.0 ml of solution has the following composition:

| | |
|---|---|
| active ingredient | 3 mg |
| gelatin | 150 mg |
| phenol | 4.7 mg |
| dist. water containing 20% cyclodextrins as solubiliser | 1.0 ml |

Example 56

Sterile Dry Substance for Injection 5 mg of one of the compounds of formula I mentioned in the preceding Examples (for example the title compound from Example 3) as active ingredient are dissolved in 1 ml of an aqueous solution containing 20 mg of mannitol and 20% cyclodextrins as solubiliser. The solution is sterile-filtered and, under aseptic conditions, introduced into a 2 ml ampoule, deep-frozen and lyophilised. Before use, the lyophilisate is dissolved in 1 ml of distilled water or 1 ml of physiological saline. The solution is administered intramuscularly or intravenously. The formulation can also be introduced into double-chamber disposable syringes.

Example 57

Nasal Spray 500 mg of finely ground (<5.0 mm) powder of one of the compounds of formula I mentioned in the preceding Examples (for example the compound from Example 4) are suspended as active ingredient in a mixture of 3.5 ml of Myglyol 812® and 0.08 g of benzyl alcohol. The suspension is introduced into a container having a metering valve, 5.0 g of Freon 12® (dichlorodifluoromethane; trade mark of DuPont) are introduced under pressure through the valve into the container. The "Freon" is dissolved in the Myglyol/benzyl alcohol mixture by shaking. The spray container contains approximately 100 single doses which can be administered individually.

Example 58

Film-coated Tablets

The following constituents are processed for the preparation of 10 000 tablets each comprising 100 mg of active ingredient:

| | |
|---|---|
| active ingredient | 1000 g |
| corn starch | 680 g |
| colioidal silicic acid | 200 g |
| magnesium stearate | 20 g |
| stearic acid | 50 g |
| sodium carboxymethyl starch | 250 g |
| water | quantum satis |

A mixture of one of the compounds of formula I mentioned in the preceding Examples (for example the compound from Example 5) as active ingredient, 50 g of corn starch and the colloidal silicic acid is processed with a starch paste made from 250 g of corn starch and 2.2 kg of demineralised water to form a moist mass. That mass is forced through a sieve of 3 mm mesh size and dried in a fluidised bed dryer at 45° for 30 min. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly convex tablets.

Example 59

Capsules (I)

A compound from one of the afore-mentioned Examples (e.g. the title compound from Example 6) is micronised (particle size about 1 to 100 µm) using a customary knife mixer (e.g. Turmix). ®Pluronic F 68 (block polymer of polyethylene and polypropylene glycols; Wyandotte Chem. Corp. Michigan, USA; also obtainable from Emkalyx, France; trade mark of BASF) is likewise micronised using a customary mixer and the fines content is removed using a sieve (0.5 mm) and using further as below. 16.00 g of sesame oil are placed in a glass beaker and 1.20 g of the micronised active ingredient, 1.20 g of the fines content of ®Pluronic F 68 and 1.20 g of hydroxypropylmethylcellulose (Cellulose HP-M-603 from Shin-Etsu chemicals Ltd., Tokyo, JP) are added with stirring using a stirring device (IKA-Werk, FRG) combined with a toothed stirred (diameter: 46 mm) (stirring speed: 2000 rev/min). Twenty minutes' stirring at the speed indicated produces a suspension of pasty consistency which is introduced into hard gelatin capsules (20×40 mm; R. P. Scherer AG. Eberbach, FRG).

Example 60

Capsules (II)

For the preparation of 10 000 capsules comprising 100 mg of active ingredient (from one of the afore-mentioned Examples, for example the title compound from Example 7) per capsule, the following constituents are processed as follows:

| | |
|---|---|
| active ingredient | 1000 g |
| ® Pluronic F 68 | 1000 g |
| hydroxypropylmethylcellulose | 1000 g |
| sesame oil | 1000 g |
| (for origin of constituents see Example 10) | |

The sesame oil is placed in a heatable vessel (Fryma) and the ®Pluronic F 68 is scattered in. The vessel is heated at 60° C. and the ®Pluronic F 68 is distributed with stirring (duration about 2 hours). With stirring and homogenisation, the mixture is cooled to about 30° C. The hydroxypropylmethylcellulose and the active ingredient are scattered in and, with stirring and homogenisation (about 1 hour), distributed in the oil mass. The suspension of pasty consistency is introduced into hard gelatin capsules (size 0; obtainable, for example, from Elanco or Parke-Davies (Caprogel)) or soft gelatin capsules (20 mm oblong; R. P. Scherer AG, Eberbach, FRG) using customary apparatus.

Example 61

Dispersion

For the preparation of a dispersion comprising 120.0 mg of active ingredient/10 ml (preferably the title compound from Example 46), the following constituents are processed as follows:

| | |
|---|---|
| active ingredient | 120.0 mg |
| ® Klucel HF (hydroxypropylcellulose; Hercules, Germany) | 50.0 mg |
| ® Tween 20 (polyoxyethylene sorbitan monolaurate; Fluka, Buchs, Switzerland) | 100.0 mg |
| demineralised water | 10.0 ml |

The demineralised water is placed in a container; the hydroxypropylcellulose is scattered in slowly with stirring using a magnetic stirrer and allowed to swell for 1 hour. The polyoxyethylene sorbitan monolaurate is then added and the mixture is stirred for 5 min using the magnetic stirrer. Finally, the active ingredient is added and the mixture is stirred for 15 min using the magnetic stirrer.

Example 62

Inhibitory Activity in Respect of HIV-1-protease

Using the test system described above with the icosapeptide RRSNQVSQNYPIVQNIQGRR, the $IC_{50}$ values given below are obtained for the following Examples:

| Example | $IC_{50}$ (µM) |
|---|---|
| 1 | 0.032 |
| 2 | 0.014 |
| 3 | 0.041 |
| 4 | 0.038 |
| 5 | 0.04 |
| 6 | 0.022 |
| 7 | 0.013 |
| 8 | 0.01 |
| 9 | 0.019 |
| 10 | 0.02 |
| 11 | 0.037 |
| 12 | 0.02 |
| 13 | 0.032 |
| 14 | 0.031 |
| 15 | 0.05 |
| 16 | 0.033 |
| 17 | 0.018 |
| 18 | 0.025 |
| 19 | 0.022 |
| 20 | 0.015 |
| 21 | 0.043 |
| 22 | 0.04 |
| 23 | 0.034 |
| 24 | 0.05 |
| 25 | 0.1 |
| 26 | 0.021 |

87

-continued

| Example | IC$_{50}$ ($\mu$M) |
|---|---|
| 27 | 0.027 |
| 27 (1-methyl-1H-tetrazolyl isomer) | 0.051 |
| 28 | 0.083 |
| 29 | 0.014 |
| 30 | 0.054 |
| 31 | 0.171 |
| 34 | 0.072 |
| 35 | 0.058 |
| 37 | 0.029 |
| 38 | 0.085 |
| 39 | 0.012 |
| 40 | 0.021 |
| 41 | 0.032 |
| 42 | 0.015 |
| 43 | 0.037 |
| 44 | 0.029 |
| 45 | 0.012 |
| 46 | 0.026 |
| 47 | 0.04 |
| 48 | 0.031 |
| 49 | 0.02 |
| 50 | 0.028 |
| 51 | 0.034 |
| 52 | 0.034 |

Example 63

Protection of MT-2 Cells Against HIV Infection

Using the afore-mentioned test system, in inhibiting the infection of MT-2 cells by the virus strain HIV-1/MN the title compound from Example 46, 1-[4-(pyridin-2-yl)phenyl]-4(S)-hydroxy-5(S)-2,5-bis[N-(N-methoxycarbonyl-(L)-tert-leucyl)amino]-6-phenyl-2-azahexane, has the following ED$_{90}$ value: ED$_{90}$=0.003 $\mu$M.

Example 64

Blood Levels in Mice

Using the afore-mentioned test system for the determination of the pharmacokinetics of compounds of formula I, the title compound from Example 46, 1-[4-(pyridin-2-yl)phenyl]-4(S)-hydroxy-5(S)-2,5-bis[N-(N-methoxycarbonyl-(L)-tert-leucyl)amino]-6-phenyl-2-azahexane, exhibits in mice the following blood levels after oral administration of 120 mg/kg:

| Plasma level ($\mu$M) of title compound of Example 46 | |
|---|---|
| 30 min | 90 min after administration |
| 21.83 | 31.76 |

Example 65

Formulation as Solution (I)

The formulation comprises 100 mg of the title compound from Example 46 as active ingredient, 100 mg of racemic lactic acid (90%), Cellulose-HP-M-603, silica gel (Aerosil 200) and deionised water (2 g).

Example 66

Formulation as Solution (II)

The formulation comprises 18.4 mg of the title compound from Example 46 as active ingredient, 5 mg of Cellulose-HPM-603, 40 mg of N-methylpyrrolidone and double-distilled water ad 1 ml.

Example 67

Analogously to one of the afore-mentioned processes, there are prepared

A) 1-[4-(pyridin-2-yl)phenyl]-4(R)-hydroxy-5(S)-2,5-bis[N-(N-methoxycarbonyl-(L)-tert-leucyl)amino]-6-phenyl-2-azahexane;

B) 1-[4-(pyridin-2-yl)phenyl]-4(R)-hydroxy-5(R)-2,5-bis[N-(N-methoxycarbonyl-(L)-tert-leucyl)amino]-6-phenyl-2-azahexane;

C) 1-[4-(pyridin-2-yl)phenyl]-4(S)-hydroxy-5(S)-2-[N-(N-methoxycarbonyl-(L)-tert-leucyl)amino]-5-[N-(N-methoxycarbonyl-(D)-tert-leucyl)amino]-6-phenyl-2-azahexane; or D) 1-[4-(pyridin-2-yl)phenyl]-4(S)-hydroxy-5(S)-2-[N-(N-methoxycarbonyl-(D)-tert-leucyl)amino]-5-[N-(N-methoxycarbonyl-(L)-tert-leucyl)amino]-6-phenyl-2-azahexane.

What is claimed is:

1. A compound of the formula XX,

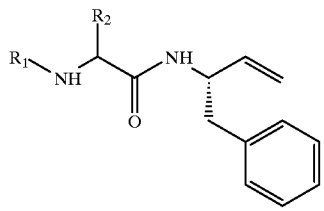

(XX)

wherein R$_1$ is methoxycarbonyl or ethoxycarbonyl and R$_2$ is tert-butyl, or a salt thereof.

2. A compound of the formula IV,

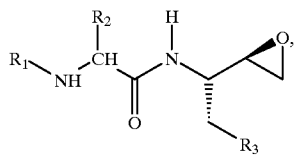

(IV)

wherein R$_1$ is methoxycarbonyl or ethoxycarbonyl, R$_2$ is tert-butyl and R$_3$ is is phenyl that is unsubstituted or substituted by one or more lower alkoxy radicals, or C$_4$–C$_8$cycloalkyl.

3. A compound of the formula III*

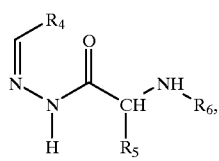

(III*)

where R$_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, R$_5$ is tert-butyl and $R_6$ is methoxy- or ethoxycarbonyl; or a salt thereof where a salt-forming group is present.

4. A compound of the formula XII,

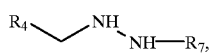
(XII)

where $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl and $R_7$ is an amino protecting group, or a salt thereof if a salt-forming group is present.

5. A compound of the formula XII*,

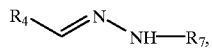
(XII*)

wherein $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl and $R_7$ is an amino protecting group, or a salt thereof if a salt-forming group is present.

6. A compound of the formula III,

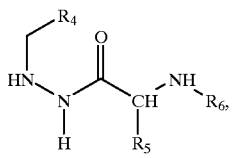
(III)

wherein $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, $R_5$ is isopropyl, sec-butyl, tert-butyl or methylthiomethyl, and $R_6$ is lower alkoxycarbonyl, or a salt thereof, provided that at least one salt-forming group is present.

7. A compound of the formula V,

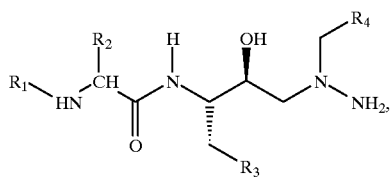
(V)

wherein $R_1$ is lower alkoxycarbonyl,
$R_2$ is secondary or tertiary lower alkyl or lower alkylthio-lower alkyl,
$R_3$ is phenyl that is unsubstituted or substituted by one or more lower alkoxy radicals, or $C_4$–$C_8$cycloalkyl, and $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, or a salt thereof, provided that at least one salt-forming group is present.

8. A compound of the formula VII,

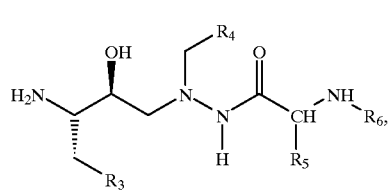
(VII)

wherein $R_3$ is phenyl that is unsubstituted or substituted by one or more lower alkoxy radicals, or $C_4$–$C_8$cycloalkyl, $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, $R_5$ is secondary or tertiary lower alkyl or lower alkylthio-lower alkyl, and $R_6$ is lower alkoxycarbonyl, or a salt thereof, provided that at least one salt-forming group is present.

9. A compound of the formula IX,

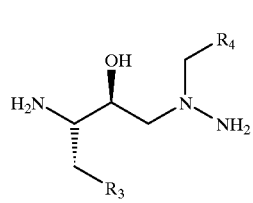
(IX)

wherein $R_3$ is phenyl that is unsubstituted or substituted by one or more lower alkoxy radicals, or $C_4$–$C_8$cycloalkyl, and $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, or a salt thereof, provided that at least one salt-forming group is present.

10. A compound of the formula XXIV,

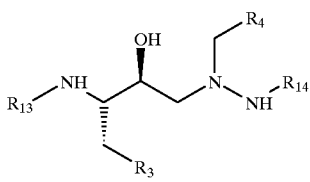
(XXIV)

wherein $R_{13}$ and $R_{14}$ are amino-protecting groups, which are different from one another, $R_3$ is phenyl that is unsubstituted or substituted by one or more lower alkoxy radicals, or $C_4$–$C_8$cycloalkyl, and $R_4$ is phenyl or cyclohexyl each substituted in the 4-position by unsaturated heterocyclyl that is bonded by way of a ring carbon atoms, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, or a salt thereof, provided that at least one salt-forming group is present.

11. A compound of the formula XXV,

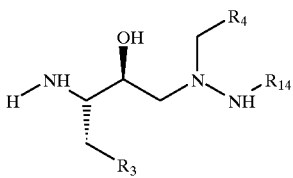
(XXV)

where $R_{14}$ is an amino-protecting group, $R_3$ is phenyl that is unsubstituted or substituted by one or more lower alkoxy radicals, or $C_4$–$C_8$cycloalkyl, and $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl-lower alkyl, or a salt thereof, provided that at least one salt-forming group is present.

12. A compound of the formula XXVI,

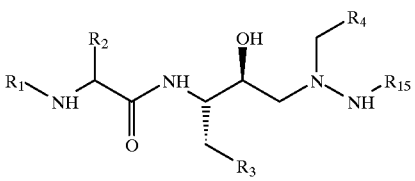
(XXVI)

wherein $R_{15}$ is an amino-protecting group, $R_1$ is lower alkoxycarbonyl, $R_2$ is secondary or tertiary lower alkyl or lower alkylthio-lower alkyl, $R_3$ is phenyl that is unsubstituted or substituted by one or more lower alkoxy radicals, or $C_4$–$C_8$cycloalkyl, and $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl and sulfonyl and is unsubstituted or substituted by lower alkyl or by phenyl alkyl, or a salt thereof, provided that at least one salt-forming group is present.

* * * * *